United States Patent
Fujiwara et al.

(10) Patent No.: US 11,448,962 B2
(45) Date of Patent: Sep. 20, 2022

(54) RESIST COMPOSITION AND PATTERNING PROCESS

(71) Applicant: Shin-Etsu Chemical Co., Ltd., Tokyo (JP)

(72) Inventors: Takayuki Fujiwara, Joetsu (JP); Kenichi Oikawa, Joetsu (JP); Masaki Ohashi, Joetsu (JP); Tomohiro Kobayashi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 38 days.

(21) Appl. No.: 16/743,177

(22) Filed: Jan. 15, 2020

(65) Prior Publication Data

US 2020/0249571 A1 Aug. 6, 2020

(30) Foreign Application Priority Data

Feb. 5, 2019 (JP) .............................. JP2019-018638

(51) Int. Cl.
| | |
|---|---|
| *G03F 7/004* | (2006.01) |
| *G03F 7/38* | (2006.01) |
| *C07C 381/12* | (2006.01) |
| *G03F 7/038* | (2006.01) |
| *G03F 7/32* | (2006.01) |
| *G03F 7/20* | (2006.01) |

(52) U.S. Cl.
CPC .......... *G03F 7/0045* (2013.01); *C07C 381/12* (2013.01); *G03F 7/0048* (2013.01); *G03F 7/0382* (2013.01); *G03F 7/2041* (2013.01); *G03F 7/322* (2013.01); *G03F 7/325* (2013.01); *G03F 7/38* (2013.01)

(58) Field of Classification Search
CPC .... G03F 7/0045; G03F 7/0392; G03F 7/0397; G03F 7/322; G03F 7/325; G03F 7/38; G03F 7/40; C07C 381/12
See application file for complete search history.

(56) References Cited

U.S. PATENT DOCUMENTS

| | | | |
|---|---|---|---|
| 9,029,065 B2 | 5/2015 | Aqad et al. | |
| 9,122,155 B2* | 9/2015 | Ohashi ................. | G03F 7/0046 |
| 2015/0168830 A1 | 6/2015 | Goto et al. | |
| 2015/0338732 A1 | 11/2015 | Yoshino | |
| 2017/0299963 A1* | 10/2017 | Fujiwara ............... | G03F 7/0397 |
| 2018/0275516 A1* | 9/2018 | Fujiwara ............... | G03F 7/2041 |

FOREIGN PATENT DOCUMENTS

| | | |
|---|---|---|
| JP | 4621806 B2 | 1/2011 |
| JP | 2012-106980 A | 6/2012 |
| JP | 2014-48500 A | 3/2014 |
| JP | 2014-122204 A | 7/2014 |
| JP | 2014-199389 A | 10/2014 |
| JP | 2014-215549 A | 11/2014 |
| KR | 10-2012-0033224 A | 4/2012 |
| TW | 201435492 A | 9/2014 |
| TW | 201441764 A | 11/2014 |
| WO | 2014/017408 A1 | 1/2014 |

OTHER PUBLICATIONS

Office Action dated Sep. 2, 2020, issued in counterpart TW Application No. 109103127. (11 pages).
Office Action dated Jan. 21, 2021, issued in counterpart TW Application No. 109103127. (13 pages).
Office Action dated Sep. 3, 2021, issued in counterpart KR application No. 10-2020-0013781, with English translation (10 pages).
Office Action dated Oct. 12, 2021, issued in counterpart JP application No. 2019-018638, with English translation. (5 pages).

* cited by examiner

*Primary Examiner* — John S Chu
(74) *Attorney, Agent, or Firm* — WHDA, LLP

(57) ABSTRACT

A resist composition comprising a sulfonium salt having formula (1) as PAG, a base polymer, and an organic solvent, when processed by lithography, has light transmittance, acid diffusion suppressing effect, and excellent lithography performance factors such as DOF, LWR and MEF. A lithography process for forming a resist pattern from the composition is also provided.

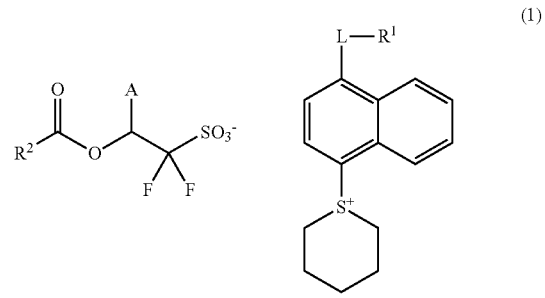

(1)

14 Claims, No Drawings

RESIST COMPOSITION AND PATTERNING PROCESS

CROSS-REFERENCE TO RELATED APPLICATION

This non-provisional application claims priority under 35 U.S.C. § 119(a) on Patent Application No. 2019-018638 filed in Japan on Feb. 5, 2019, the entire contents of which are hereby incorporated by reference.

TECHNICAL FIELD

This invention relates to a resist composition comprising a specific photoacid generator and a pattern forming process using the resist composition.

BACKGROUND ART

To meet the demand for higher integration and operating speeds in LSIs, further miniaturization of the pattern rule is desired. The requirement to form resist patterns of high resolution necessitates not only to improve lithography properties as typified by pattern profile, contrast, mask error factor (MEF), depth of focus (DOF), critical dimension uniformity (CDU), and line width roughness (LWR), but also to minimize surface defects on the resist pattern after development.

One means for improving lithography performance is the modification or structural optimization of photoacid generators for suppressing the diffusion of generated acid and adjusting their solvent solubility. It is known that resist materials using cations having a high transmittance to exposure wavelength, for example, the cations described in Patent Documents 1 and 2 give better results with respect to DOF. It is expectable that photoacid generators having a sterically bulky structure or polar group are effective for suppressing the diffusion of generated acid, thus improving lithography factors like MEF and LWR.

CITATION LIST

Patent Document 1: JP 4621806
Patent Document 2: JP-A 2014-122204 (U.S. Pat. No. 9,029,065)

DISCLOSURE OF INVENTION

While resist patterns of high resolution are recently required, resist compositions comprising conventional PAGs do not always meet lithography performance factors such as DOF, CDU, LWR and MEF. Although the resist compositions using high transmittance cations as mentioned above are effective for DOF improvement, the results of other lithography factors such as LWR and MEF are not necessarily satisfactory.

An object of the invention is to provide a resist composition which is improved in light transmittance, acid diffusion suppressing effect, and lithography factors such as DOF, CDU, LWR and MEF when processed by photolithography using high-energy radiation such as KrF excimer laser, ArF excimer laser, EB or EUV as the energy source, and a pattern forming process using the same.

The inventors have found that a resist composition comprising as PAG a salt obtained by combing a cation of specific structure having a high transmittance with an anion of specific structure has excellent lithography performance factors such as DOF, LWR and MEF and is quite effective for precise micropatterning.

In one aspect, the invention provides a resist composition comprising (A) a photoacid generator in the form of a sulfonium salt having the formula (1), (B) a base polymer adapted to change its solubility in a developer under the action of an acid, and (C) an organic solvent.

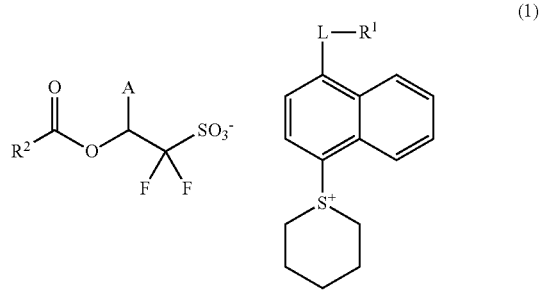

(1)

Herein $R^1$ is hydrogen or a $C_1$-$C_{10}$ monovalent hydrocarbon group which may contain a heteroatom, $R^2$ is a $C_1$-$C_{40}$ monovalent hydrocarbon group which may contain a heteroatom, L is a single bond, ether bond or thioether bond, and "A" is hydrogen or trifluoromethyl, Preferably, L is an ether bond and $R^1$ is 2-methoxyethyl. Also preferably, "A" is trifluoromethyl.

In a preferred embodiment, the base polymer (B) comprises recurring units having the formula (a) and recurring units having the formula (b).

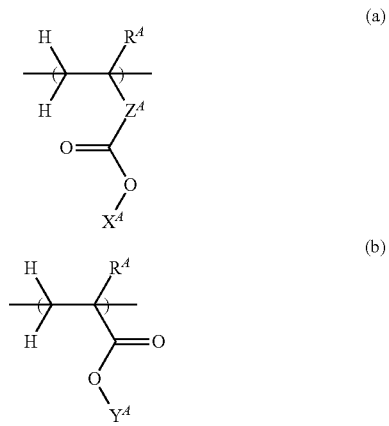

Herein $R^A$ is hydrogen or methyl, $Z^A$ is a single bond, phenylene group, naphthylene group or (backbone)-C(=O)—O—$Z^{A1}$—, $Z^{A1}$ is a $C_1$-$C_{10}$ alkanediyl group which may contain a hydroxyl moiety, ether bond, ester bond or lactone ring, or phenylene group or naphthylene group, $X^A$ is an acid labile group, and $Y^A$ is hydrogen or a polar group having at least one structure selected from the class consisting of hydroxyl, cyano, carbonyl, carboxyl, ether bond, ester bond, sulfonic acid ester bond, carbonate bond, lactone ring, sultone ring and carboxylic anhydride (—C(=O)—O—C(=O)—).

More preferably, $Z^A$ is a single bond, and $X^A$ is a group having the formula (xa) or (xb):

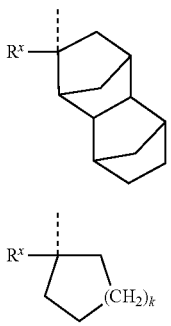

(xa)

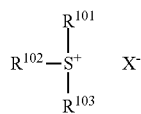

(xb)

wherein $R^x$ is a $C_1$-$C_5$ straight or branched monovalent hydrocarbon group, k is 1 or 2, and the broken line designates a valence bond.

Also more preferably, $Y^A$ is a monocyclic lactone ring.

In a preferred embodiment, the base polymer (B) comprises recurring units of at least two types having the formula (a), or the base polymer (B) comprises recurring units of at least two types having the formula (b).

The resist composition may further comprise (D) a photoacid generator other than the sulfonium salt having formula (1).

Preferably, the other photoacid generator (D) has the formula (2) or (3).

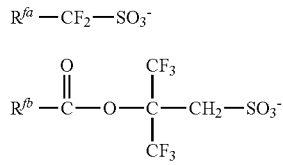

(2)

Herein $R^{101}$, $R^{102}$ and $R^{103}$ are each independently a $C_6$-$C_{20}$ aryl group which may contain a heteroatom, any two of $R^{101}$, $R^{102}$ and $R^{103}$ may bond together to form a ring with the sulfur atom to which they are attached, and $X^-$ is an anion having the formula (2A) or (2B):

$$R^{fa}-CF_2-SO_3^-$$ (2A)

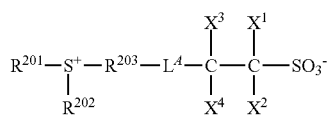

(2B)

wherein $R^{fa}$ is fluorine, a $C_1$-$C_4$ perfluoroalkyl group, or a $C_1$-$C_{40}$ monovalent hydrocarbon group which may contain a heteroatom, and $R^{fb}$ is a $C_1$-$C_{40}$ monovalent hydrocarbon group which may contain a heteroatom.

$$R^{201}-S^+-R^{203}-L^A-\underset{\underset{X^4}{|}}{\overset{\overset{X^3}{|}}{C}}-\underset{\underset{X^2}{|}}{\overset{\overset{X^1}{|}}{C}}-SO_3^-$$ (3)
$$\quad\ \ |$$
$$\quad R^{202}$$

Herein $R^{201}$ and $R^{202}$ are each independently a $C_1$-$C_{30}$ monovalent hydrocarbon group which may contain a heteroatom, $R^{203}$ is a $C_1$-$C_{30}$ divalent hydrocarbon group which may contain a heteroatom, any two of $R^{201}$, $R^{202}$ and $R^{203}$ may bond together to form a ring with the sulfur atom to which they are attached, $L^A$ is a single bond, ether bond or a $C_1$-$C_{20}$ divalent hydrocarbon group which may contain a heteroatom, $X^1$, $X^2$, $X^3$ and $X^4$ are each independently hydrogen, fluorine or trifluoromethyl, at least one of $X^1$, $X^2$, $X^3$ and $X^4$ being fluorine or trifluoromethyl.

The resist composition may further comprise an amine compound and/or a surfactant which is insoluble in water and soluble in alkaline developer.

In another aspect, the invention provides a pattern forming process comprising the steps of applying the resist composition defined above to form a resist film, exposing a selected region of the resist film to KrF excimer laser, ArF excimer laser, EB or EUV, and developing the exposed resist film in a developer.

In a preferred embodiment, the developing step uses an alkaline aqueous solution as the developer, thereby forming a positive pattern in which an exposed region of the resist film is dissolved away and an unexposed region of the resist film is not dissolved.

In another preferred embodiment, the developing step uses an organic solvent as the developer, thereby forming a negative pattern in which an unexposed region of the resist film is dissolved away and an exposed region of the resist film is not dissolved.

Preferably, the organic solvent is at least one solvent selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

In a preferred embodiment, the exposure step is carried out by immersion lithography while a liquid having a refractive index of at least 1.0 is held between the resist film and a projection lens.

The process may further comprise the step of coating a protective film on the resist film prior to the exposure step, wherein immersion lithography is carried out while the liquid is held between the protective film and the projection lens.

Advantageous Effects of Invention

When the resist composition comprising the specific sulfonium compound as PAG is processed by lithography, a resist pattern having improved lithography factors including DOF, LWR and MEF can be formed.

DESCRIPTION OF THE PREFERRED EMBODIMENTS

The singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. In chemical formulae, the broken line denotes a valence bond; Me stands for methyl, tBu for tert-butyl, Ac for acetyl, and Ph for phenyl. It is understood that for some structures represented by chemical formulae, there can exist enantiomers and diastereomers because of the presence of asymmetric carbon atoms. In such a case, a single formula collectively represents all such isomers. The isomers may be used alone or in admixture.

The abbreviations have the following meaning.
EB: electron beam
EUV: extreme ultraviolet
GPC: gel permeation chromatography
Mw: weight average molecular weight
Mw/Mn: molecular weight dispersity
PAG: photoacid generator
PEB: post-exposure bake
LWR: line width roughness
MEF: mask error factor
DOF: depth of focus
CDU: critical dimension uniformity
Resist Composition The invention provides a resist composition comprising (A) a photoacid generator in the form of a specific sulfonium salt, (B) a base polymer adapted to change its solubility in a developer under the action of an acid, and (C) an organic solvent.

(A) Photoacid Generator

The photoacid generator as component (A) is a sulfonium salt having the formula (1).

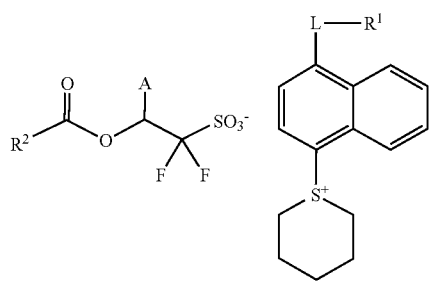

(1)

In formula (1), $R^1$ is hydrogen or a $C_1$-$C_{10}$ monovalent hydrocarbon group which may contain a heteroatom. The monovalent hydrocarbon group may be straight, branched or cyclic and examples thereof include alkyl groups such as methyl, ethyl, propyl, isopropyl, n-butyl, n-pentyl, n-hexyl, n-octyl, n-nonyl, and n-decyl, cycloalkyl groups such as cyclopentyl and cyclohexyl, and monovalent saturated cyclic hydrocarbon groups such as adamantyl. Also included are substituted forms of the foregoing in which some hydrogen is substituted by a moiety containing a heteroatom such as oxygen, sulfur, nitrogen or halogen, or some carbon is replaced by a moiety containing a heteroatom such as oxygen, sulfur or nitrogen, so that the group may contain a hydroxyl, cyano, carbonyl, ether bond, ester bond, sulfonic acid ester bond, carbonate bond, lactone ring, sultone ring, carboxylic anhydride (—C(=O)—O—C(=O)—), or haloalkyl moiety. Preferably, $R^1$ is hydrogen, methyl, 2-methoxyethyl or (2-methoxyethoxy)ethyl, with 2-methoxyethyl being more preferred.

L is a single bond, ether bond or thioether bond, with an ether bond being preferred.

Examples of the cation in the sulfonium salt having formula (1) are shown below, but not limited thereto.

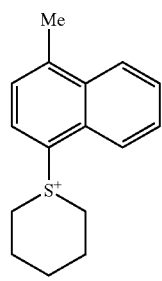

(1-A-1)

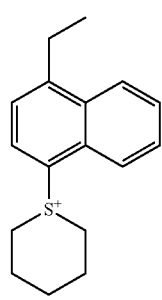

(1-A-2)

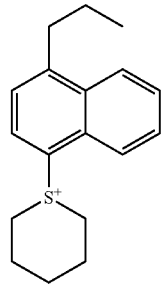

(1-A-3)

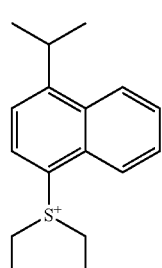

(1-A-4)

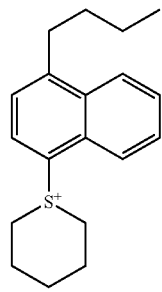

(1-A-5)

(1-A-6)

(1-A-7)

(1-A-8)

(1-A-9)

(1-A-10)

(1-A-11)

(1-A-12)

(1-A-13)

(1-A-14)

(1-A-15)

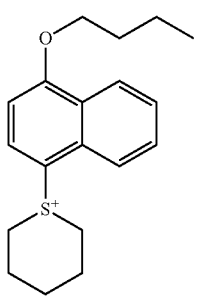
(1-A-16)
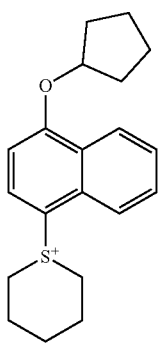
(1-A-17)
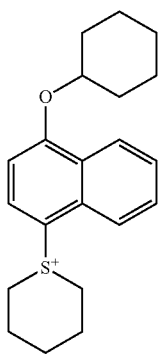
(1-A-18)
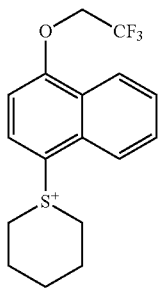
(1-A-19)
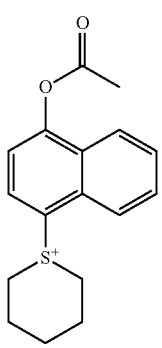
(1-A-20)
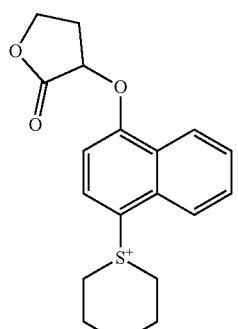
(1-A-21)
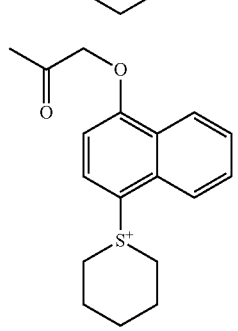
(1-A-22)
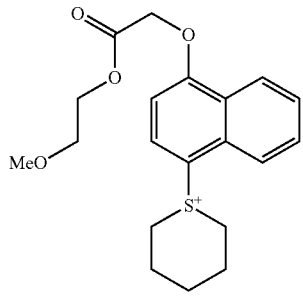
(1-A-23)
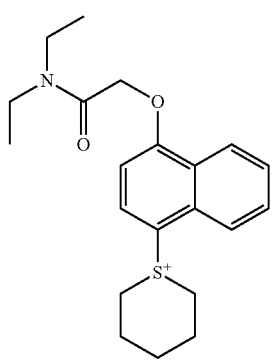
(1-A-24)
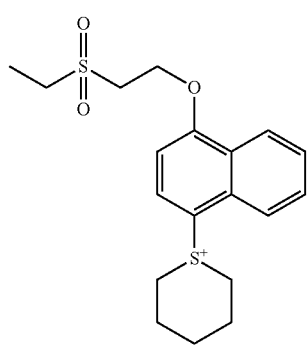
(1-A-25)

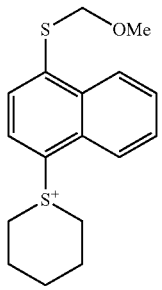
(1-A-26)

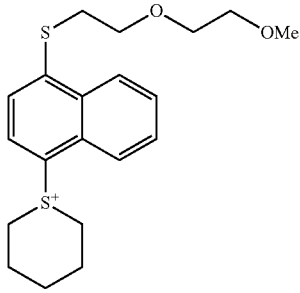
(1-A-27)

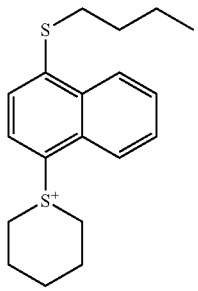
(1-A-28)

Of the cations in the salt having formula (1), the cations having formulae (1-A-7), (1-A-11) and (1-A-15) are preferred. Due to the resonance and induction effects of oxygen atom attached to the naphthalene ring, the absorption wavelength of these cations is shifted as compared with the unsubstituted naphthalene ring. These cations thus have high transmittance to ArF excimer laser radiation (wavelength 193 nm) or the like, leading to improvements in lithography factors such as DOF. Also the diffusion of proton is suppressed due to the inclusion of glyme chain in the chainlike section, leading to improvements in lithography factors such as LWR and MEF.

The position of a substituent on the naphthalene ring should be the position shown in formula (1) from the standpoints of ease of synthesis, storage stability, and transmittance, and the number of substituents on the naphthalene ring should be one. If more than one substituent is introduced, the cation is significantly stabilized and the acid generation efficiency is reduced. This can lead to a lowering of sensitivity.

With respect to the ring structure moiety including $S^+$, not only the 6-membered ring structure shown in formula (1), but also the following structures are known.

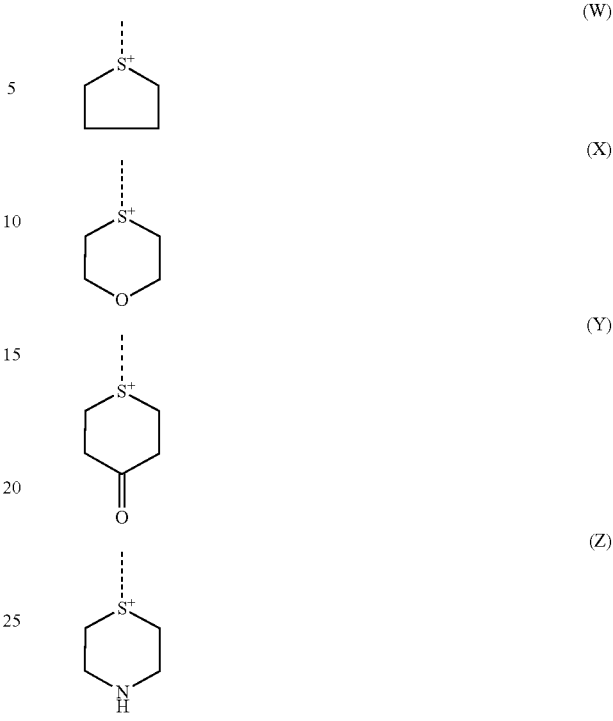

The structure of formula (W) or (Y) is less stable because of the steric or electronic factor due to ring strain, with the risk that storage stability is degraded when combined with basic compounds such as amines. The structure of formula (Z) includes the basic amine site, leaving the risks of low sensitivity and poor storage stability. The structure of formula (X) can invite degradation of lithography performance as compared with the structure in formula (1) although the detail is not well understood. For example, it is presumed that the structure of formula (X) can be decomposed upon light exposure to open its ring and to generate a vinyl ether in part, which vinyl ether, in turn, undergoes various reactions with moisture, hydroxyl groups on the backbone, and the like in the resist under acid conditions. As a result, lithography performance is degraded.

In formula (1), $R^2$ is a $C_1$-$C_{40}$ monovalent hydrocarbon group which may contain a heteroatom. The monovalent hydrocarbon group may be straight, branched or cyclic. Examples thereof include straight, branched or cyclic alkyl groups such as methyl, ethyl, propyl, isopropyl, n-butyl, sec-butyl, tert-butyl, tert-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, tricyclo[$5.2.1.0^{2,6}$]decanyl, adamantyl and adamantylmethyl; straight, branched or cyclic alkenyl groups such as vinyl, allyl, propenyl, butenyl, hexenyl, and cyclohexenyl; aryl groups such as phenyl and naphthyl; heteroaryl groups such as thienyl; hydroxyphenyl groups such as 4-hydroxyphenyl; alkoxyphenyl groups such as 4-methoxyphenyl, 3-methoxyphenyl, 2-methoxyphenyl, 4-ethoxyphenyl, 4-tert-butoxyphenyl, and 3-tert-butoxyphenyl; alkylphenyl groups such as 2-methylphenyl, 3-methylphenyl, 4-methylphenyl, 4-ethylphenyl, 4-tert-butylphenyl, 4-n-butylphenyl, 2,4-dimethylphenyl and 2,4,6-triisopropylphenyl; alkylnaphthyl groups such as methylnaphthyl and ethylnaphthyl; alkoxynaphthyl groups such as methoxynaphthyl, ethoxynaphthyl, n-propoxynaphthyl, and n-butoxynaphthyl; dialkylnaphthyl groups such as dimethylnaphthyl and diethylnaphthyl; dialkoxynaphthyl groups such as dimethoxynaphthyl and diethoxynaphthyl; aralkyl groups such as benzyl, 1-phenylethyl and 2-phenylethyl; and aryloxoalkyl groups, specifically 2-aryl-2-oxoethyl groups such as 2-phenyl-2-oxoethyl, 2-(1-naphthyl)-2-oxoethyl, and 2-(2-naphthyl)-2-oxoethyl. Also included are substituted forms of the foregoing groups in which some hydrogen is substituted by a moiety containing a heteroatom such as oxygen, sulfur, nitrogen or halogen, or a moiety containing a heteroatom such as oxygen, sulfur or nitrogen intervenes between carbon atoms so that the group may contain a hydroxyl, cyano, carbonyl, ether bond, ester bond, sulfonic acid ester bond, carbonate bond, lactone ring, sultone ring, carboxyl, carboxylic anhydride, or haloalkyl moiety. Preferably $R^2$ is a group having an adamantane skeleton or fused ring lactone skeleton.

In formula (1), "A" is hydrogen or trifluoromethyl, preferably trifluoromethyl.

Examples of the anion in the sulfonium salt having formula (1) are shown below, but not limited thereto. Herein "A" is as defined above.

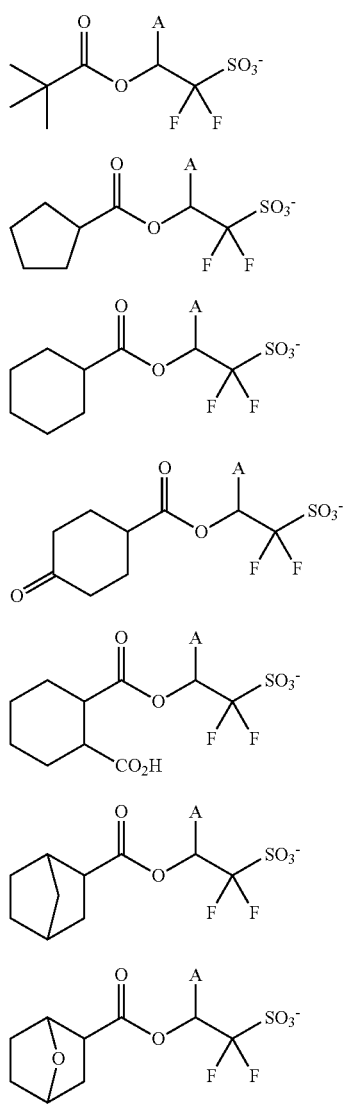

(1-B-1)

(1-B-2)

(1-B-3)

(1-B-4)

(1-B-5)

(1-B-6)

(1-B-7)

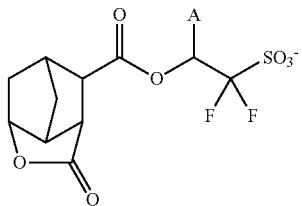

(1-B-8)

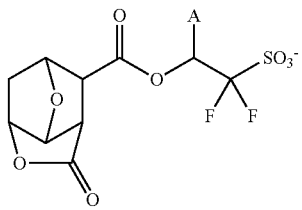

(1-B-9)

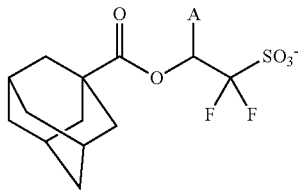

(1-B-10)

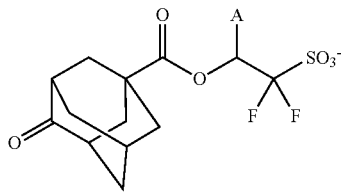

(1-B-11)

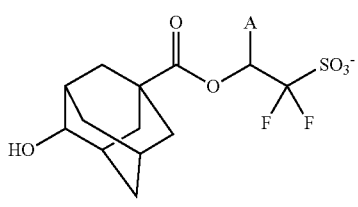

(1-B-12)

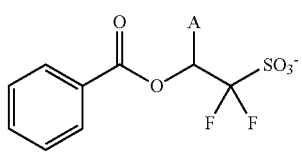

(1-B-13)

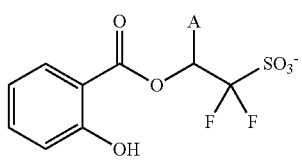

(1-B-14)

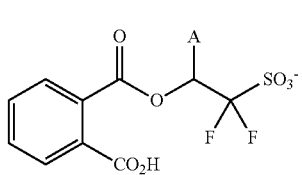

(1-B-15)

(1-B-16) 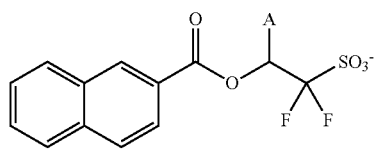
(1-B-17) 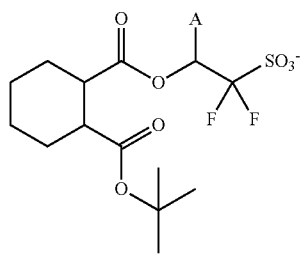
(1-B-18) 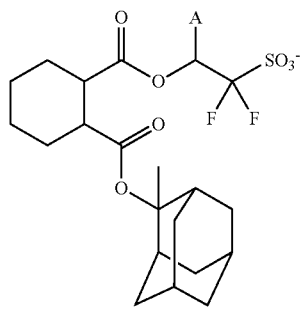
(1-B-19) 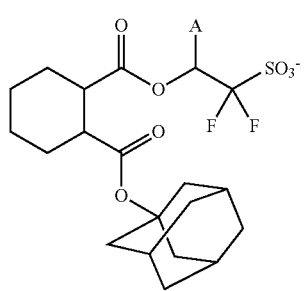
(1-B-20) 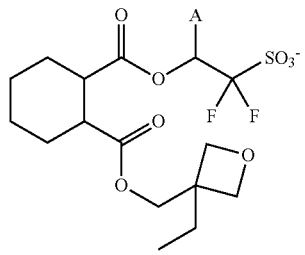
(1-B-21) 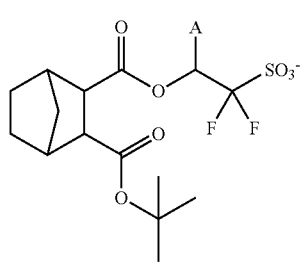
(1-B-22) 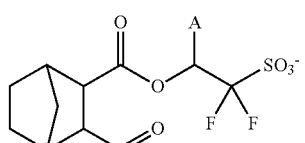
(1-B-23) 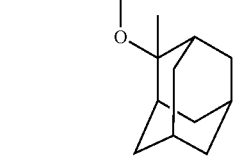
(1-B-24) 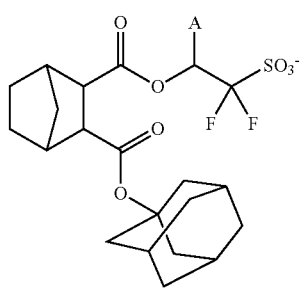
(1-B-25) 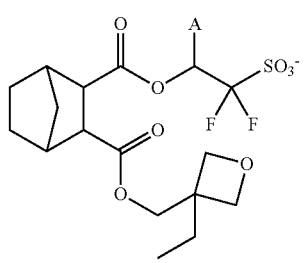
(1-B-26) 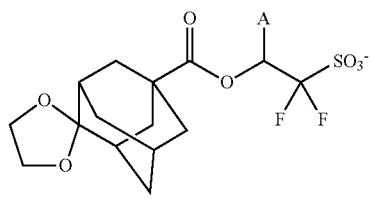
(1-B-27) 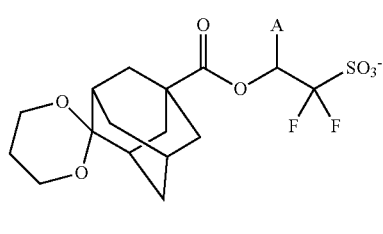

(1-B-28)
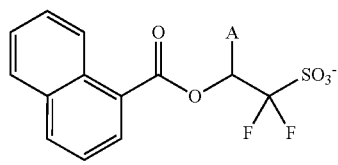
(1-B-29)
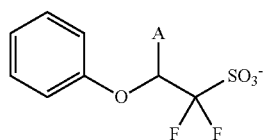
(1-B-30)
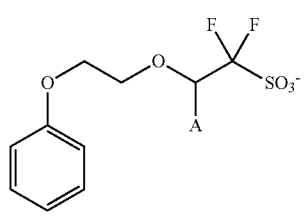
(1-B-31)
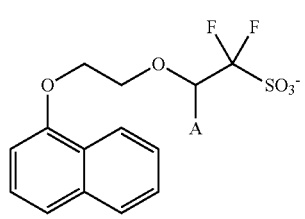
(1-B-32)
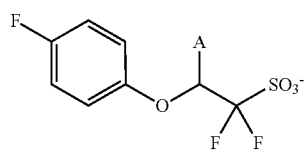
(1-B-33)
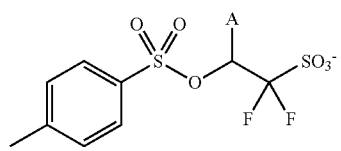
(1-B-34)
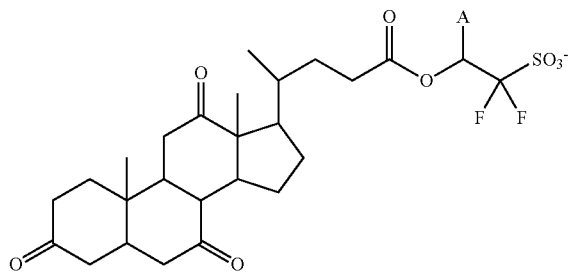
(1-B-35)
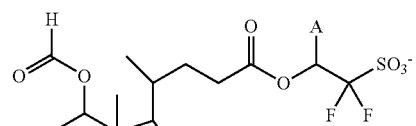
(1-B-36)
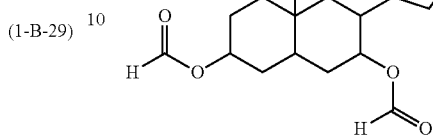
(1-B-37)
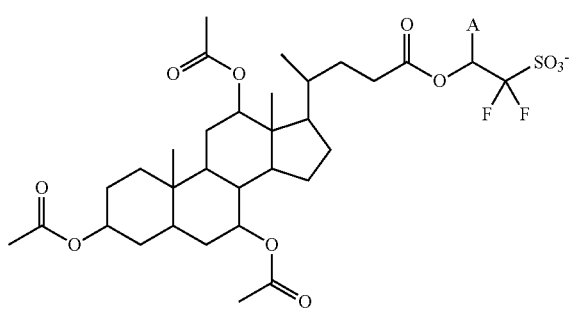
(1-B-38)
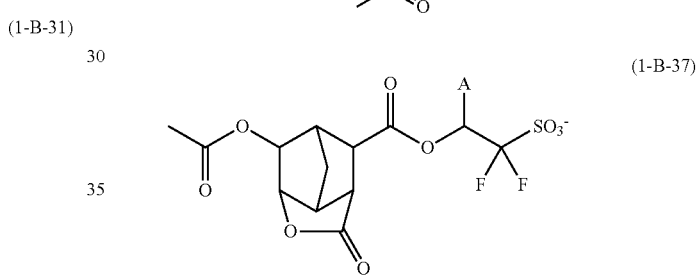
(1-B-39)
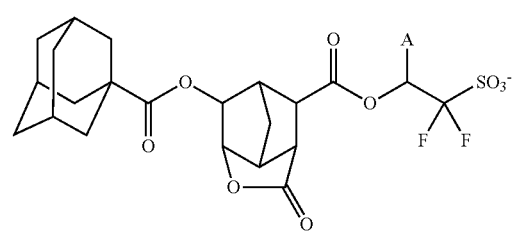
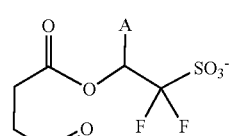
(1-B-40)
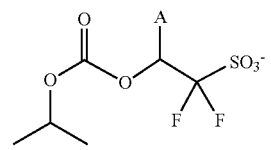

(1-B-41)
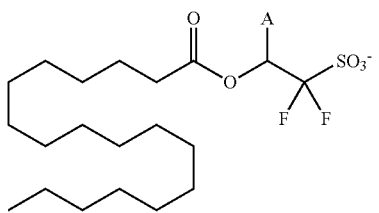
(1-B-42)
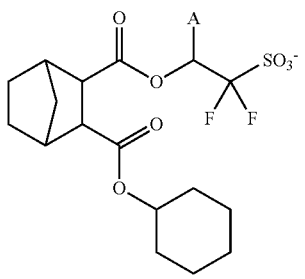
(1-B-43)
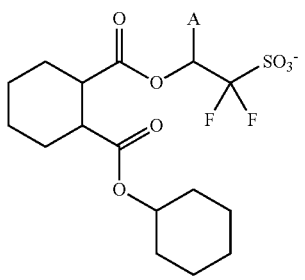
(1-B-44)
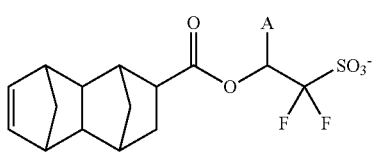
(1-B-45)
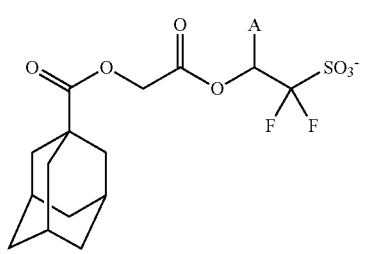
(1-B-46)
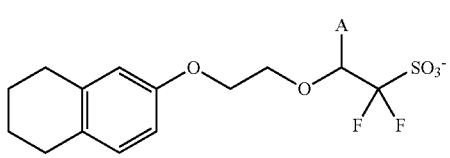
(1-B-47)
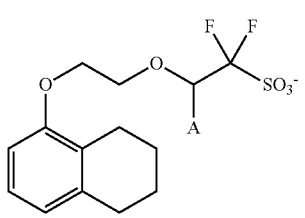
(1-B-48)
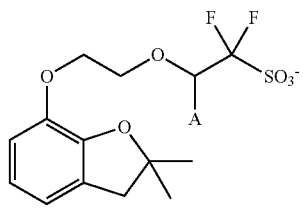
(1-B-49)
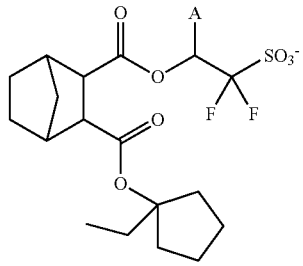
(1-B-50)
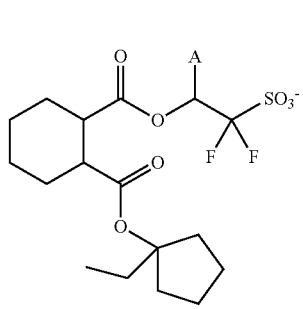
(1-B-51)
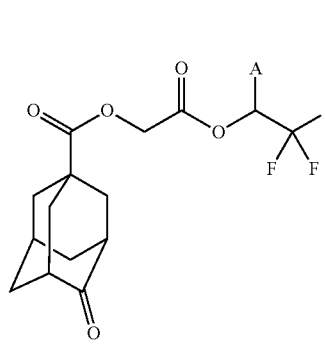
(1-B-52)
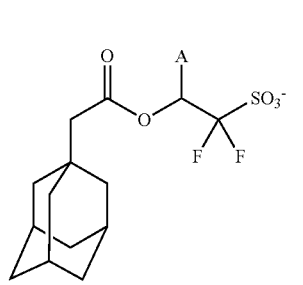
(1-B-53)
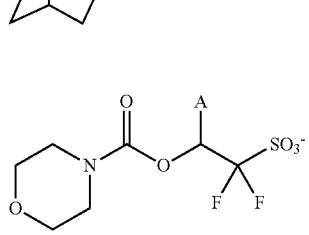

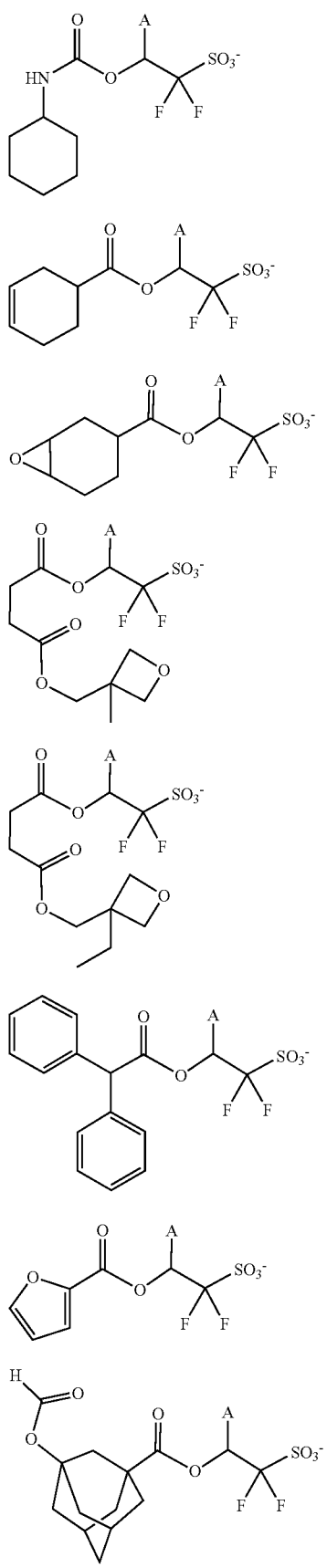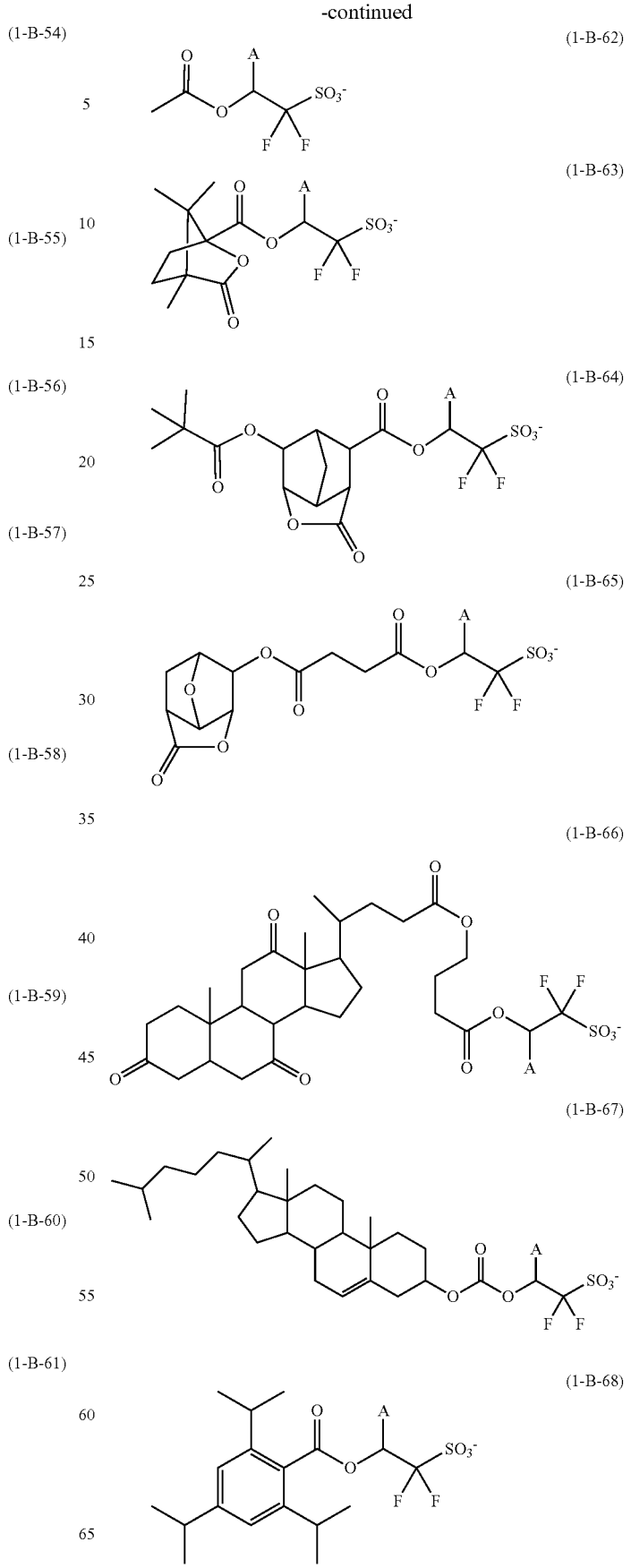

(1-B-69)

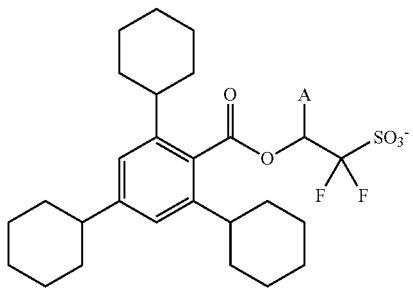

Of the anions in the salt having formula (1), the anions having formulae (1-B-10), (1-B-11), (1-B-34), (1-B-38), (1-B-44), and (1-B-69) are preferred, and the anions having formulae (1-B-10), (1-B-11), and (1-B-38) are more preferred. Although the detail is not well understood, the salts of formula (1) having such anions often exhibit satisfactory lithography performance independent of the dissolution properties of a polymer to be combined therewith. This is probably attributable to their structure having a good balance of hydrophilicity and hydrophobicity and capable of adequately controlling acid diffusion.

Exemplary structures for the salt of formula (1) include arbitrary combinations of cations with anions, both as exemplified above. Preferred are combinations of cations having formulae (1-A-7), (1-A-11) and (1-A-15) with anions having formulae (1-B-10), (1-B-11), (1-B-34), (1-B-38), (1-B-44), and (1-B-69). The combination of the cation having formula (1-A-11) with the anion having formula (1-B-10) is most preferred.

The resist composition comprising component (A) or PAG is processed by photolithography using high-energy radiation such as KrF or ArF excimer laser, EB or EUV. In this context, it is a chemically amplified resist composition having minimal defectivity, controlled acid diffusion, and improved lithography factors such as DOF, LWR and CDU.

In the resist composition, the PAG as component (A) is preferably blended in an amount of 0.5 to 30 parts by weight, more preferably 0.5 to 20 parts by weight, even more preferably 1.0 to 15 parts by weight per 80 parts by weight of the base polymer as component (B) to be described below. An amount of the PAG in the range ensures good resolution and leaves no foreign particles after resist development or during stripping.

(B) Base Polymer

Component (B) is a base polymer adapted to change its solubility in a developer under the action of an acid. It is preferably a polymer comprising recurring units having the formula (a) and recurring units having the formula (b).

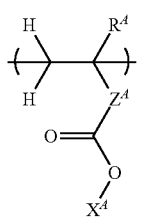
(a)

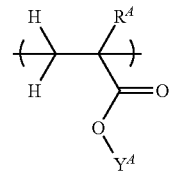
(b)

In formulae (a) and (b), $R^A$ is hydrogen or methyl. $Z^A$ is a single bond, phenylene group, naphthylene group or (backbone)-C(=O)—O—$Z^{A1}$—, wherein $Z^{A1}$ is a $C_1$-$C_{10}$ alkanediyl group which may contain a hydroxyl moiety, ether bond, ester bond or lactone ring, or phenylene group or naphthylene group. $X^A$ is an acid labile group. $Y^A$ is hydrogen or a polar group having at least one structure selected from the class consisting of hydroxyl, cyano, carbonyl, carboxyl, ether bond, ester bond, sulfonic acid ester bond, carbonate bond, lactone ring, sultone ring and carboxylic anhydride (—C(=O)—O—C(=O)—).

The $C_1$-$C_{10}$ alkanediyl group may be straight, branched or cyclic, and examples thereof include methylene, ethane-1,1-diyl, ethane-1,2-diyl, propane-1,2-diyl, propane-2,2-diyl, propane-1,3-diyl, 2-methylpropane-1,3-diyl, butane-1,3-diyl, butane-2,3-diyl, butane-1,4-diyl, pentane-1,3-diyl, pentane-1,4-diyl, 2,2-dimethylpropane-1,3-diyl, pentane-1,5-diyl, hexane-1,6-diyl, cyclopentane-1,2-diyl, cyclopentane-1,3-diyl, and cyclohexane-1,6-diyl.

Examples of the structure of formula (a) wherein $Z^A$ is a variant include the structures described in U.S. Pat. No. 9,164,384 (JP-A 2014-225005, paragraph [0015]). Of these, preferred structures are illustrated below. Herein $R^A$ and $X^A$ are as defined above.

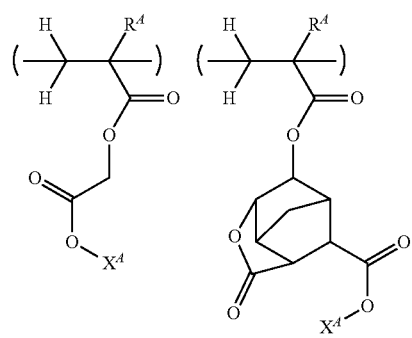

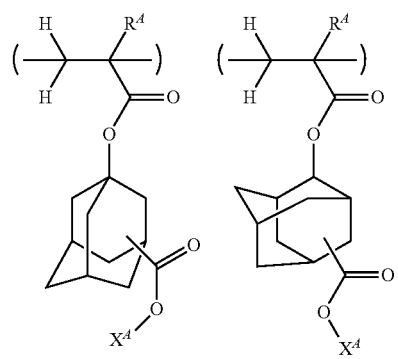

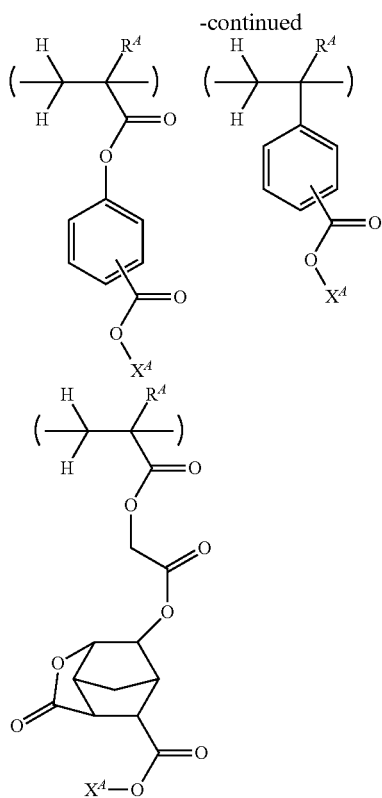

The acid labile group represented by $X^A$ may be selected from a variety of such groups. Examples of the acid labile group include $C_4$-$C_{40}$ tertiary alkyl groups, trialkylsilyl groups in which each alkyl moiety has 1 to 6 carbon atoms, and $C_4$-$C_{20}$ oxoalkyl groups. With respect to the structure of these acid labile groups, reference should be made to U.S. Pat. No. 9,164,384 (JP-A 2014-225005, paragraphs [0016]-[0035]).

Acid labile groups of the following formulae (xa) and (xb) are especially preferred.

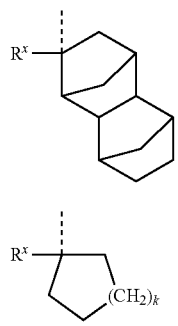

(xa)

(xb)

Herein $R^x$ is a $C_1$-$C_5$ straight or branched monovalent hydrocarbon group, and k is 1 or 2.

Preferably the base polymer contains polarity switch units of more than one type having acid labile groups of different structures. A resist composition comprising a base polymer containing polarity switch units having an acid labile group of formula (xa) and polarity switch units having an acid labile group of formula (xb) and a sulfonium salt having formula (1) is improved in lithography factors such as LWR.

Although the detail is not well understood, the following is presumed. When a tertiary alicyclic hydrocarbon group of formula (xa) or (xb) is bonded to the ester site, the group becomes more acid labile due to steric repulsion, than other chainlike tertiary alkyl groups, for example, tert-butyl and tert-pentyl. Also, as compared with an acid labile group having adamantane ring, the acid labile group of formula (xa) or (xb) allows for easy progress of acid-aided elimination reaction, tending to provide a high sensitivity. Therefore, when a tertiary alicyclic hydrocarbon group is incorporated in the polarity switch unit of the base polymer, the dissolution contrast between exposed and unexposed regions is increased. The cation in the sulfonium salt having formula (1) has a higher transmittance, but a lower acid generation efficiency than the triphenylsulfonium cation. Thus, for gaining satisfactory lithography performance, the polarity switch unit must have a high reactivity. For controlling the dissolution of exposed and unexposed regions, it is preferred to combine polarity switch units of more than one type having acid labile groups of formula (xa) or (xb). Now that acid labile groups of more than one type are incorporated, the timing of acid-aided elimination reactions slightly shifts, whereby the dissolution contrast at the boundary between exposed and unexposed regions is uniformed, leading to an improvement in LWR factor. As compared with the use of single polarity switch units, a combination of polarity switch units of more than one type which are different in lipophilicity enables to correct the profile of resist patterns.

Examples of the recurring unit having formula (a) are given below, but not limited thereto. Herein $R^A$ is as defined above.

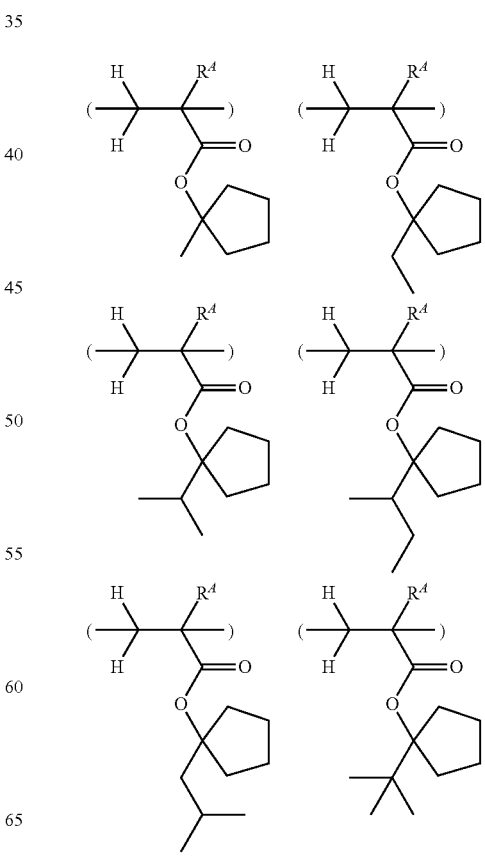

-continued
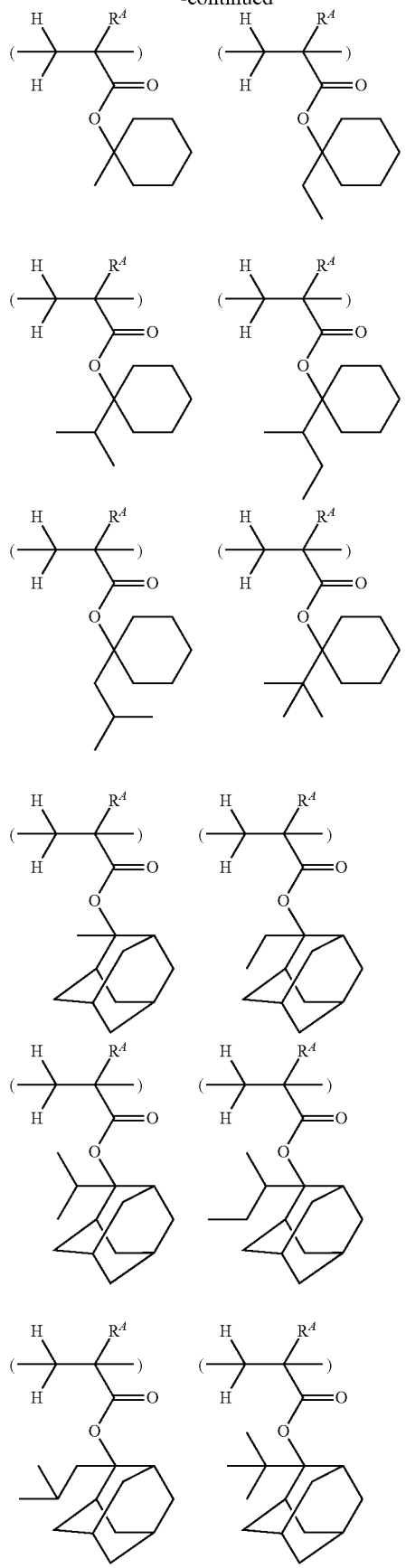
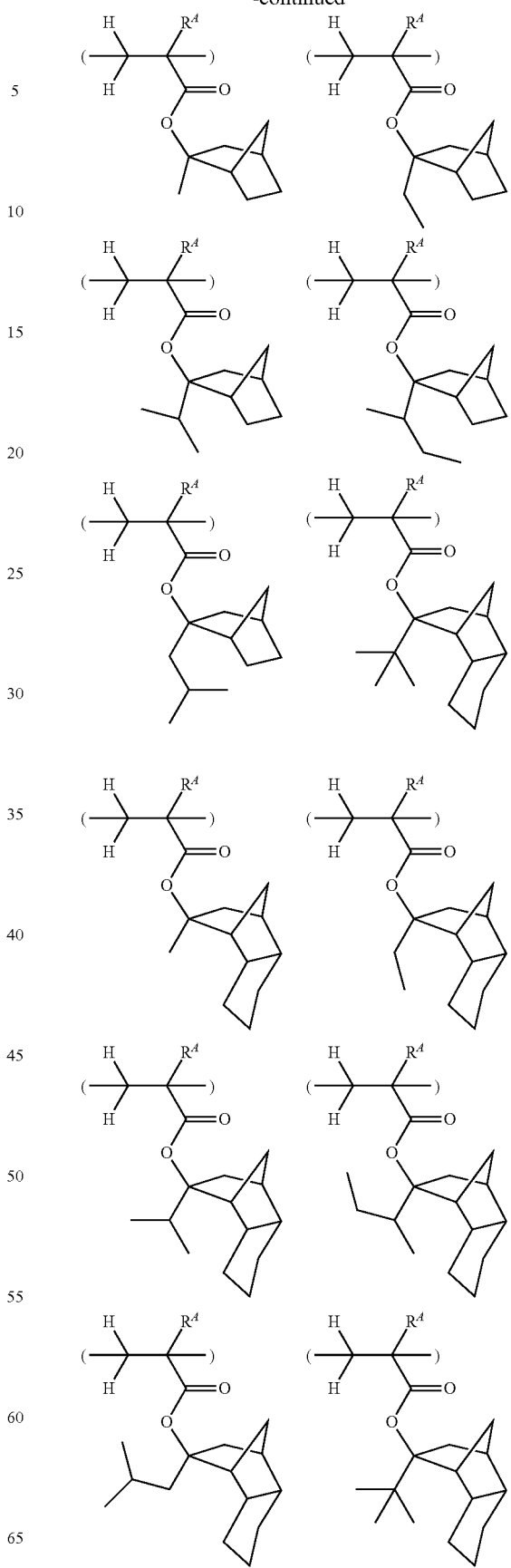

-continued
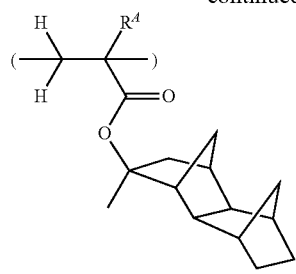
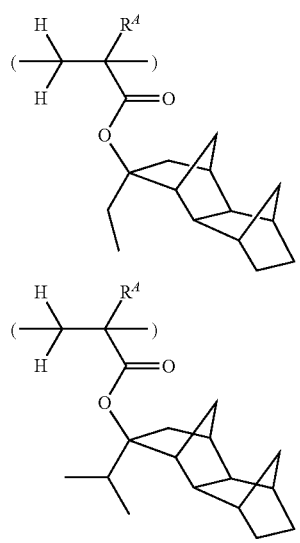
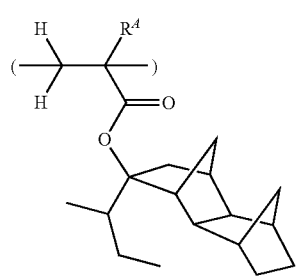
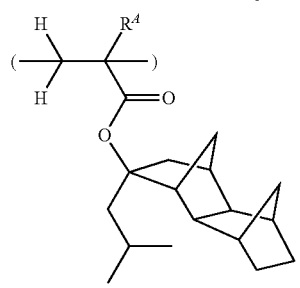
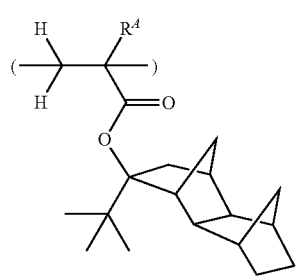
-continued
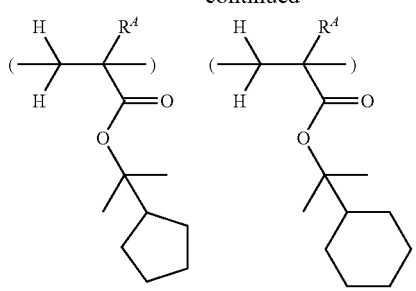
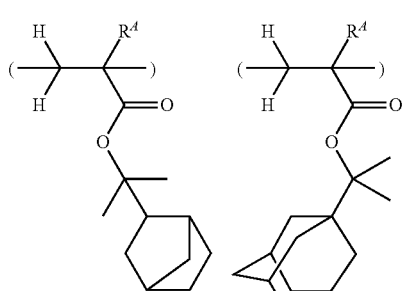
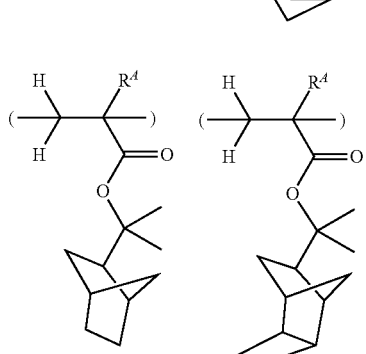
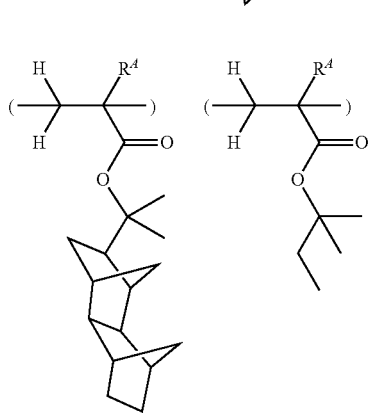
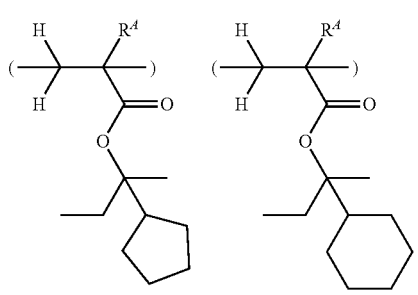

-continued
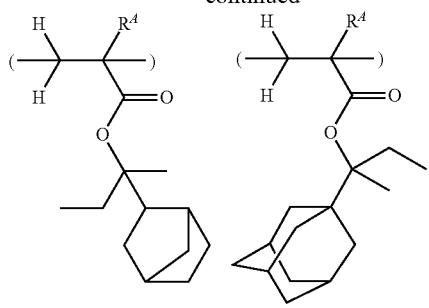
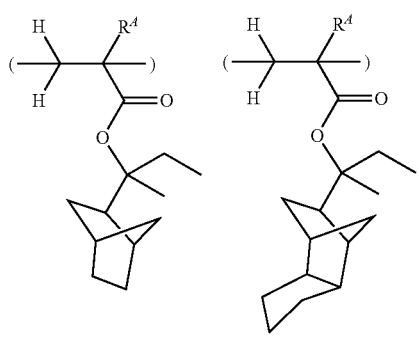
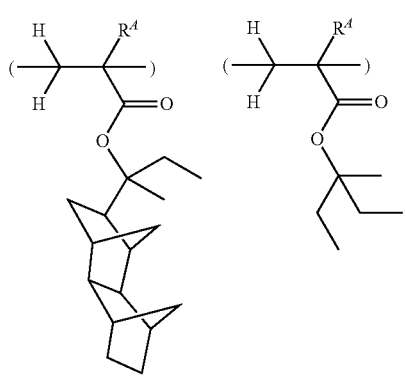
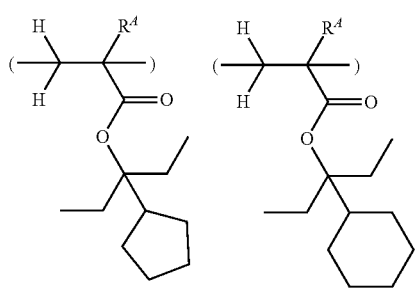
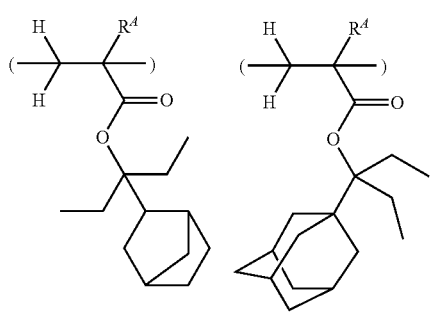
-continued
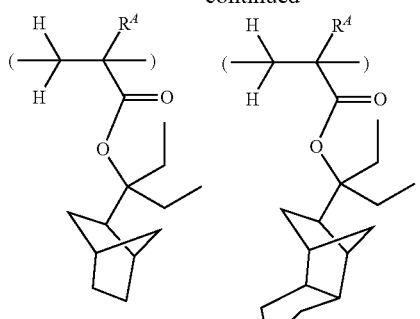
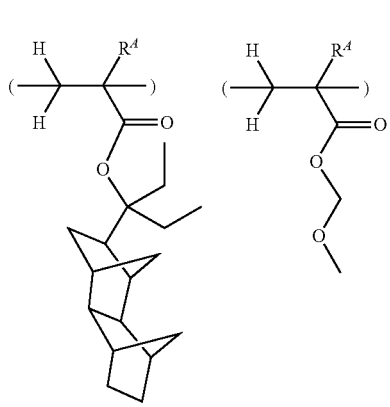
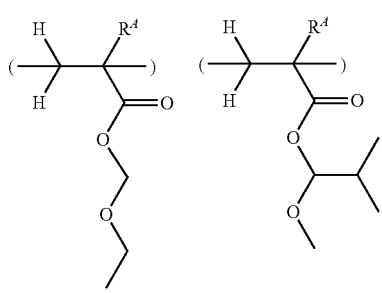
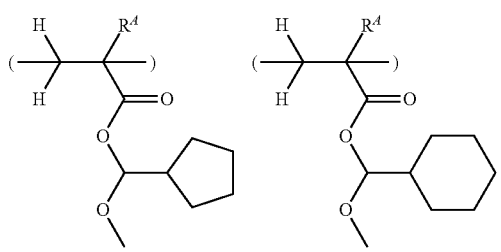
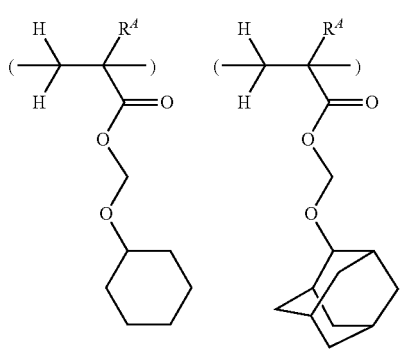

-continued

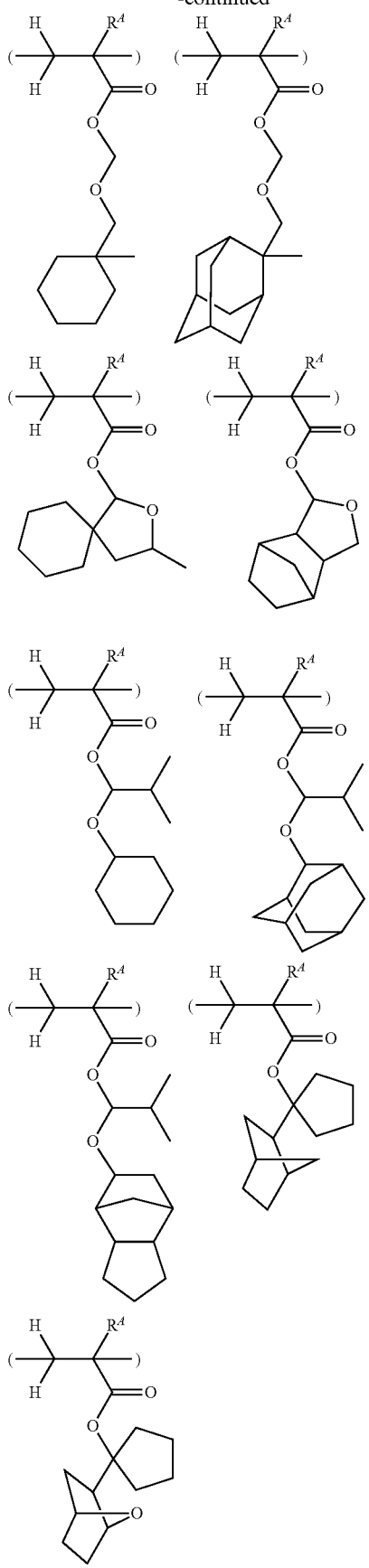

Although the above examples correspond to the unit having formula (a) wherein $Z^A$ is a single bond, combinations with similar acid labile groups are possible where $Z^A$ is other than a single bond. Groups of $Z^A$ other than a single bond are as shown above. Of the recurring units having formula (a), those units wherein $Z^A$ is a single bond and $X^A$ is an acid labile group of formula (xa) or (xb) are preferred.

Examples of the recurring unit having formula (b) are given below, but not limited thereto. Herein $R^A$ is as defined above.

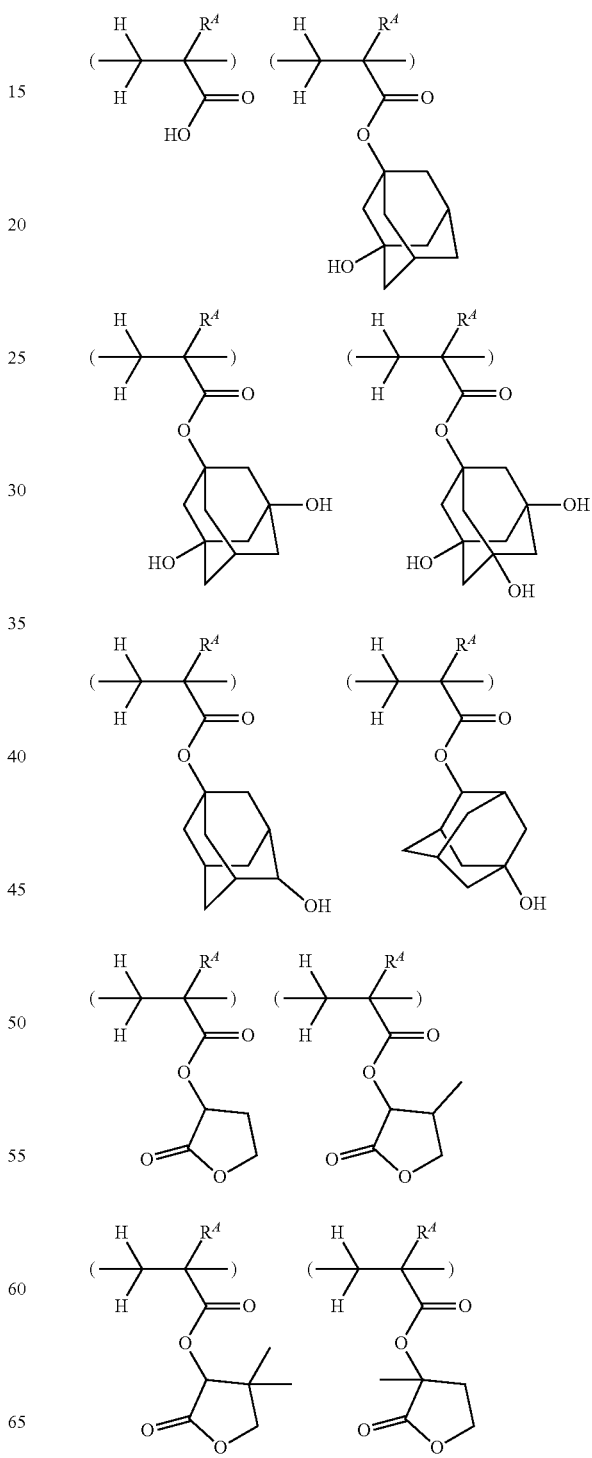

-continued
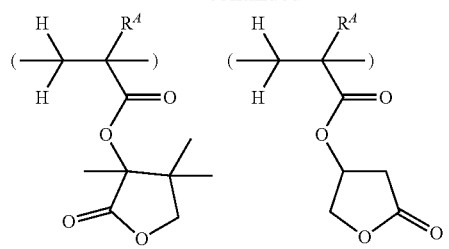
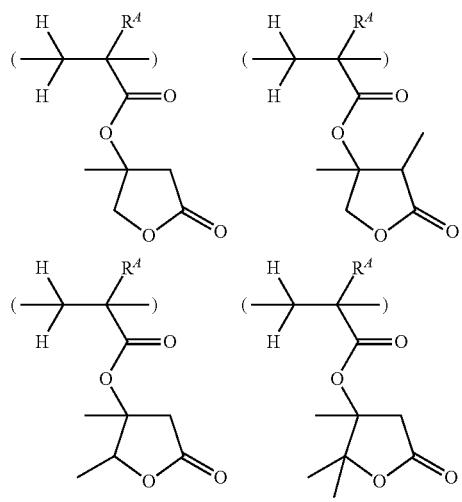
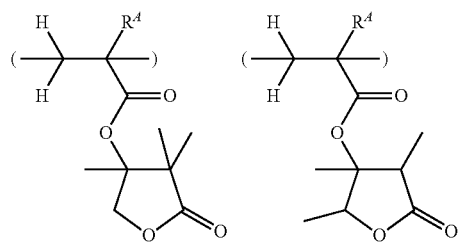
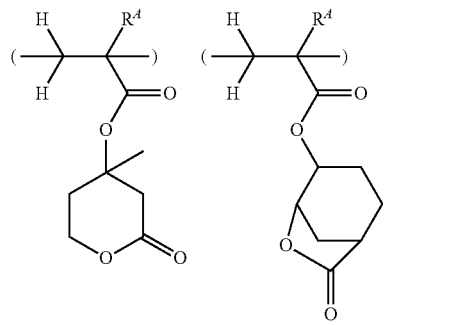
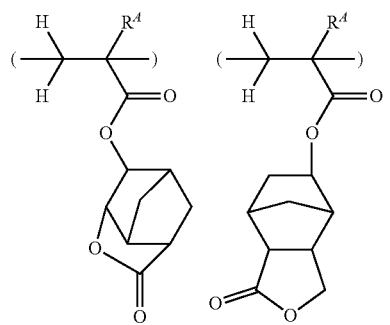
-continued
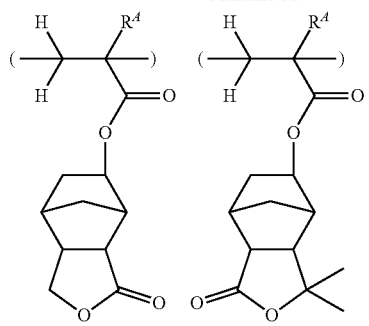
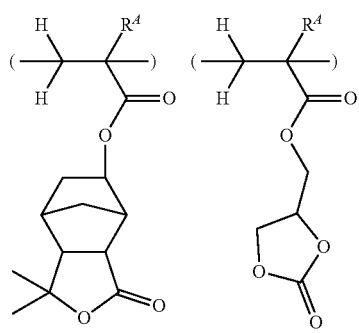
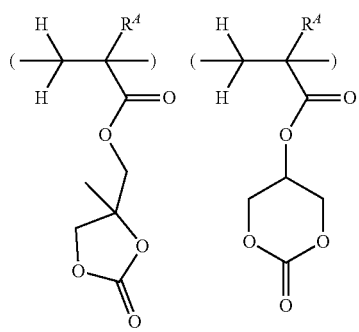
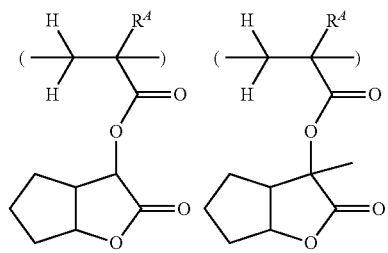
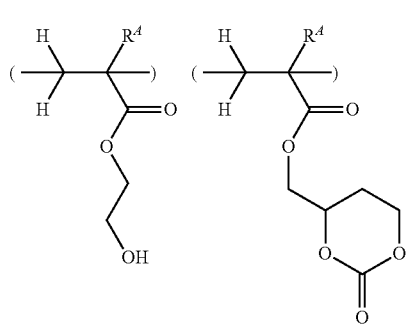

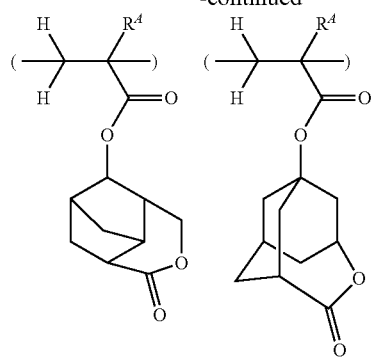
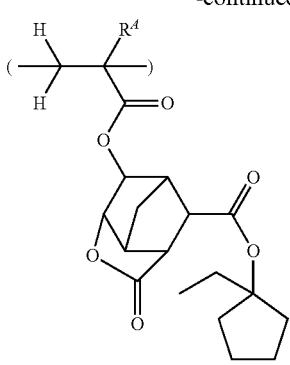
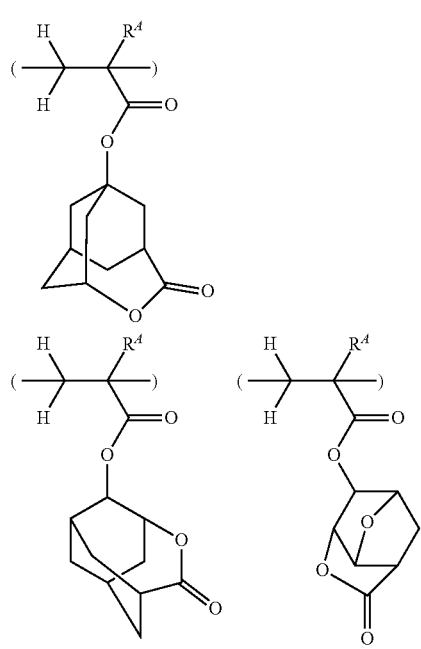
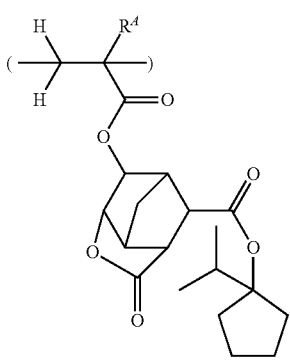
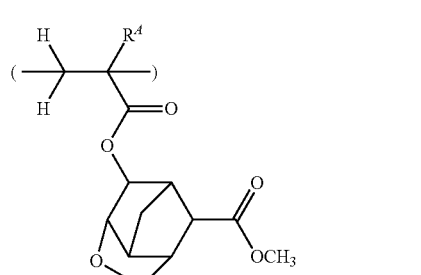
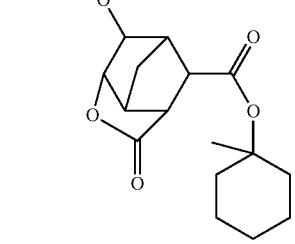
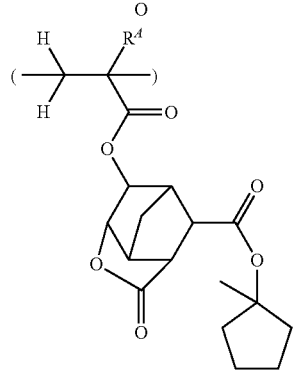
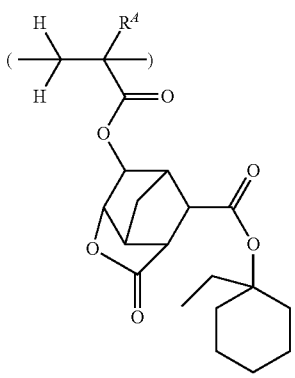

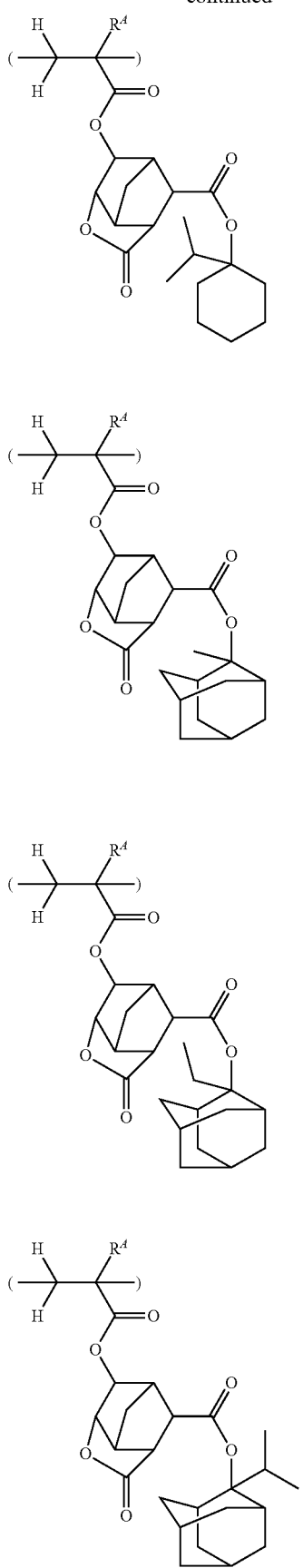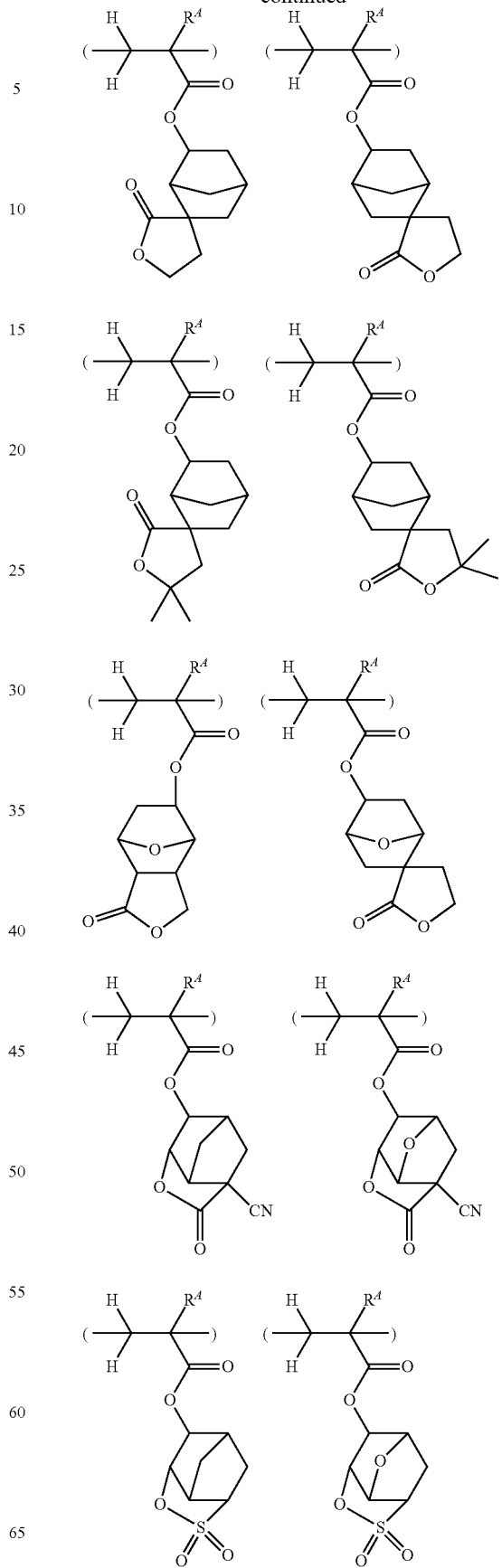

41
-continued
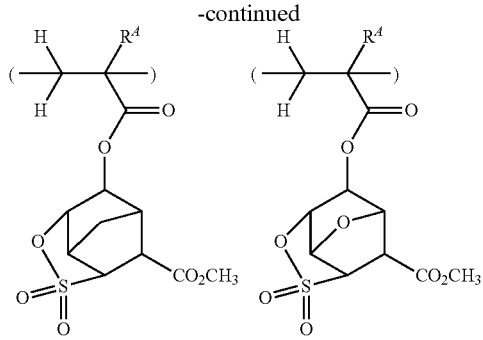
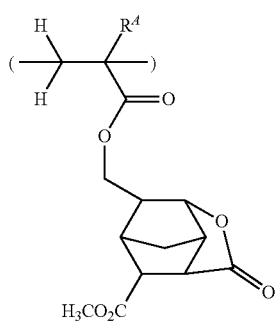
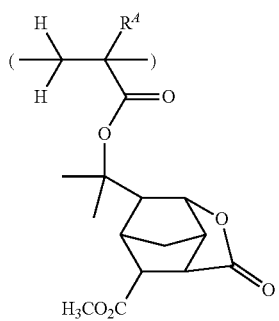
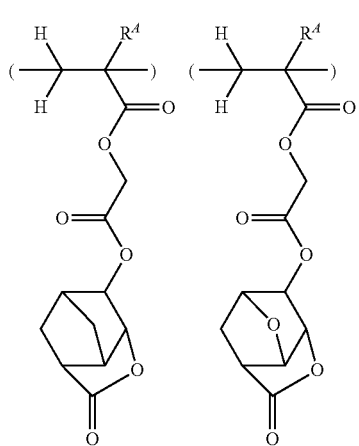
42
-continued
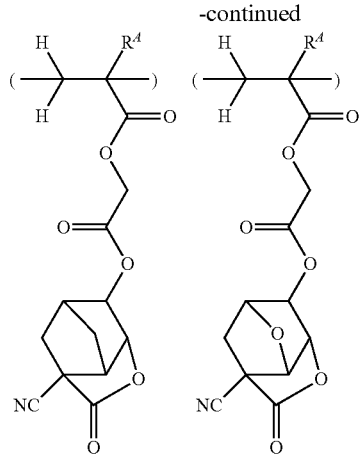
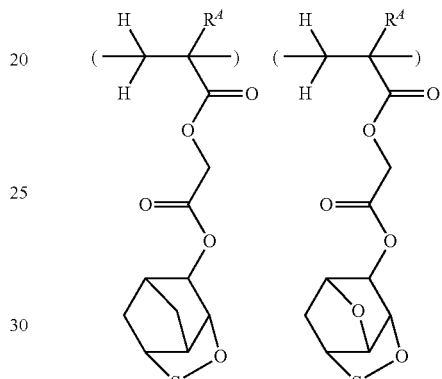
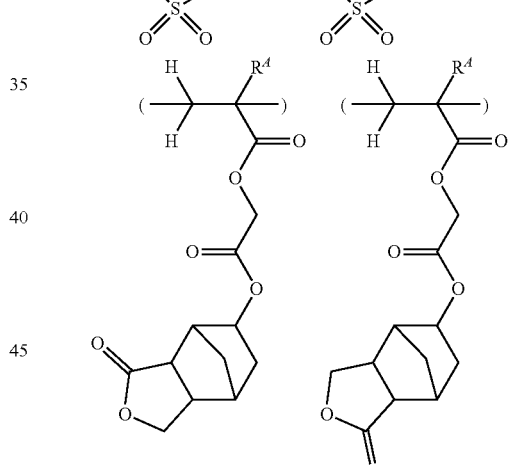
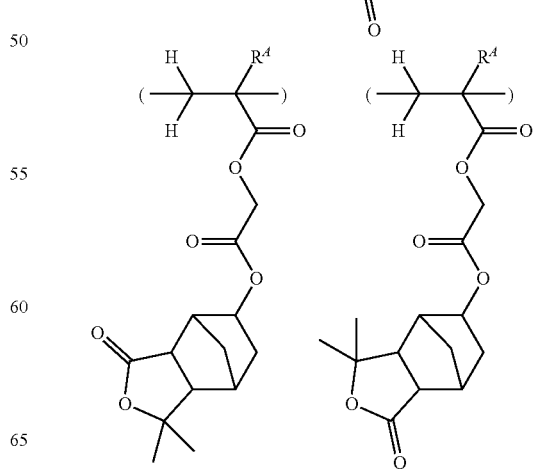

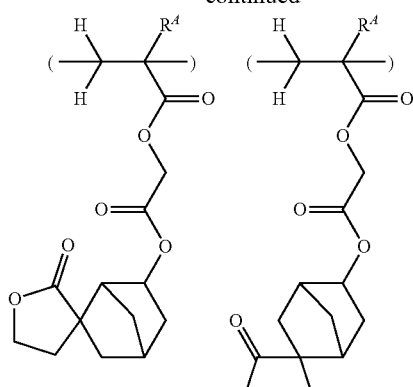
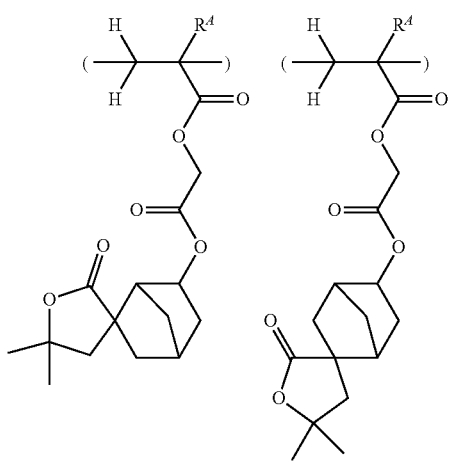
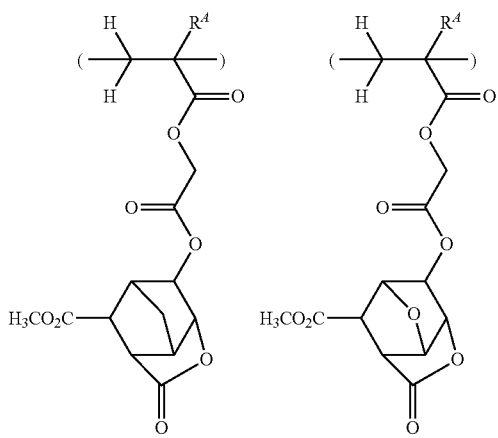
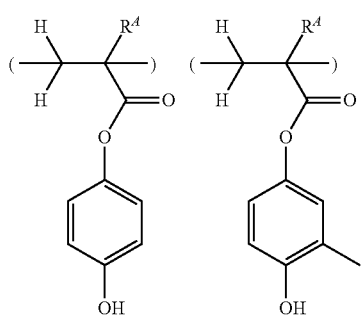
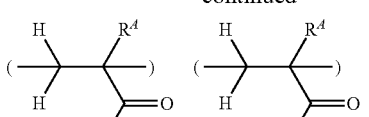
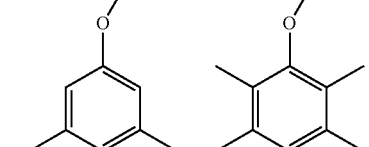
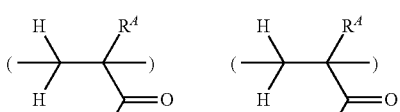
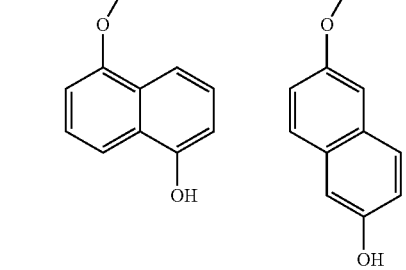
Of the recurring units having formula (b), recurring units having a hydroxyl group or lactone ring are preferred, and recurring units having 3-hydroxy-1-adamantyl (meth)acrylate or monocyclic lactone are more preferred. Exemplary recurring units are shown below.
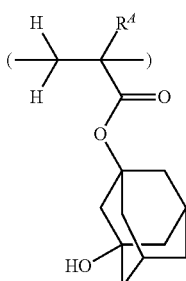
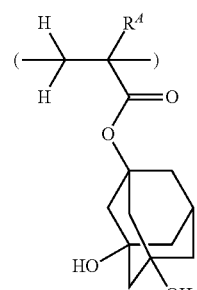
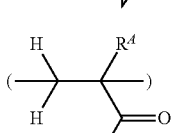
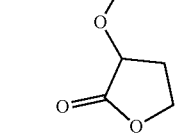
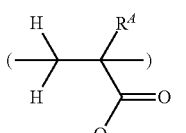
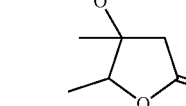

-continued

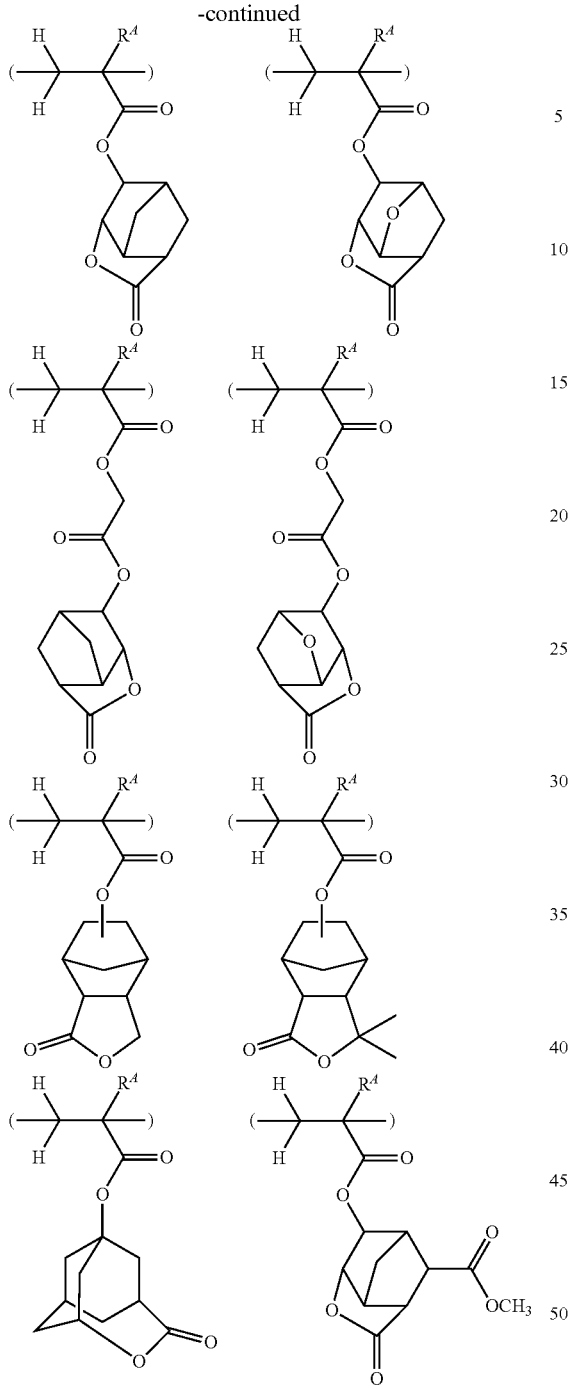

A resist composition comprising a base polymer containing polar units (b) of more than one type and a sulfonium salt having formula (1) is improved in lithography factors such as LWR. Although the detail is not well understood, the following is presumed. The use of two polar units having slightly different polarity allows for adequate control of acid diffusion, leading to improvements in lithography factors such as LWR. When monocyclic lactone units having a small volume are used, the volume change per molecule removed by development is smaller than in the case of fused ring lactone units, leading to improvements in lithography factors such as LWR and CDU. As mentioned above, the cation in the sulfonium salt having formula (1) has a high transmittance, but not a high acid generation efficiency, as compared with the triphenylsulfonium cation. Therefore, if high polarity units are used to suppress acid diffusion excessively, then sensitivity lowers, with the possibility of inducing defects and other faults. If polarity is too low, acid diffusion becomes substantial, probably degrading lithography factors. It is preferred to combine polarity units of more than one type in order to gain an adequate acid diffusion capability.

The base polymer may further comprise recurring units having the formula (c1), (c2), (c3) or (c4).

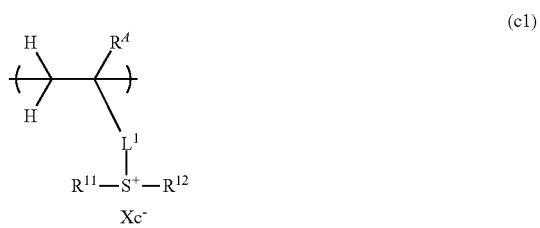

(c1)

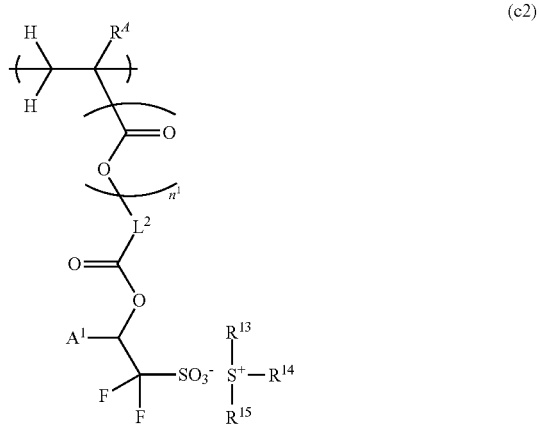

(c2)

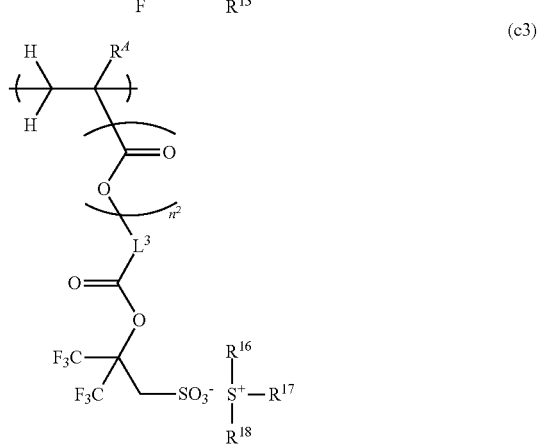

(c3)

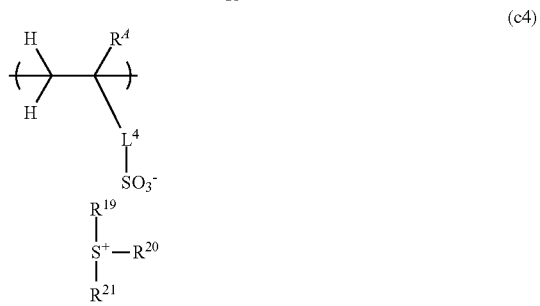

(c4)

In formulae (c1) to (c4), $R^4$ is hydrogen, fluorine, methyl or trifluoromethyl. $L^1$ is a single bond, phenylene, or —O-$L^{11}$, —C(=O)—O-$L^{11}$, —C(=O)—NH-$L^{11}$-, wherein $L^{11}$ is a $C_1$-$C_{20}$ alkanediyl group, $C_2$-$C_{20}$ alkenediyl group or phenylene group, which may contain a heteroatom. $L^2$ and $L^3$ are each independently a single bond or a $C_1$-$C_{20}$ divalent hydrocarbon group which may contain a heteroatom. $L^4$ is a single bond, methylene, ethylene, phenylene, fluorinated phenylene, —O-$L^{41}$-, —C(=O)—O-$L^{41}$- or —C(=O)—NH-$L^{41}$-, wherein $L^{41}$ is an optionally substituted phenylene group.

The alkanediyl group represented by $L^{11}$ may be straight, branched or cyclic. Examples thereof include methylene, ethane-1,1-diyl, ethane-1,2-diyl, propane-1,2-diyl, propane-2,2-diyl, propane-1,3-diyl, 2-methylpropane-1,3-diyl, butane-1,3-diyl, butane-2,3-diyl, butane-1,4-diyl, pentane-1,3-diyl, pentane-1,4-diyl, 2,2-dimethylpropane-1,3-diyl, pentane-1,5-diyl, hexane-1,6-diyl, cyclopentane-1,2-diyl, cyclopentane-1,3-diyl, cyclohexane-1,6-diyl, and adamantane-1,3-diyl. The alkenediyl group represented by $L^{11}$ may be straight, branched or cyclic, and examples thereof include ethene-1,2-diyl, 1-propene-1,3-diyl, 2-butene-1,4-diyl, 1-methyl-1-butene-1,4-diyl, and 2-cyclohexene-1,4-diyl.

The divalent hydrocarbon group represented by $L^2$ and $L^3$ may be straight, branched or cyclic, and examples thereof include alkanediyl and alkenediyl groups as exemplified above.

In formulae (c1) to (c4), $R^{11}$ to $R^{21}$ are each independently a $C_1$-$C_{20}$ monovalent hydrocarbon group which may contain a heteroatom. The monovalent hydrocarbon group may be straight, branched or cyclic. Examples include alkyl groups such as methyl, ethyl, n-propyl, isopropyl, n-butyl, and t-butyl, monovalent saturated cycloaliphatic hydrocarbon groups such as cyclopropyl, cyclopentyl, cyclohexyl, cyclopropylmethyl, 4-methylcyclohexyl, cyclohexylmethyl, norbornyl, and adamantyl, alkenyl groups such as vinyl, allyl, propenyl, butenyl, and hexenyl, monovalent unsaturated cycloaliphatic hydrocarbon groups such as cyclohexenyl, aryl groups such as phenyl and naphthyl, heteroaryl groups such as thienyl, and aralkyl groups such as benzyl, 1-phenylethyl and 2-phenylethyl. Inter alia, aryl groups are preferred. In these hydrocarbon groups, some hydrogen may be substituted by a moiety containing a heteroatom such as oxygen, sulfur, nitrogen or halogen, and some carbon may be replaced by a moiety containing a heteroatom such as oxygen, sulfur or nitrogen, so that the group may contain a hydroxyl moiety, cyano moiety, carbonyl moiety, ether bond, ester bond, sulfonic acid ester bond, carbonate bond, lactone ring, sultone ring, carboxylic anhydride or haloalkyl moiety. Among others, RH to $R^{21}$ are preferably phenyl groups or phenyl groups substituted with a heteroatom-containing moiety.

Any two of $L^1$, $R^{11}$ and $R^{12}$ may bond together to form a ring with the sulfur atom to which they are attached, any two of $R^{13}$, $R^{14}$ and $R^{15}$, any two of $R^{16}$, $R^{17}$ and $R^{18}$, or any two of $R^{19}$, $R^{20}$ and $R^{21}$ may bond together to form a ring with the sulfur atom to which they are attached.

In formula (c2), $A^1$ is hydrogen or trifluoromethyl.

In formula (c2), n1 is 0 or 1, $n^1$ is 0 when $L^2$ is a single bond. In formula (c3), $n^2$ is 0 or 1, $n^2$ is 0 when $L^3$ is a single bond.

In formula (c1), Xc⁻ is a non-nucleophilic counter ion. Examples of the non-nucleophilic counter ion include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl)imide and bis(perfluorobutylsulfonyl)imide; and methide ions such as tris(trifluoromethylsulfonyl)methide and tris(perfluoroethylsulfonyl)methide.

Other examples of the non-nucleophilic counter ion represented by Xc⁻ include anions having the formulae (c5) and (c6).

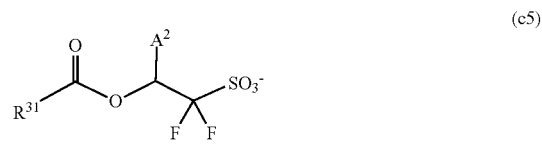

(c5)

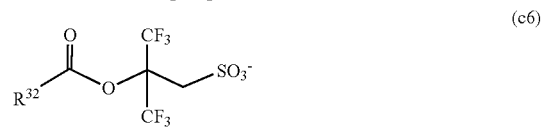

(c6)

In formulae (c5) and (c6), $R^{31}$ and $R^{32}$ are each independently a $C_1$-$C_{40}$ monovalent hydrocarbon group which may contain a heteroatom, and $A^2$ is hydrogen or trifluoromethyl.

Examples of the anion having formula (c5) include the anions exemplified for the anion in the sulfonium salt having formula (1) and the anions described in JP-A 2014-177407, paragraphs [0100]-[0101]. Examples of the anion having formula (c6) include the anions described in JP-A 2010-215608, paragraphs [0080]-[0081] and the anions shown below.

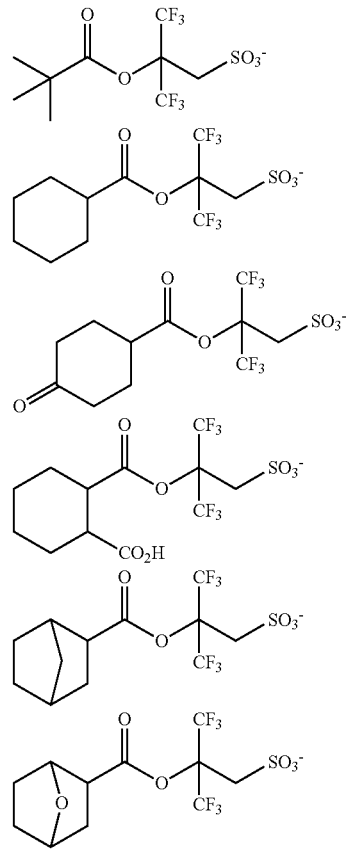

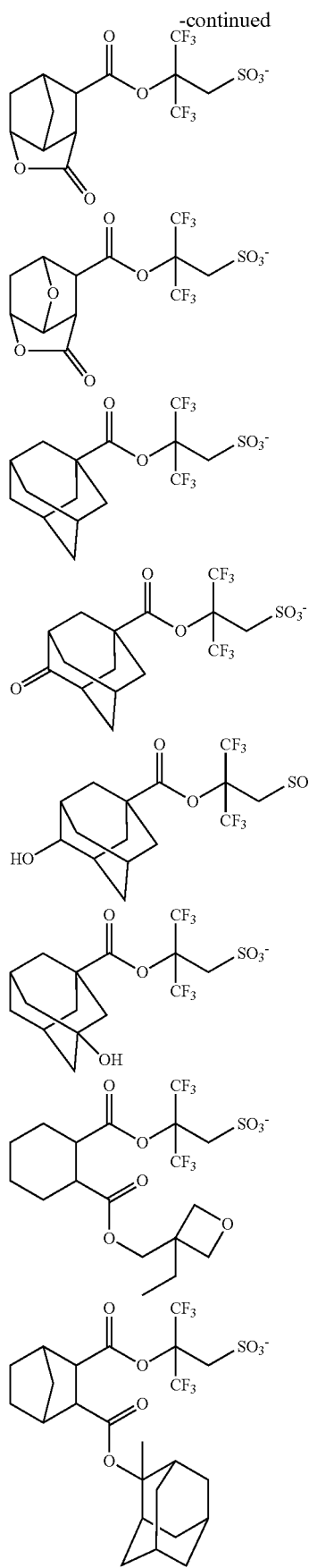
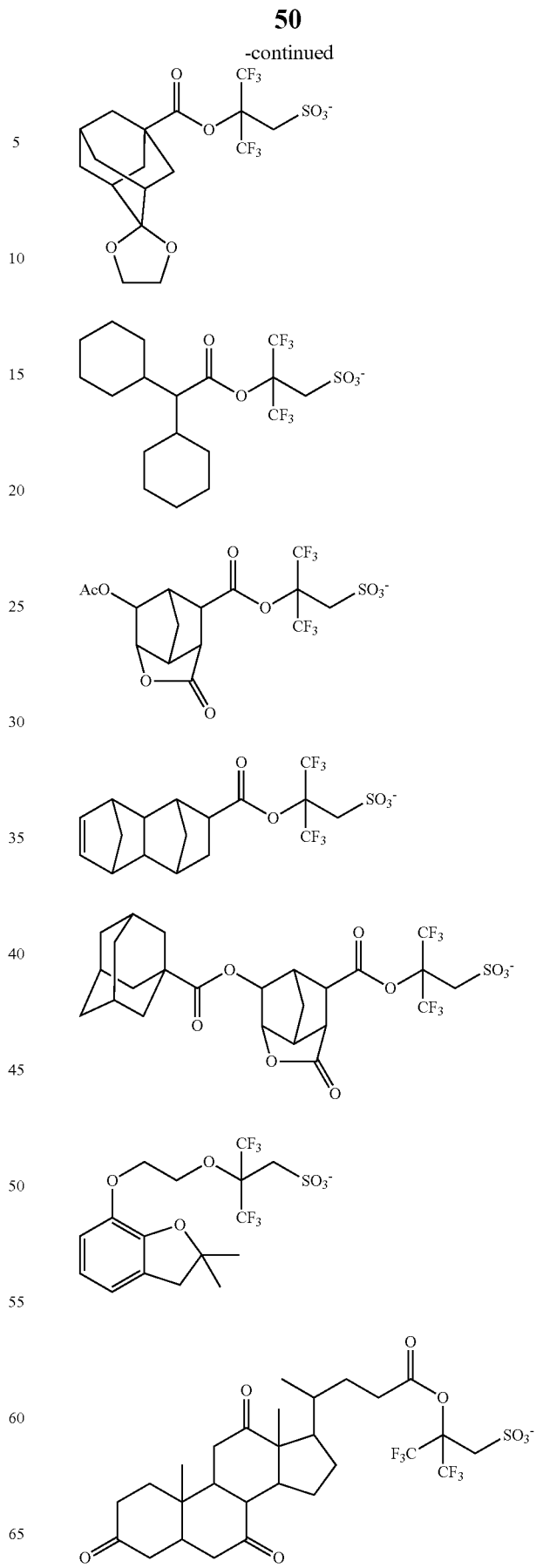

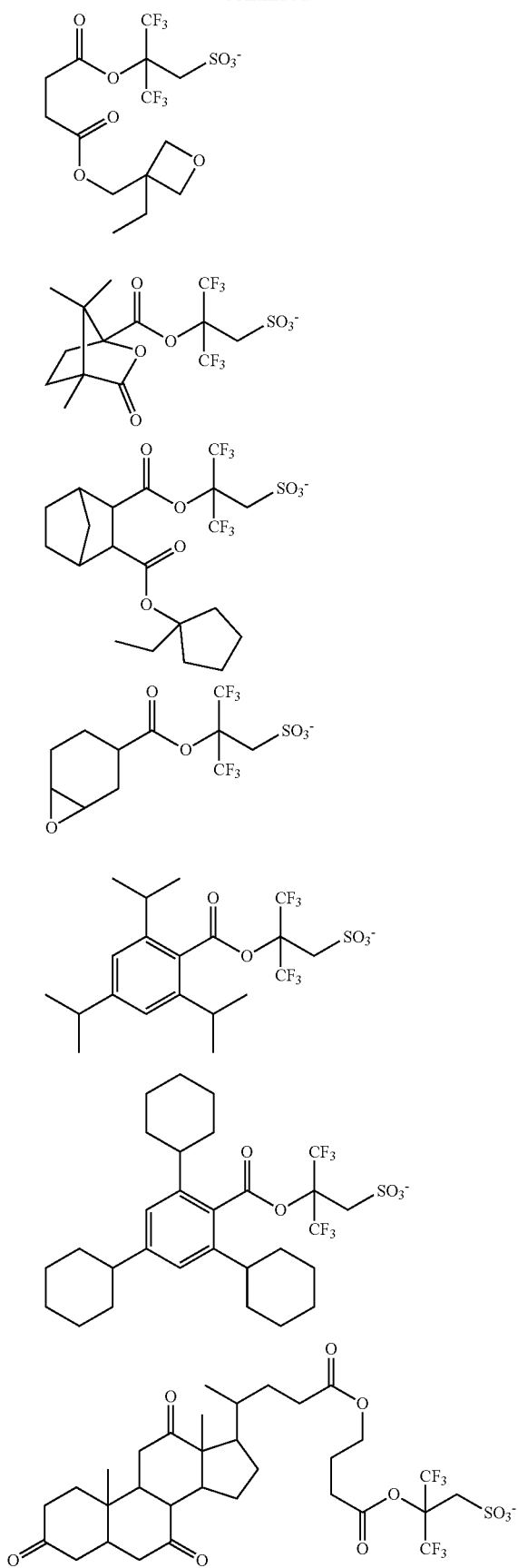

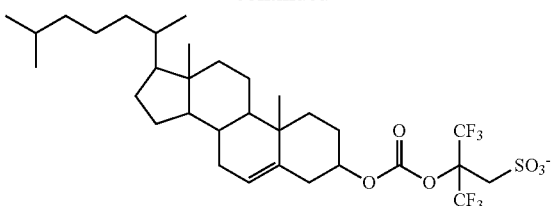

Exemplary structures of the anion moiety in formula (c2) are as described in JP-A 2014-177407, paragraphs [0021]-[0026]. Exemplary structures of the anion moiety in formula (c2) wherein $A^1$ is hydrogen are as described in JP-A 2010-116550, paragraphs [0021]-[0028]. Exemplary structures of the anion moiety in formula (c2) wherein $A^1$ is trifluoromethyl are as described in JP-A 2010-077404, paragraphs [0021]-[0027].

Exemplary structures of the anion moiety in formula (c3) include the exemplary structures of the anion moiety in formula (c2) wherein —CH($A^1$)CF$_2$SO$_3^-$ is replaced by —C(CF$_3$)$_2$CH$_2$SO$_3^-$.

Examples of the sulfonium cation in formulae (c2) to (c4) include the cations described in JP-A 2008-158339, paragraph [0223] and the cations shown below.

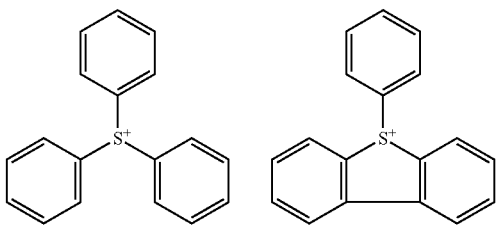

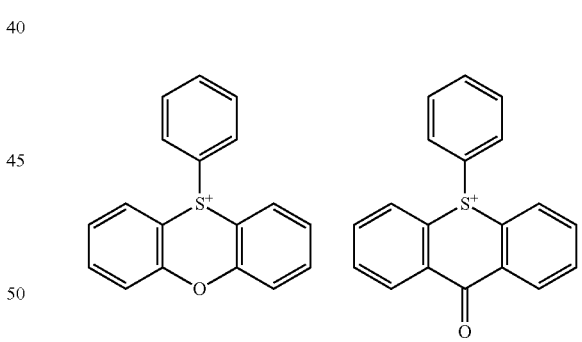

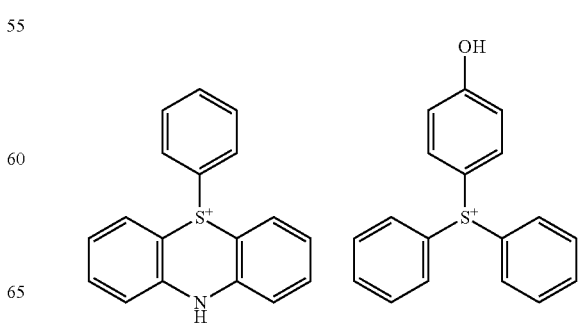

-continued

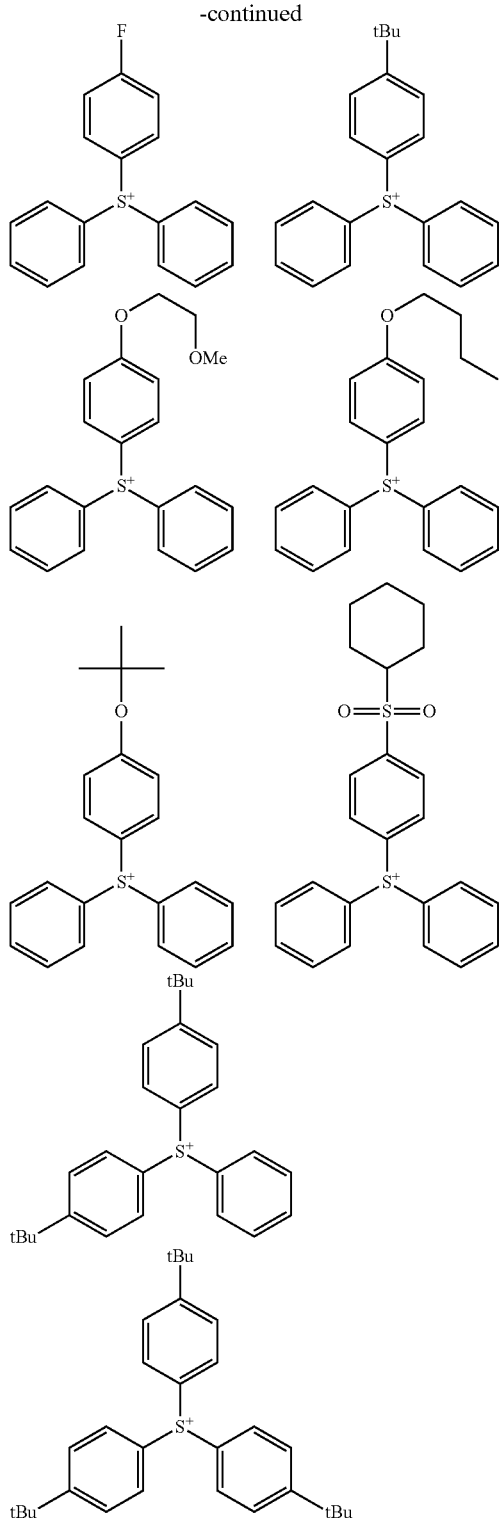

The base polymer may further comprise recurring units of the structure having a hydroxyl group protected with an acid labile group. The recurring unit of the structure having a hydroxyl group protected with an acid labile group is not particularly limited as long as the unit has at least one protected hydroxyl structure wherein a hydroxyl group is resumed as a result of decomposition of the protective group under the action of acid. Such recurring units are described in JP-A 2014-225005, paragraphs [0055]-[0065] and JP-A 2015-214634, paragraphs [0110]-[0115].

The polymer may further comprise other recurring units. Typical of the other recurring units are recurring units having an oxirane or oxetane ring. A polymer comprising recurring units having an oxirane or oxetane ring is cross-linked in exposed regions, leading to improvements in retention and etching resistance of a resist film in exposed regions.

The polymer may further comprise still other recurring units, for example, units derived from substituted acrylates such as methyl methacrylate, methyl crotonate, dimethyl maleate, and dimethyl itaconate, unsaturated carboxylic acids such as maleic acid, fumaric acid, and itaconic acid, cyclic olefins such as norbornene, norbornene derivatives, tetracyclo[6.2.1.1$^{3,6}$.0$^{2,7}$]dodecene derivatives, unsaturated acid anhydrides such as itaconic anhydride, vinyl aromatics such as styrene, hydroxystyrene, acetoxystyrene, tert-butoxystyrene, vinylnaphthalene, and hydroxyvinylnaphthalene, and other monomers. Examples of the other recurring units are described in JP-A 2015-214634, paragraphs [0120]-[0132].

The base polymer should preferably have a Mw of 1,000 to 500,000, more preferably 3,000 to 100,000, and even more preferably 4,000 to 20,000. A Mw within the range eliminates any risks including an extreme drop of etching resistance, a failure to gain a difference in dissolution rate before and after exposure, and a lowering of resolution.

As used herein, Mw is measured versus polystyrene standards by GPC using tetrahydrofuran (THF) solvent. Also preferably the polymer has a dispersity (Mw/Mn) of 1.2 to 2.5, more preferably 1.3 to 1.8.

The polymer may be synthesized by any method, for example, by using one or more monomers corresponding to the desired recurring units in an organic solvent, adding a radical polymerization initiator, and heating for polymerization. For the polymerization method, reference should be made to U.S. Pat. No. 9,256,127 (JP-A 2015-214634, paragraphs [0134]-[0137]). The acid labile group that has been incorporated in the monomer may be kept as such, or polymerization may be followed by protection or partial protection.

While the base polymer comprises recurring units derived from monomers, the molar fractions of respective units preferably fall in the following range (mol %), but are not limited thereto:

(I) 10 to 80 mol %, more preferably 20 to 70 mol %, even more preferably 30 to 60 mol % of recurring units of at least one type having formula (a), (II) 20 to 90 mol %, more preferably 30 to 80 mol %, even more preferably 40 to 70 mol % of recurring units of at least one type having formula (b), and optionally, (III) 0 to 30 mol %, more preferably 0 to 20 mol %, and even more preferably 0 to 15 mol % of recurring units of at least one type selected from formulae (c1) to (c4), and optionally, (IV) 0 to 80 mol %, more preferably 0 to 70 mol %, and even more preferably 0 to 50 mol % of recurring units of at least one type derived from another monomer(s).

The base polymer may be used alone or in a combination of two or more polymers which are different in compositional ratio, Mw and/or Mw/Mn. In addition to the polymer, a hydrogenated product of ring-opening metathesis polymerization (ROMP) polymer may be used. The hydrogenated ROMP polymer is as described in JP-A 2003-066612.

(C) Organic Solvent

Any organic solvent may be used as component (C) insofar as the foregoing components and other additives are soluble therein. Examples of the organic solvent are described in JP-A 2008-111103, paragraphs [0144]-[0145] (U.S. Pat. No. 7,537,880). Specifically, exemplary solvents include ketones such as cyclohexanone (CyHO) and methyl-2-n-pentyl ketone; alcohols such as 3-methoxybutanol, 3-methyl-3-methoxybutanol, 1-methoxy-2-propanol, 1-ethoxy-2-propanol and diacetone alcohol; ethers such as propylene glycol monomethyl ether (PGME), ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone (GBL), and mixtures thereof. Where an acid labile group of acetal form is used, a high-boiling alcohol solvent such as diethylene glycol, propylene glycol, glycerol, 1,4-butanediol or 1,3-butanediol may be added for accelerating deprotection reaction of acetal.

Of the above organic solvents, it is recommended to use 1-ethoxy-2-propanol, PGMEA, CyHO, GBL, and mixtures thereof because the acid generator is most soluble therein.

An appropriate amount of the organic solvent (C) used is 100 to 8,000 parts, more preferably 400 to 6,000 parts by weight per 80 parts by weight of the base polymer (B).

(D) Other Photoacid Generator

The resist composition may comprise (D) a photoacid generator other than the sulfonium salt having formula (1). The other PAG may be any compound capable of generating an acid upon exposure to high-energy radiation. Suitable PAGs include sulfonium salts, iodonium salts, sulfonyldiazomethanes, N-sulfonyloxydicarboxyimides, O-arylsulfonyloximes, and O-alkylsulfonyloximes, which may be used alone or in admixture. Suitable examples are described in JP-A 2007-145797, paragraphs [0102]-[0113], JP-A 2008-111103, paragraphs [0122]-[0142], JP-A 2014-001259, paragraphs [0081]-[0092], JP-A 2012-041320, JP-A 2012-153644, JP-A 2012-106986, and JP-A 2016-018007. The PAGs capable of generating partially fluorinated sulfonic acids described in the foregoing patent documents are preferably used in a resist composition because the strength and diffusion length of the generated acid are appropriate when the resist composition is applied to the ArF lithography.

Compounds having the formula (2) are also preferred as the PAG (D).

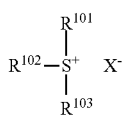

(2)

In formula (2), $R^{101}$, $R^{102}$ and $R^{103}$ are each independently a $C_6$-$C_{20}$ aryl group which may contain a heteroatom. Any two of $R^{101}$, $R^{102}$ and $R^{103}$ may bond together to form a ring with the sulfur atom to which they are attached.

The sulfonium cation in formula (2) is described in JP-A 2014-001259, paragraphs [0082]-[0085]. Exemplary cations are described in JP-A 2007-145797, paragraphs [0027]-[0033], JP-A 2010-113209, paragraph [0059], JP-A 2012-041320, JP-A 2012-153644, and JP-A 2012-106986.

Preferred examples of the sulfonium cation in formula (2) are shown below.

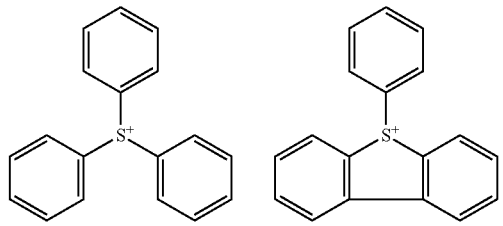

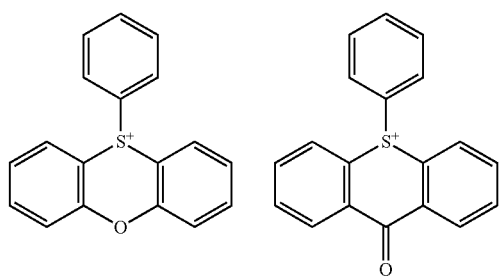

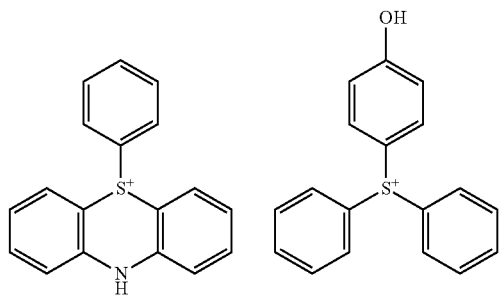

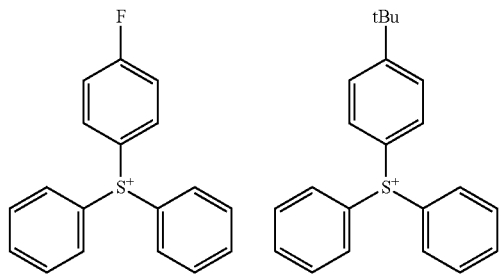

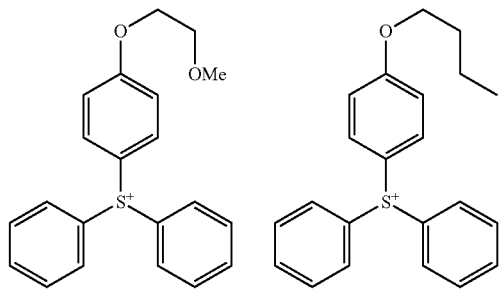

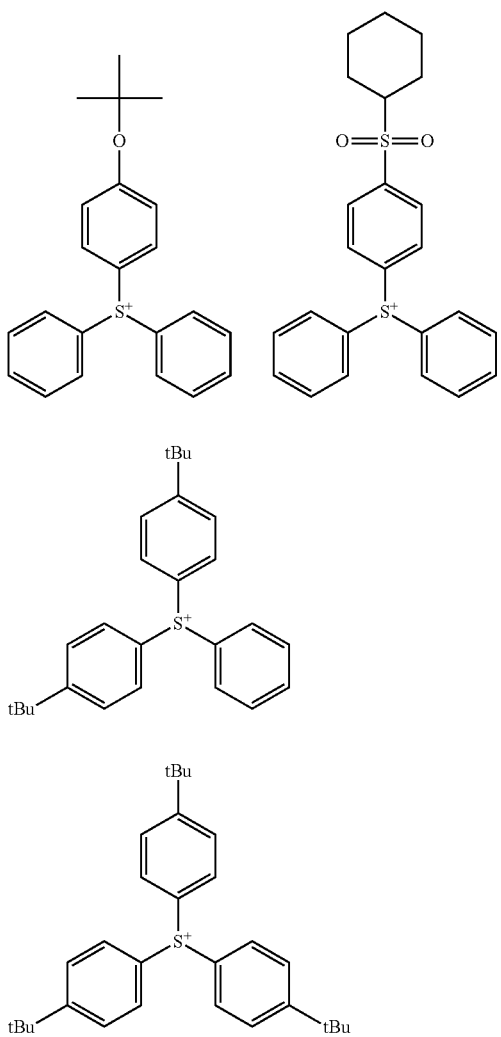

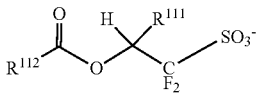

(2A')

In formula (2A'), $R^{111}$ is hydrogen or trifluoromethyl, preferably trifluoromethyl. $R^{112}$ is a $C_1$-$C_{35}$ monovalent hydrocarbon group which may contain a heteroatom. For the anion having formula (2A), reference is made to JP-A 2007-145797, JP-A 2008-106045, JP-A 2009-007327, JP-A 2009-258695, and JP-A 2012-181306. Suitable examples include the anions described in these patent documents and the examples described above for the anion in the salt having formula (1).

In formula (2B), $R^{fb}$ is a $C_1$-$C_{40}$ monovalent hydrocarbon group which may contain a heteroatom. The monovalent hydrocarbon group may be straight, branched or cyclic. Examples thereof are as exemplified for $R^2$ in formula (1).

The anion of formula (2B) is described in JP-A 2010-215608 and JP-A 2014-133723, and examples thereof include the anions described in these patent documents and the examples described for the anion having formula (c6). The compound having the anion of formula (2B) does not have fluorine at the α-position relative to the sulfo group, but two trifluoromethyl groups at the n-position. For this reason, it has a sufficient acidity to sever the acid labile groups in the resist polymer. Thus the compound is an effective PAG.

As the anion in the PAG (D), the preferred structures are shown below, but not limited thereto. Herein $A^3$ is hydrogen or trifluoromethyl.

Of these, triphenylsulfonium and (4-tert-butylphenyl)diphenylsulfonium cations are especially preferred.

In formula (2), X⁻ is an anion having the formulae (2A) or (2B).

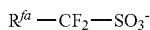

(2A)

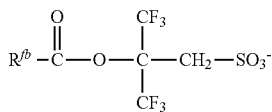

(2B)

In formula (2A), $R^{fa}$ is fluorine, a $C_1$-$C_4$ perfluoroalkyl group, or a $C_1$-$C_{40}$ monovalent hydrocarbon group which may contain a heteroatom. The monovalent hydrocarbon group may be straight, branched or cyclic and examples thereof are as exemplified above for $R^2$ in formula (1).

Of the anions having formula (2A), trifluoromethanesulfonate and nonafluorobutanesulfonate anions and anions having the formula (2A') are preferred.

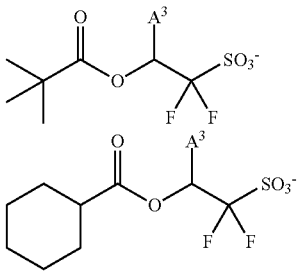

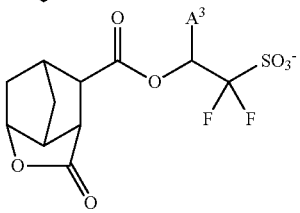

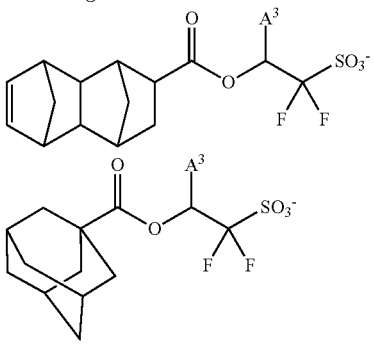

-continued
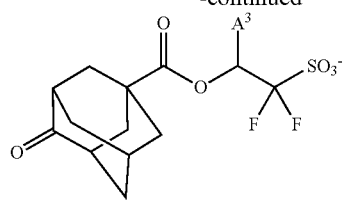
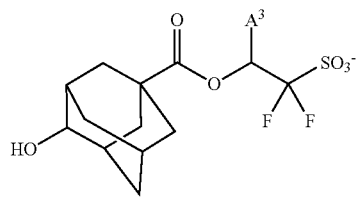
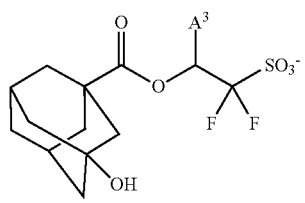
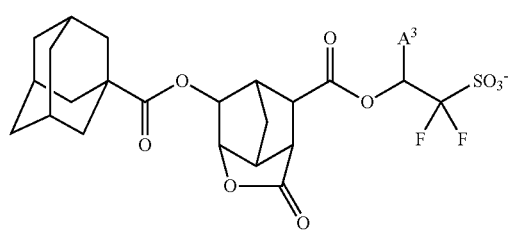
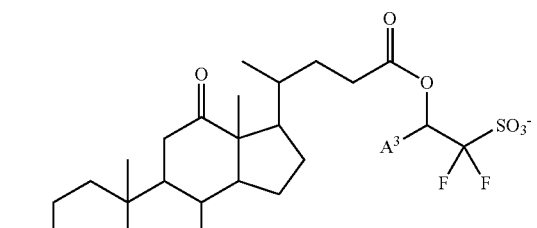
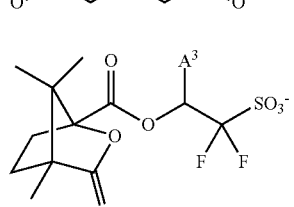
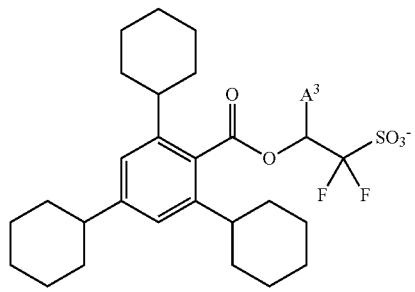
-continued
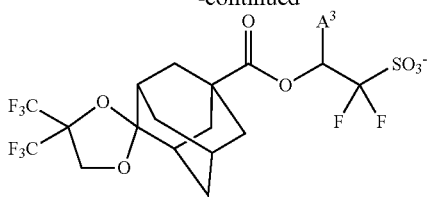
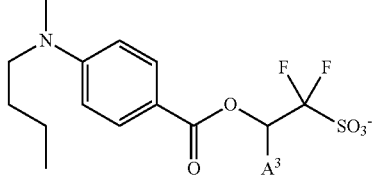
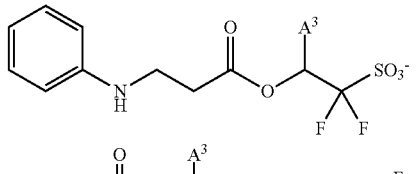
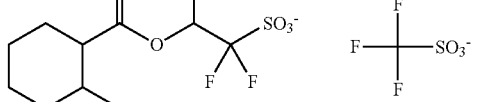
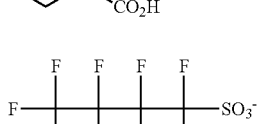
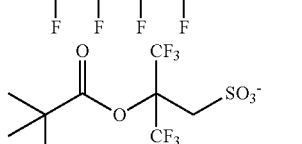
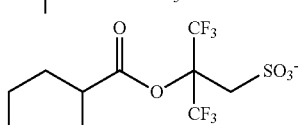
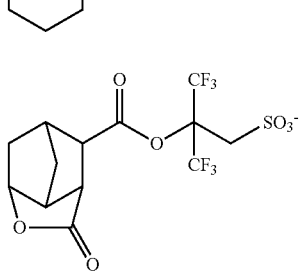
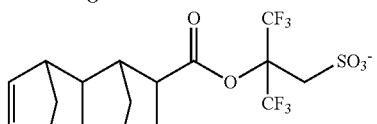
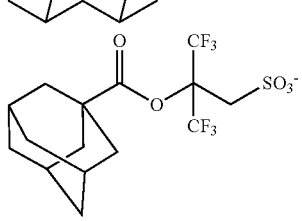

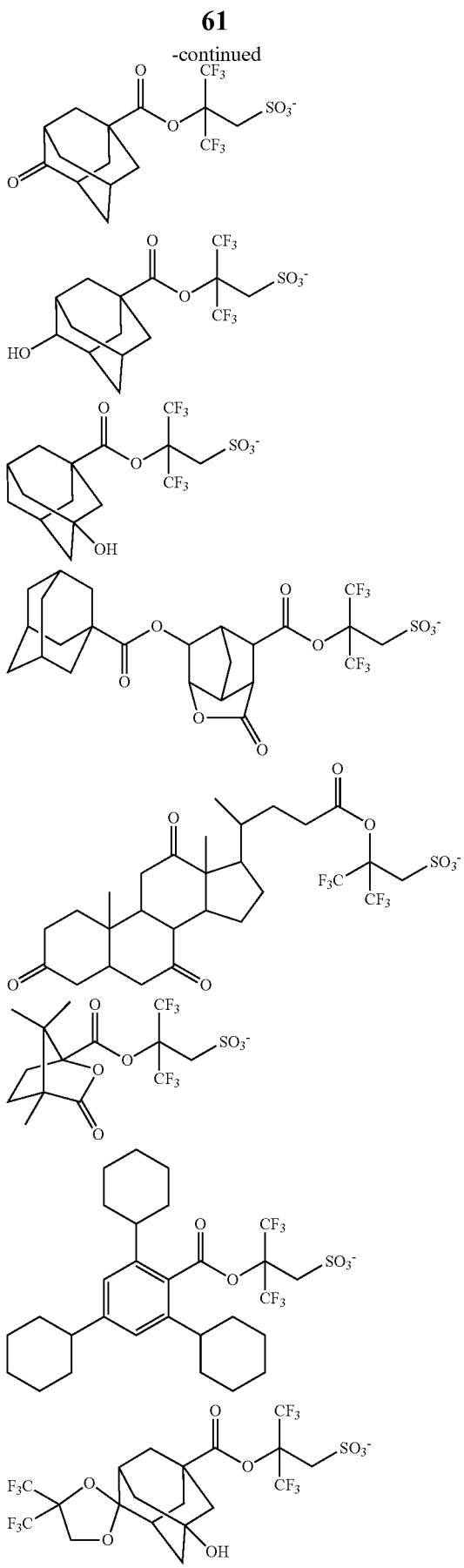

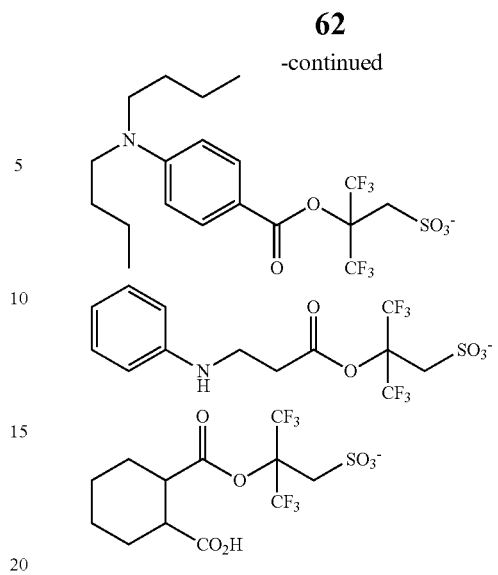

Structural examples of the compound having formula (2) include arbitrary combinations of cations with anions, both as exemplified above, but are not limited thereto.

Another preferred PAG (D) is a compound having the formula (3).

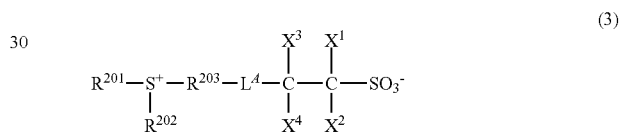

In formula (3), $R^{201}$ and $R^{202}$ are each independently a $C_1$-$C_{30}$ monovalent hydrocarbon group which may contain a heteroatom. $R^{203}$ is a $C_1$-$C_{30}$ divalent hydrocarbon group which may contain a heteroatom. Any two of $R^{201}$, $R^{202}$ and $R^{203}$ may bond together to form a ring with the sulfur atom to which they are attached. $L^4$ is a single bond, ether bond or a $C_1$-$C_{20}$ divalent hydrocarbon group which may contain a heteroatom. $X^1$, $X^2$, $X^3$ and $X^4$ are each independently hydrogen, fluorine or trifluoromethyl, with the proviso that at least one of $X^1$, $X^2$, $X^3$ and $X^4$ is fluorine or trifluoromethyl.

The monovalent hydrocarbon group represented by $R^{201}$ and $R^{202}$ may be straight, branched or cyclic and examples thereof are as exemplified above for $R^2$ in formula (1). The divalent hydrocarbon group represented by $R^{203}$ may be straight, branched or cyclic and examples thereof include the monovalent hydrocarbon groups exemplified above for $R^2$ in formula (1), with one hydrogen being eliminated therefrom.

Among the compounds having formula (3), compounds having the formula (3') are more preferred.

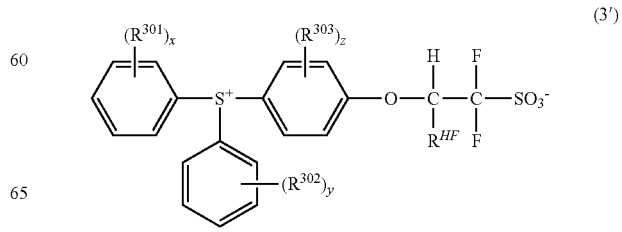

In formula (3'), R is hydrogen or trifluoromethyl, preferably trifluoromethyl. $R^{301}$, $R^{302}$ and $R^{303}$ are each independently hydrogen or a $C_1$-$C_{20}$ monovalent hydrocarbon group which may contain a heteroatom. The monovalent hydrocarbon group may be straight, branched or cyclic and examples thereof are as exemplified above for $R^2$ in formula (1). The subscripts x and y are each independently an integer of 0 to 5, and z is an integer of 0 to 4.

The PAGs having formula (3) or (3') are described in JP-A 2011-016746. Examples include the sulfonium compounds described in JP-A 2011-016746 and the sulfonium compounds described in JP-A 2015-214634, paragraphs [0149]-[0150].

Preferred examples of the compound having formula (3) are shown below, but not limited thereto. Herein $R^{HF}$ is as defined above.

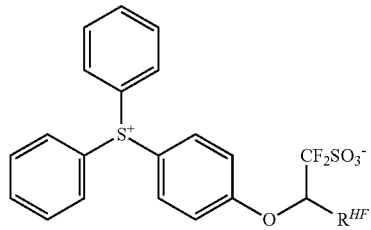

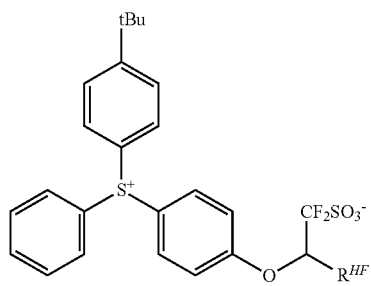

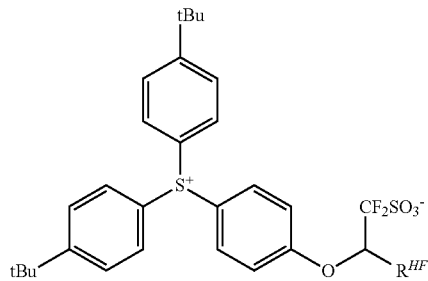

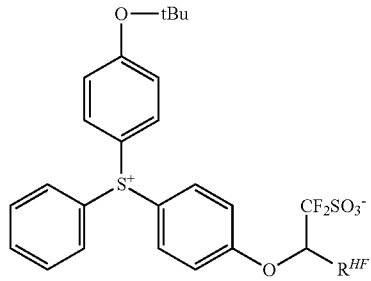

-continued

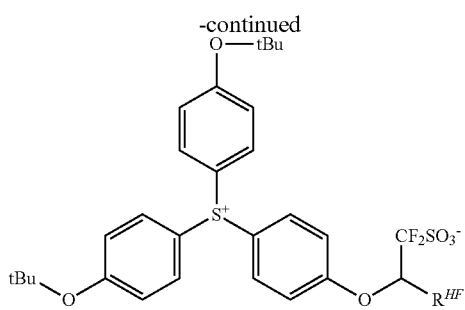

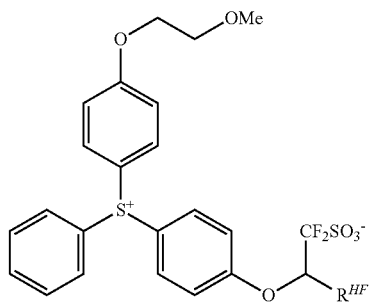

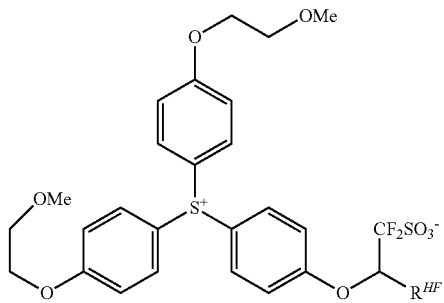

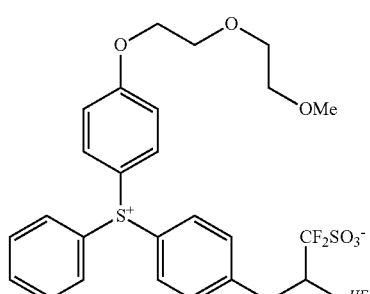

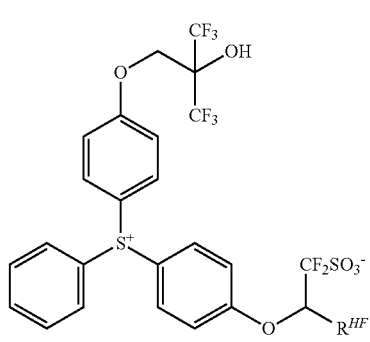

-continued

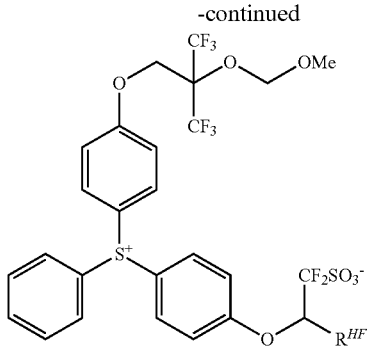

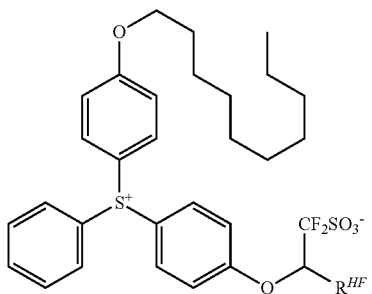

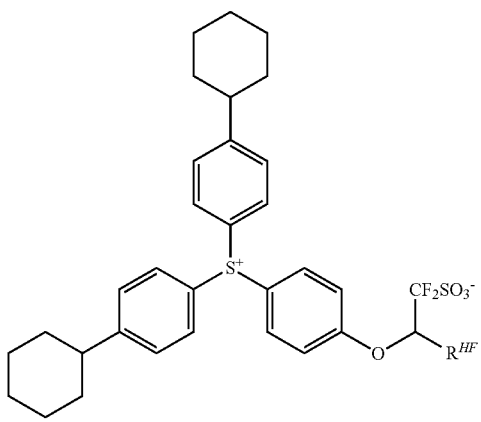

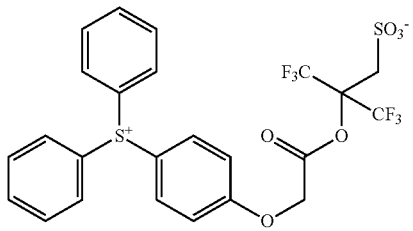

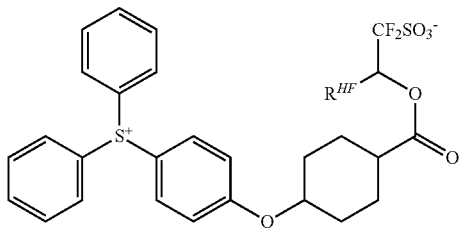

-continued

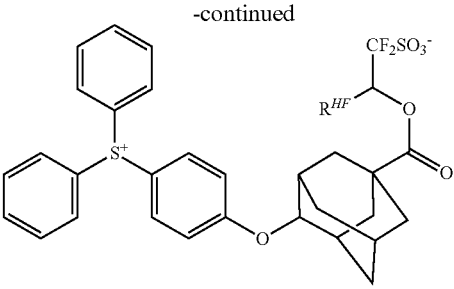

In the preferred embodiment, the resist composition contains the PAG (A), i.e., sulfonium salt having formula (1) and at least one other PAG (D). The PAG (A) has a high transmittance, can be added in a large amount to a resist composition, and is expected to achieve improvements in LWR and DOF. On the other hand, the acid generation efficiency of the PAG (A) is moderate. For obtaining a high sensitivity, the PAG (A) is preferably used in combination with another PAG providing a high sensitivity such as triphenylsulfonium nonafluorobutanesulfonate.

The other PAG as component (D) is preferably used in an amount of 0 to 30 parts, and when added, preferably 1 to 20 parts, more preferably 2 to 15 parts by weight per 80 parts by weight of the base polymer as component (B). An amount within the range eliminates any risks including degraded resolution and foreign particles during resist film stripping. The other PAG as component (D) may be used alone or in admixture.

(E) Quencher

To the resist composition, (E) a quencher may be added. As used herein, the "quencher" refers to a compound capable of suppressing the rate of diffusion when the acid generated by the PAG diffuses within the resist film.

Suitable quenchers include primary, secondary and tertiary amine compounds, preferably amine compounds having a hydroxyl group, ether bond, ester bond, lactone ring, cyano group or sulfonate bond. Primary or secondary amine compounds protected with a carbamate group are also useful as the quencher. Such protected amine compounds are effective particularly when the resist composition contains a base-labile component. The compounds shown below are exemplary of the quencher as well as the compounds described in JP-A 2008-111103, paragraphs [0146]-[0164] (U.S. Pat. No. 7,537,880) and JP 3790649, although the quencher is not limited thereto.

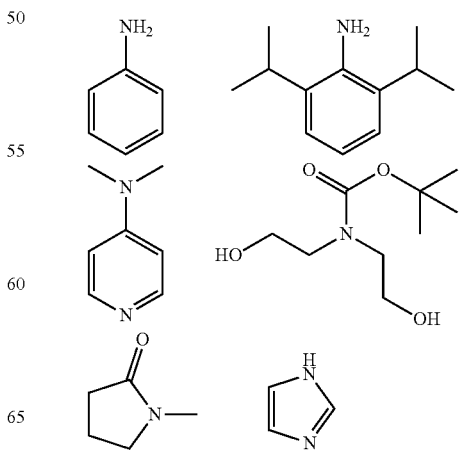

-continued
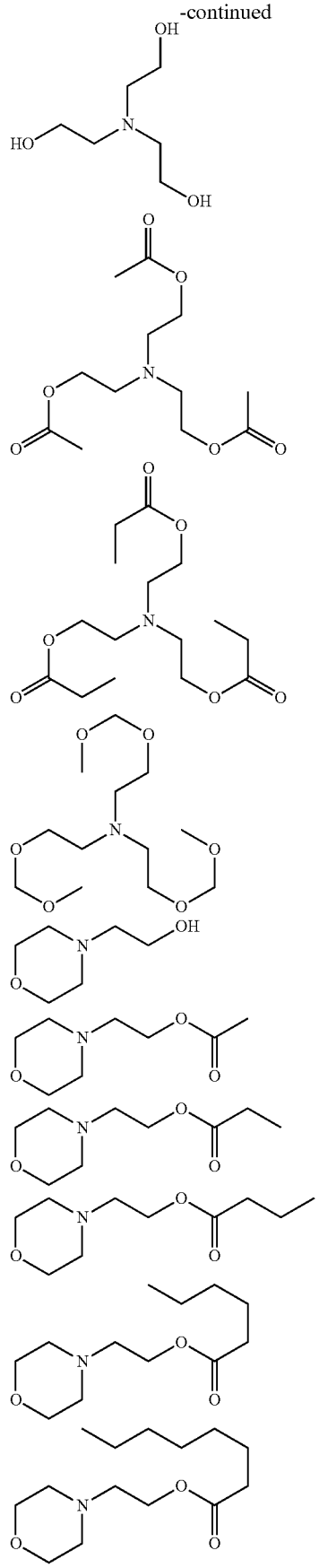
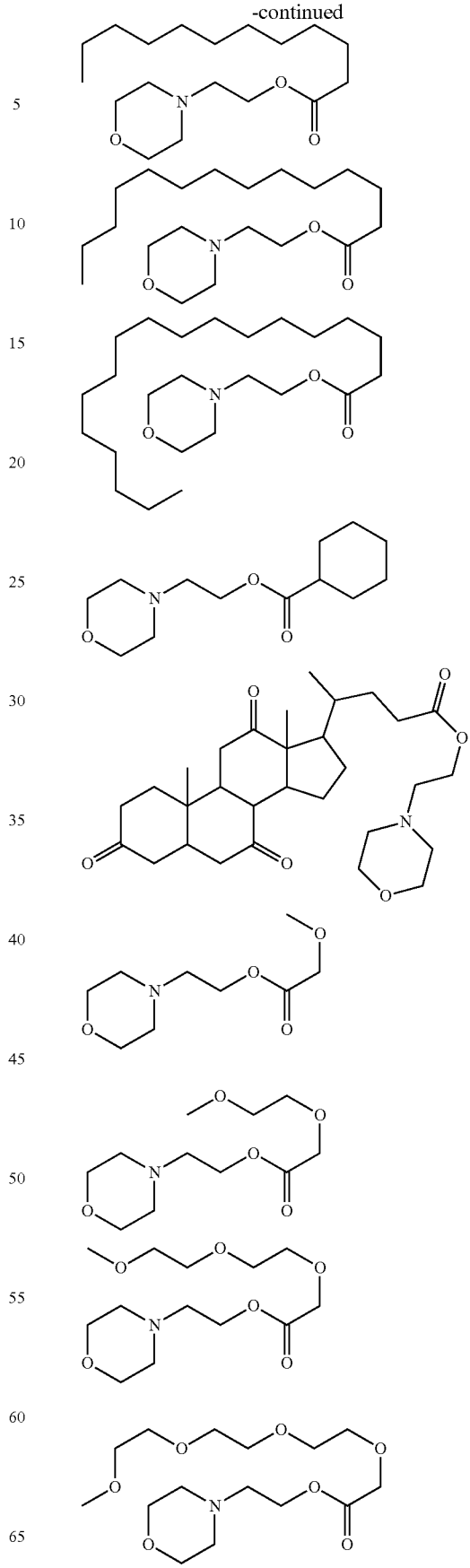

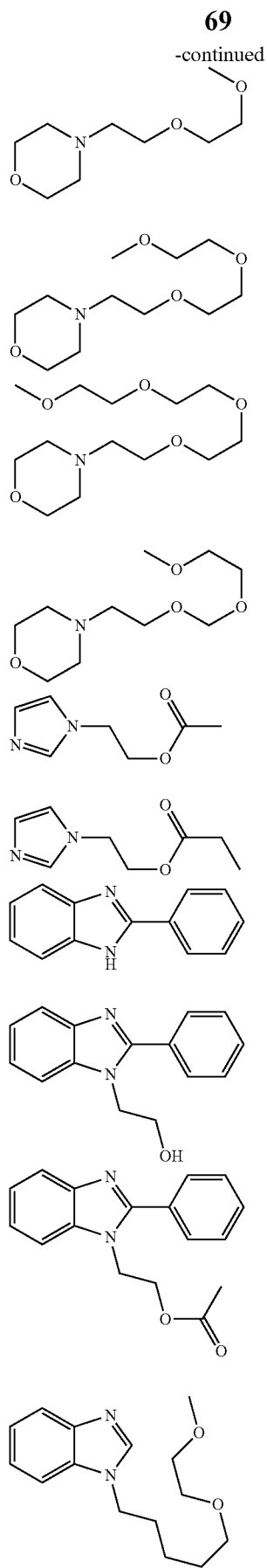
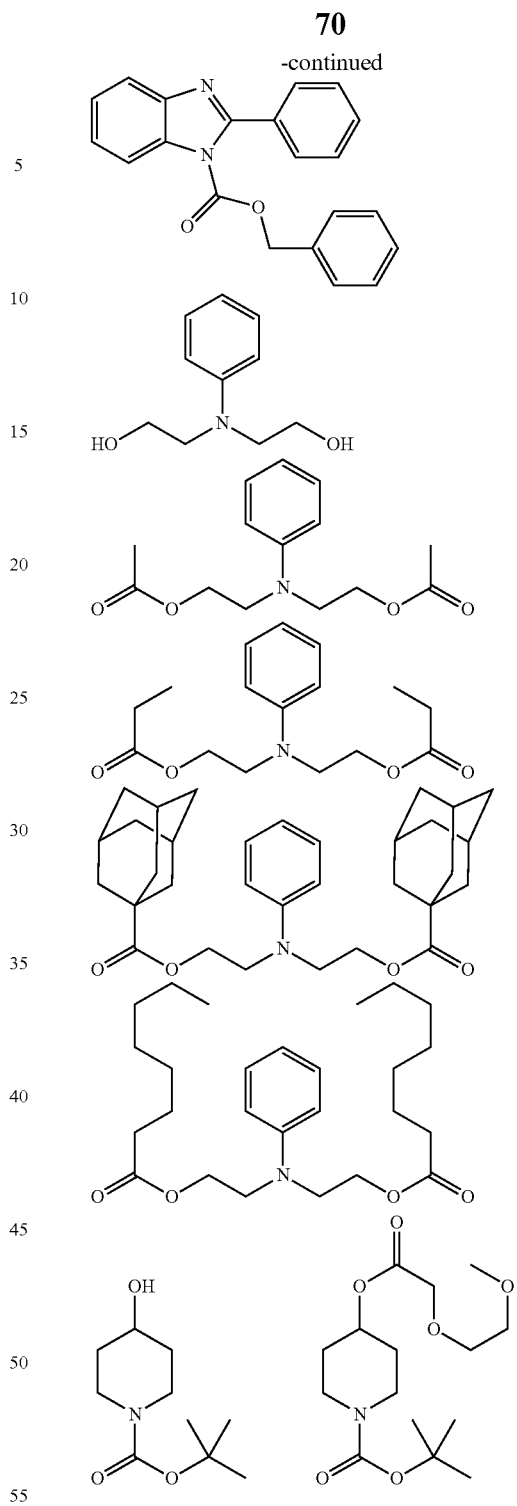

When an amine compound is used as the quencher, a sufficient acid diffusion controlling effect is expectable from small amounts of addition. As compared with onium salt type quenchers (described below), the amine quenchers are well dissolvable in organic solvents and contain a small number of light-absorbing functional groups such as benzene rings. Then, when an amine quencher is added to a resist composition comprising the PAG (A) according to the invention, a pattern with improved DOF and minimal defectivity can be formed by virtue of an acid diffusion controlling effect and high transmittance. Also the amine compound having a relatively low boiling point tends to segregate on the resist film surface under vacuum conditions during exposure. This suggests efficient capture of the generated acid on the resist film surface where the most generated acid is available, enabling to form patterns of rectangular profile.

Other examples of the quencher (E) include an onium salt of sulfonic acid which is not fluorinated at α-position, represented by the formula (4), and an onium salt of carboxylic acid, represented by the formula (5).

(4)

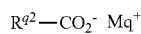
(5)

In formula (4), $R^{q1}$ is hydrogen or a $C_1$-$C_{40}$ monovalent hydrocarbon group which may contain a heteroatom, exclusive of the group wherein hydrogen bonded to the carbon atom at α-position relative to the sulfo group is substituted by fluorine or fluoroalkyl.

The monovalent hydrocarbon group $R^{q1}$ may be straight, branched or cyclic. Examples thereof include straight, branched or cyclic alkyl groups such as methyl, ethyl, propyl, isopropyl, n-butyl, sec-butyl, tert-butyl, tert-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl; straight, branched or cyclic alkenyl groups such as vinyl, allyl, propenyl, butenyl, hexenyl, and cyclohexenyl; aryl groups such as phenyl and naphthyl; heteroaryl groups such as thienyl; hydroxyphenyl groups such as 4-hydroxyphenyl; alkoxyphenyl groups such as 4-methoxyphenyl, 3-methoxyphenyl, 2-methoxyphenyl, 4-ethoxyphenyl, 4-tert-butoxyphenyl, and 3-tert-butoxyphenyl; alkylphenyl groups such as 2-methylphenyl, 3-methylphenyl, 4-methylphenyl, 4-ethylphenyl, 4-tert-butylphenyl, 4-n-butylphenyl, 2,4-dimethylphenyl, and 2,4,6-triisopropylphenyl; alkylnaphthyl groups such as methylnaphthyl and ethylnaphthyl; alkoxynaphthyl groups such as methoxynaphthyl, ethoxynaphthyl, n-propoxynaphthyl and n-butoxynaphthyl; dialkylnaphthyl groups such as dimethylnaphthyl and diethylnaphthyl; dialkoxynaphthyl groups such as dimethoxynaphthyl and diethoxynaphthyl; aralkyl groups such as benzyl, 1-phenylethyl and 2-phenylethyl; and aryloxyalkyl groups, typically 2-aryl-2-oxoethyl groups such as 2-phenyl-2-oxoethyl, 2-(1-naphthyl)-2-oxoethyl and 2-(2-naphthyl)-2-oxoethyl. In these groups, some hydrogen may be substituted by a moiety containing a heteroatom such as oxygen, sulfur, nitrogen or halogen, and a moiety containing a heteroatom such as oxygen, sulfur or nitrogen may intervene between carbon atoms, so that the group may contain a hydroxyl moiety, cyano moiety, carbonyl moiety, ether bond, ester bond, sulfonic acid ester bond, carbonate bond, lactone ring, sultone ring, carboxylic anhydride, or haloalkyl moiety.

In formula (5), $R^{q2}$ is hydrogen or a $C_1$-$C_{40}$ monovalent hydrocarbon group which may contain a heteroatom. The monovalent hydrocarbon group $R^{q2}$ may be straight, branched or cyclic. Examples of the group RV are as exemplified above for the group $R^{q1}$. Also included are fluorinated alkyl groups such as trifluoromethyl, trifluoroethyl, 2,2,2-trifluoro-1-methyl-1-hydroxyethyl, 2,2,2-trifluoro-1-(trifluoromethyl)-1-hydroxyethyl, and fluorinated aryl groups such as pentafluorophenyl and 4-trifluoromethylphenyl.

Preferred examples of the anion in the onium salt having formula (4) are shown below, but not limited thereto.

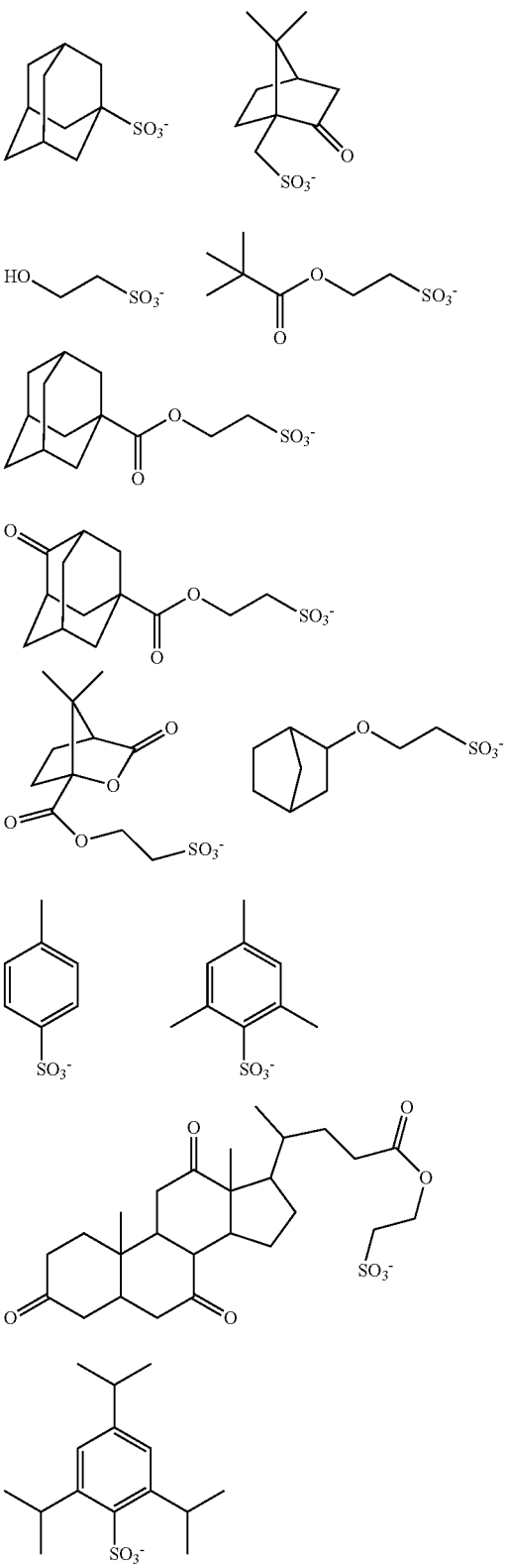

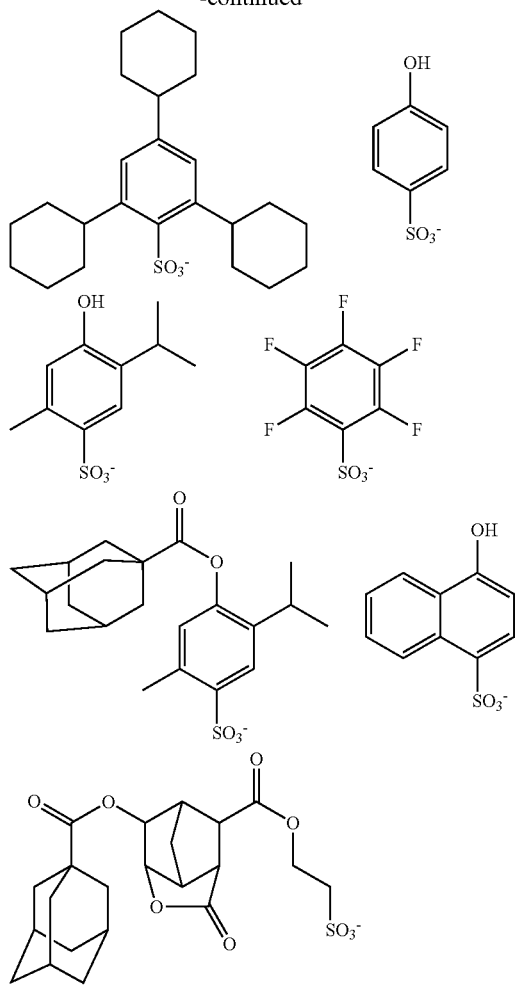
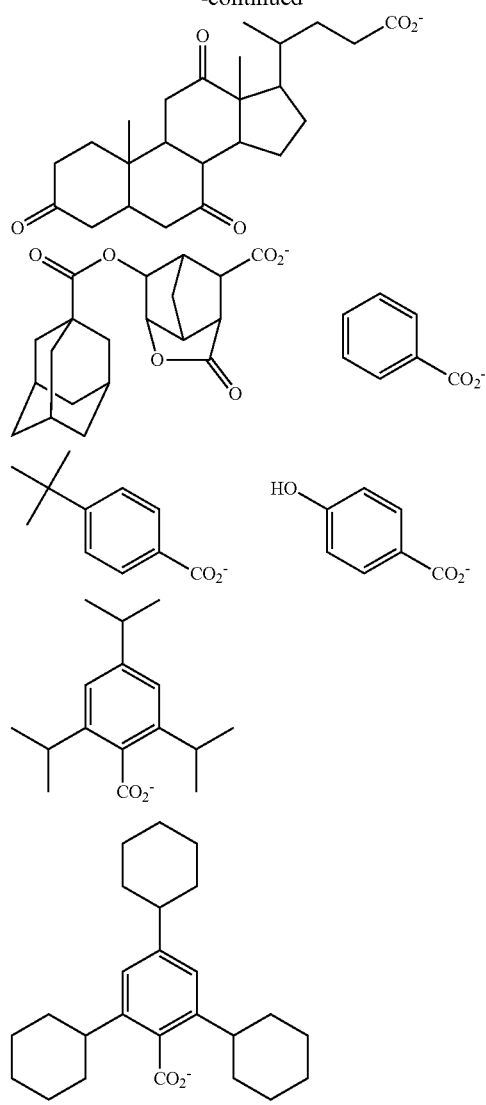
Preferred examples of the anion in the onium salt having formula (5) are shown below, but not limited thereto.
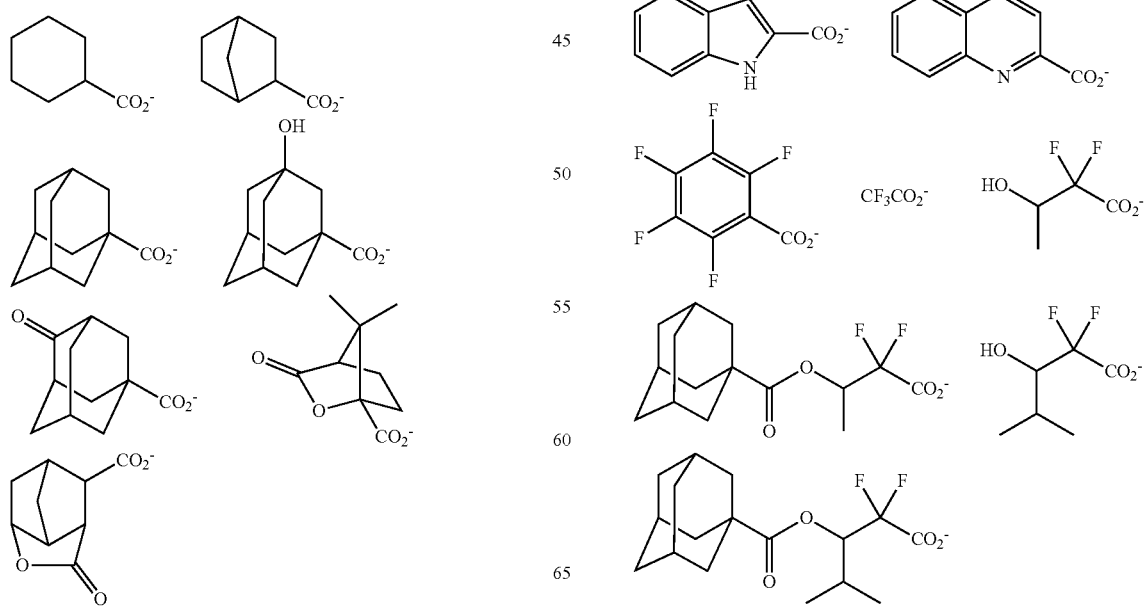
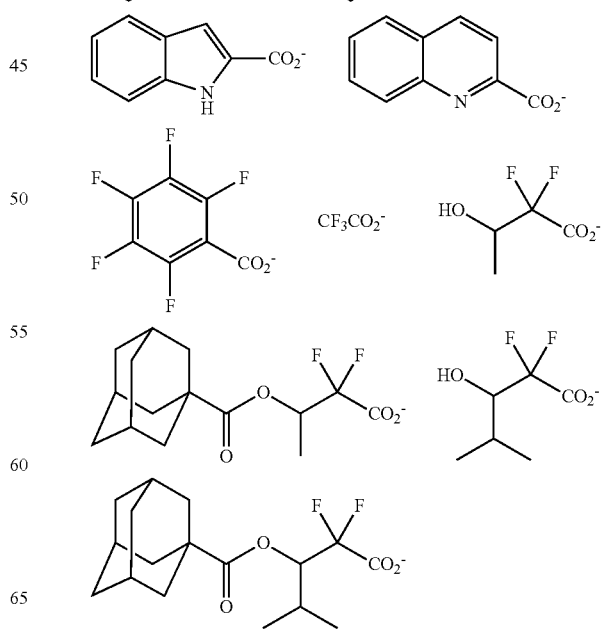

-continued

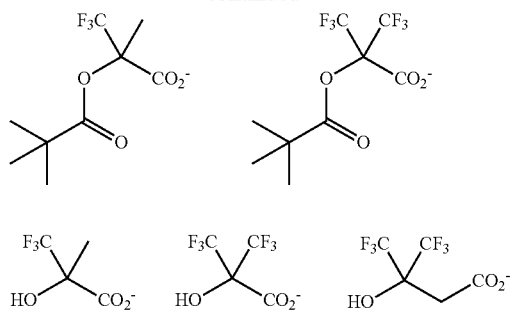

In formulae (4) and (5), $Mq^+$ is an onium cation, which is preferably selected from cations having the formulae (6A), (6B) and (6C).

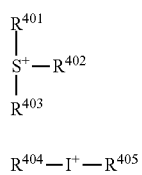 (6A)

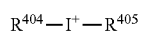 (6B)

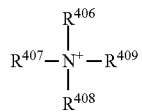 (6C)

In formulae (6A) to (6C), $R^{401}$ to $R^{409}$ are each independently a $C_1$-$C_{40}$ monovalent hydrocarbon group which may contain a heteroatom. A pair of $R^{401}$ and $R^{402}$ may bond together to form a ring with the sulfur atom to which they are attached. A pair of $R^{406}$ and $R^{407}$ may bond together to form a ring with the nitrogen atom to which they are attached. Examples of the monovalent hydrocarbon group are as exemplified above for $R^{q1}$ in formula (5).

Examples of the sulfonium cation having formula (6A) are as exemplified above as the cation in formulae (c2) to (c4). Examples of the iodonium cation having formula (6B) and examples of the ammonium cation having formula (6C) are shown below, but not limited thereto.

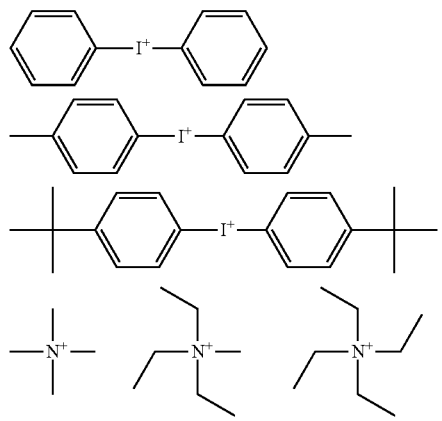

-continued

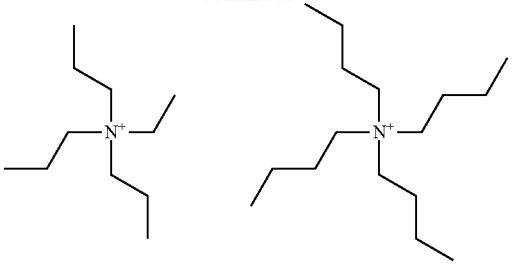

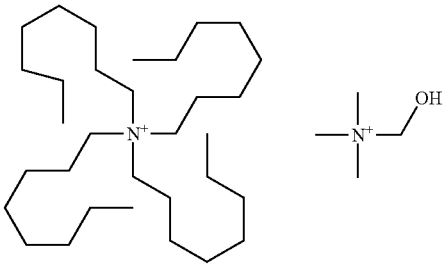

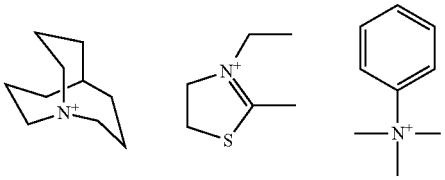

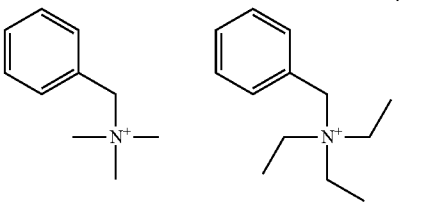

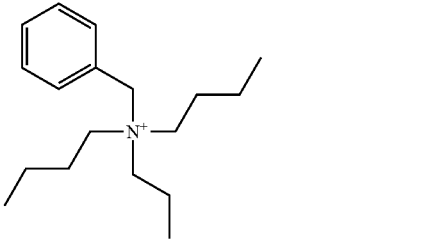 [SMILES: CCCC[N+](CCC)(CCCC)Cc1ccccc1]

Exemplary structures of the onium salt having formula (4) or (5) include arbitrary combinations of anions with cations, both as exemplified above. These onium salts may be readily prepared from ion exchange reaction using any well-known organic chemistry technique. For the ion exchange reaction, reference may be made to JP-A 2007-145797, for example.

In the inventive resist composition, the onium salt having formula (4) or (5) serves as a quencher. This is because the counter anion in the onium salt is a conjugated base of weak acid. As used herein, the weak acid indicates an acidity insufficient to deprotect an acid labile group from an acid labile group-containing unit in the base polymer. The onium salt having formula (4) or (5) functions as a quencher when used in combination with an onium salt type PAG having a conjugated base of a strong acid (typically a sulfonic acid which is fluorinated at α-position) as the counter anion. In a system using a mixture of an onium salt capable of generating a strong acid (e.g., α-position fluorinated sulfonic acid) and an onium salt capable of generating a weak acid (e.g., non-fluorinated sulfonic acid or carboxylic acid), if the strong acid generated from the PAG upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

In particular, since the onium salt having formula (4) or (5) wherein $Mq^+$ is a sulfonium cation having formula (6A) or an iodonium cation having formula (6B) is photo-decomposable, those portions receiving a high light intensity are reduced in quenching capability and increased in the concentration of a strong acid originating from the PAG. This enables to form a pattern having an improved contrast in exposed area, satisfactory LWR and CDU.

In case the acid labile group is an acetal group which is very sensitive to acid, the acid for eliminating the protective group need not necessarily be an α-fluorinated sulfonic acid, imide acid or methide acid. Sometimes, deprotection reaction may take place even with α-position non-fluorinated sulfonic acid. In this case, amine compounds and onium salts of carboxylic acid having formula (5) are preferably used as the quencher.

Besides the aforementioned quenchers of onium salt type, betaine type quenchers such as diphenyliodonium-2-carboxylate may also be used.

Also, a photo-decomposable onium salt having a nitrogen-containing substituent may be used as the quencher. This compound functions as a quencher in the unexposed region, but as a so-called photo-degradable base in the exposed region because it loses the quencher function in the exposed region due to neutralization thereof with the acid generated by itself. Using a photo-degradable base, the contrast between exposed and unexposed regions can be further enhanced.

With respect to the photo-degradable base, reference may be made to JP-A 2009-109595, 2012-046501 and JP-A 2013-209360, for example. Examples of the cation in the photo-degradable base include those exemplified above for the sulfonium cation in formulae (c2) to (c4), the iodonium cation having formula (6B), and the ammonium cation having formula (6C). Examples of the anion in the photo-degradable base are shown below, but not limited thereto. Herein $A^4$ is hydrogen or trifluoromethyl.

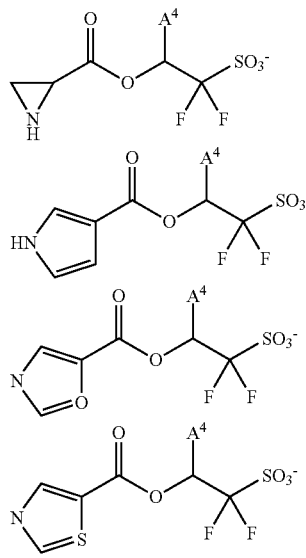

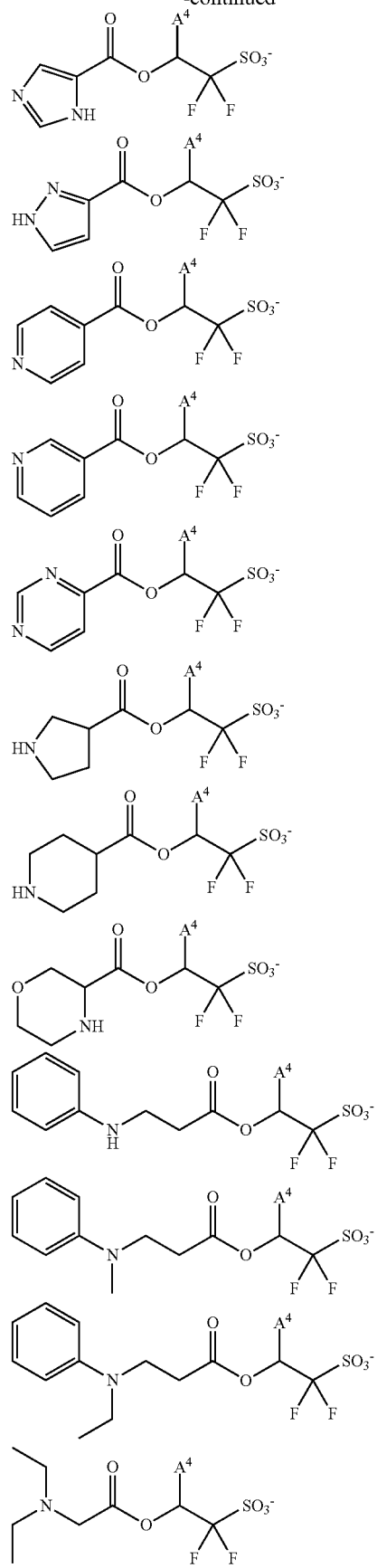

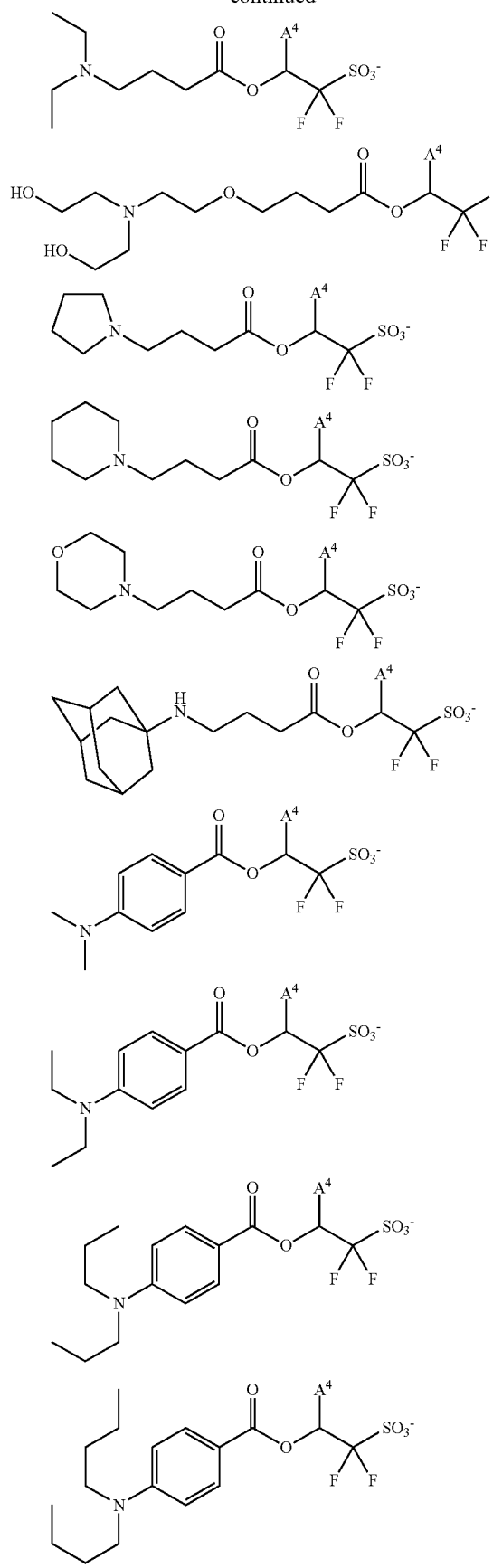
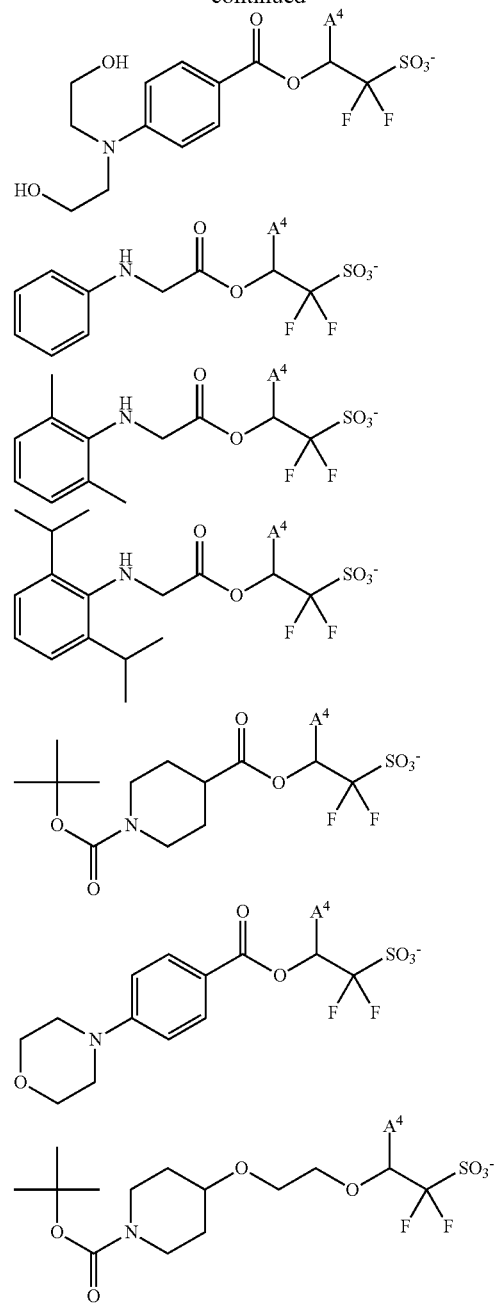

Examples of the photo-degradable onium salt include combinations of anions with cations, both as exemplified above, but are not limited thereto.

In the resist composition, the amount of the quencher used as component (E) is preferably 0 to 40 parts by weight, and when added, 0.1 to 20 parts by weight, more preferably 0.5 to 15 parts by weight per 80 parts by weight of the base polymer (B). The inclusion of the quencher in the range facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile. The inclusion of the quencher is also effective for improving adhesion to the substrate.

The quencher (E) may be used alone or in admixture.

(F) Surfactant

The resist composition may further comprise (F) a surfactant which is commonly used for facilitating coating operation.

Component (F) is typically a surfactant which is insoluble or substantially insoluble in water and alkaline developer or a surfactant which is insoluble or substantially insoluble in water and soluble in alkaline developer. For the surfactant, reference should be made to those compounds described in JP-A 2010-215608 and JP-A 2011-016746.

While many examples of the surfactant which is insoluble or substantially insoluble in water and alkaline developer are described in the patent documents cited herein, preferred examples are fluorochemical surfactants FC-4430 (3M), Olfine® E1004 (Nissin Chemical Co., Ltd.), Surflon® S-381, KH-20 and KH-30 (AGC Seimi Chemical Co., Ltd.). Partially fluorinated oxetane ring-opened polymers having the formula (surf-1) are also useful.

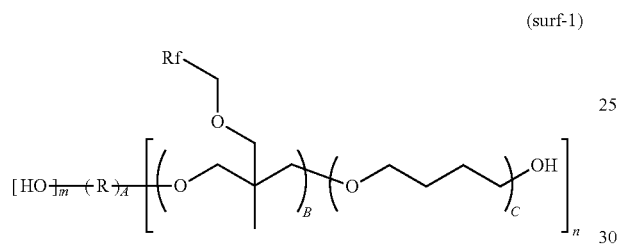

(surf-1)

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent aliphatic groups include ethylene, 1,4-butylene, 1,2-propylene, 2,2-dimethyl-1,3-propylene and 1,5-pentylene. Exemplary tri- and tetra-valent groups are shown below.

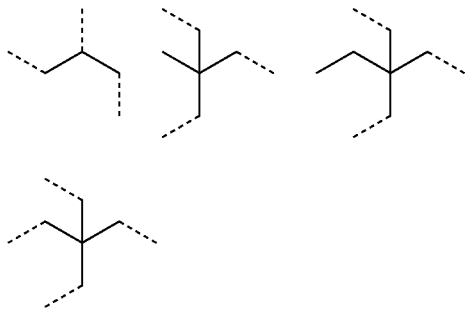

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of m and n, which represents the valence of R, is an integer of 2 to 4. "A" is equal to 1, B is an integer of 2 to 25, and C is an integer of 0 to 10. Preferably, B is an integer of 4 to 20, and C is 0 or 1. Note that the formula (surf-1) does not prescribe the arrangement of respective constituent units while they may be arranged either blockwise or randomly. For the preparation of surfactants in the form of partially fluorinated oxetane ring-opened polymers, reference should be made to U.S. Pat. No. 5,650,483, for example.

The surfactant which is insoluble or substantially insoluble in water and soluble in alkaline developer is useful when ArF immersion lithography is applied to the resist composition in the absence of a resist protective film. In this embodiment, the surfactant has a propensity to segregate on the resist surface after spin coating for achieving a function of minimizing water penetration or leaching. The surfactant is also effective for preventing water-soluble components from being leached out of the resist film for minimizing any damage to the exposure tool. The surfactant becomes solubilized during alkaline development following exposure and PEB, and thus forms few or no foreign particles which become defects. The preferred surfactant is a polymeric surfactant which is insoluble or substantially insoluble in water, but soluble in alkaline developer, also referred to as "hydrophobic resin" in this sense, and especially which is water repellent and enhances water sliding.

Suitable polymeric surfactants include those containing recurring units of at least one type selected from the formulae (7A) to (7E).

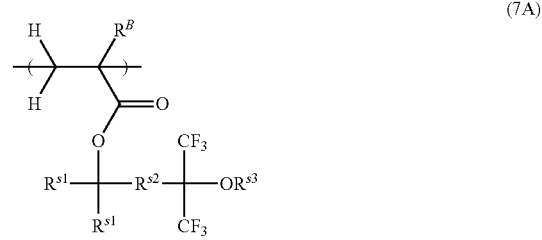

(7A)

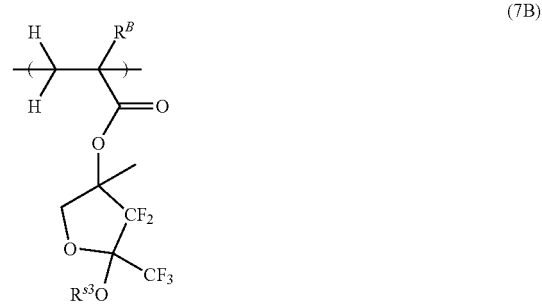

(7B)

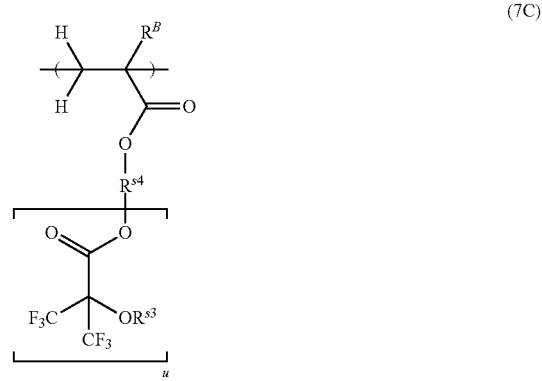

(7C)

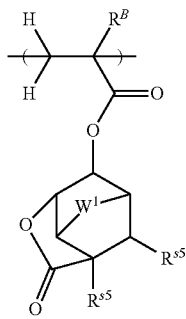

(7D)

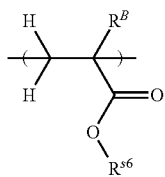

(7E)

Herein, $R^B$ is hydrogen, fluorine, methyl or trifluoromethyl. $W^1$ is —CH$_2$—, —CH$_2$CH$_2$— or —O—, or two separate —H. $R^{s1}$ is each independently hydrogen or a $C_1$-$C_{10}$ monovalent hydrocarbon group. $R^{s2}$ is a single bond or a $C_1$-$C_5$ straight or branched divalent hydrocarbon group. $R^{s3}$ is each independently hydrogen, a $C_1$-$C_{15}$ monovalent hydrocarbon or fluorinated hydrocarbon group, or an acid labile group. When $R^{s3}$ is a monovalent hydrocarbon or fluorinated hydrocarbon group, an ether bond (—O—) or carbonyl moiety (—C(=O)—) may intervene in a carbon-carbon bond. $R^{s4}$ is a $C_1$-$C_{20}$ (u+1)-valent hydrocarbon or fluorinated hydrocarbon group, and u is an integer of 1 to 3. IV is each independently hydrogen or a group having the formula:

—C(=O)—O—$R^{s7}$ wherein $R^{s7}$ is a $C_1$-$C_{20}$ fluorinated hydrocarbon group. $R^{s6}$ is a $C_1$-$C_{15}$ monovalent hydrocarbon or fluorinated hydrocarbon group in which an ether bond (—O—) or carbonyl moiety (—C(=O)—) may intervene in a carbon-carbon bond.

The monovalent hydrocarbon group represented by $R^{s1}$ may be straight, branched or cyclic and examples thereof include methyl, ethyl, n-propyl, isopropyl, cyclopropyl, n-butyl, isobutyl, sec-butyl, tert-butyl, cyclobutyl, n-pentyl, cyclopentyl, n-hexyl, cyclohexyl, n-heptyl, n-octyl, n-nonyl, n-decyl, adamantyl, and norbornyl. Inter alia, $C_1$-$C_6$ hydrocarbon groups are preferred.

The divalent hydrocarbon group represented by $R^{s2}$ may be straight, branched or cyclic and examples thereof include methylene, ethylene, propylene, butylene, and pentylene.

The monovalent hydrocarbon group represented by $R^{s3}$ or $R^{s6}$ may be straight, branched or cyclic and examples thereof include alkyl, alkenyl, and alkynyl groups, with the alkyl groups being preferred. Suitable alkyl groups include those exemplified for the monovalent hydrocarbon group represented by $R^{s1}$ as well as n-undecyl, n-dodecyl, tridecyl, tetradecyl, and pentadecyl. Examples of the monovalent fluorinated hydrocarbon group represented by $R^{s3}$ or $R^{s6}$ include the foregoing monovalent hydrocarbon groups in which some or all carbon-bonded hydrogen atoms are substituted by fluorine atoms. In these groups, an ether bond (—O—) or carbonyl moiety (—C(=O)—) may intervene in a carbon-carbon bond as mentioned above.

Examples of the acid labile group represented by $R^{s3}$ include those exemplified above for the acid labile group $X^A$ in formula (a), $C_4$-$C_{40}$, preferably $C_4$-$C_{15}$ tertiary alkyl groups, trialkylsilyl groups in which each alkyl moiety has 1 to 6 carbon atoms, and $C_4$-$C_{20}$ oxoalkyl groups.

The (u+1)-valent hydrocarbon or fluorinated hydrocarbon group represented by $R^{s4}$ may be straight, branched or cyclic and examples thereof include the foregoing monovalent hydrocarbon or fluorinated hydrocarbon groups from which the number (u) of hydrogen atoms are eliminated.

The fluorinated hydrocarbon group represented by $R^{s7}$ may be straight, branched or cyclic and examples thereof include the foregoing monovalent hydrocarbon groups in which some or all hydrogen atoms are substituted by fluorine atoms. Illustrative examples include trifluoromethyl, 2,2,2-trifluoroethyl, 3,3,3-trifluoro-1-propyl, 3,3,3-trifluoro-2-propyl, 2,2,3,3-tetrafluoropropyl, 1,1,1,3,3,3-hexafluoroisopropyl, 2,2,3,3,4,4,4-heptafluorobutyl, 2,2,3,3,4,4,5,5-octafluoropentyl, 2,2,3,3,4,4,5,5,6,6,7,7-dodecafluoroheptyl, 2-(perfluorobutyl)ethyl, 2-(perfluorohexyl)ethyl, 2-(perfluorooctyl)ethyl, and 2-(perfluorodecyl)ethyl.

Examples of the recurring units having formulae (7A) to (7E) are shown below, but not limited thereto. Herein $R^B$ is as defined above.

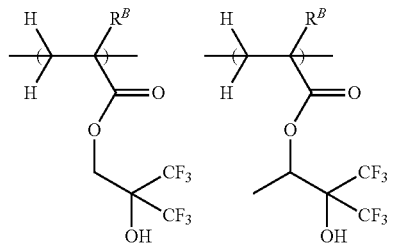

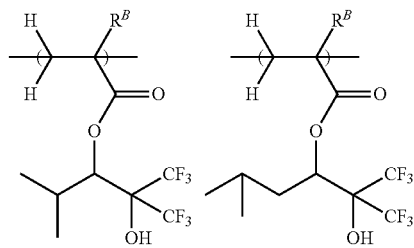

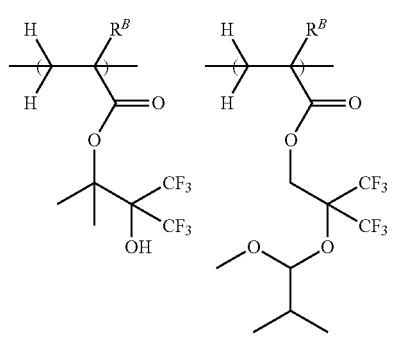

-continued
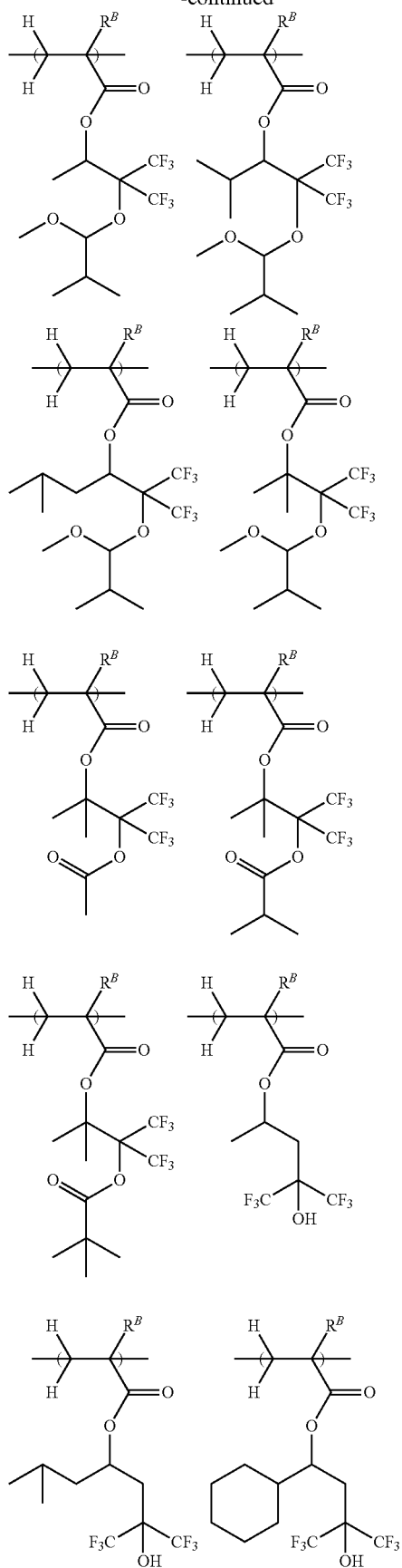
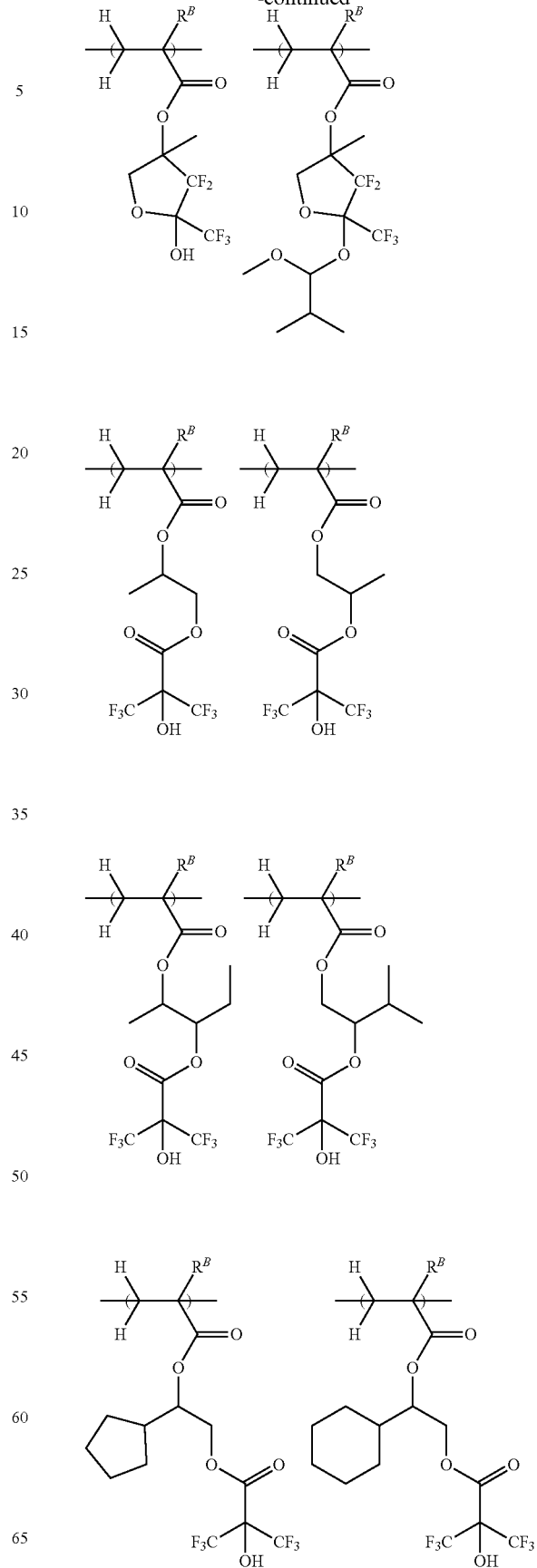

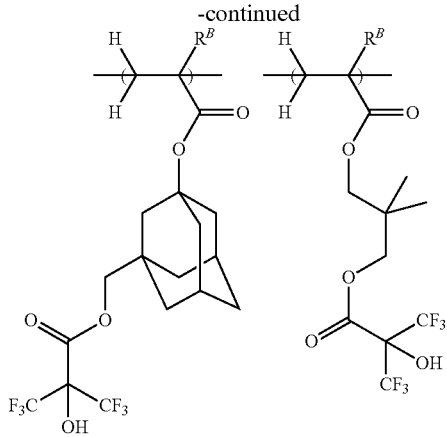
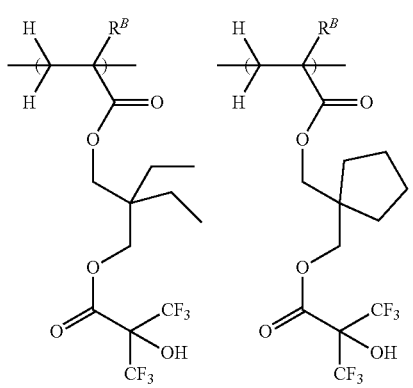
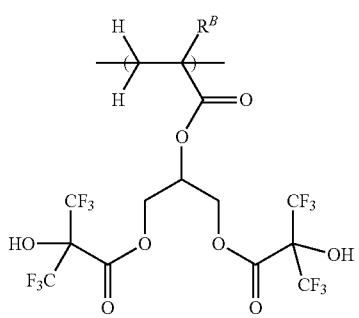
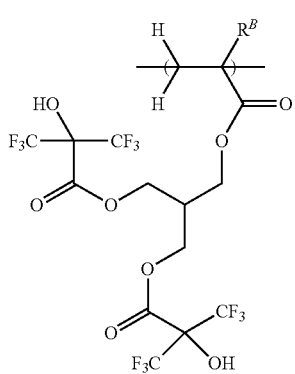
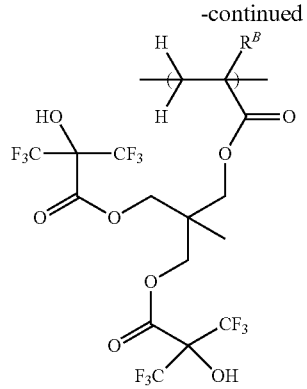
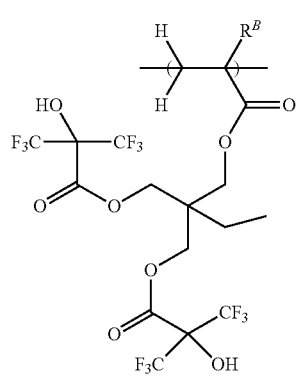
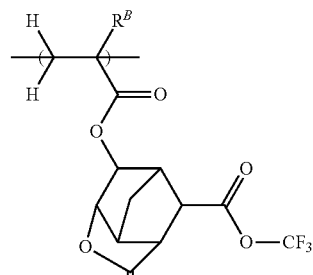
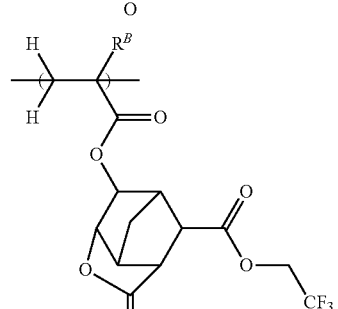
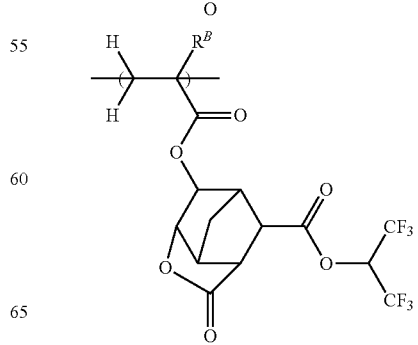

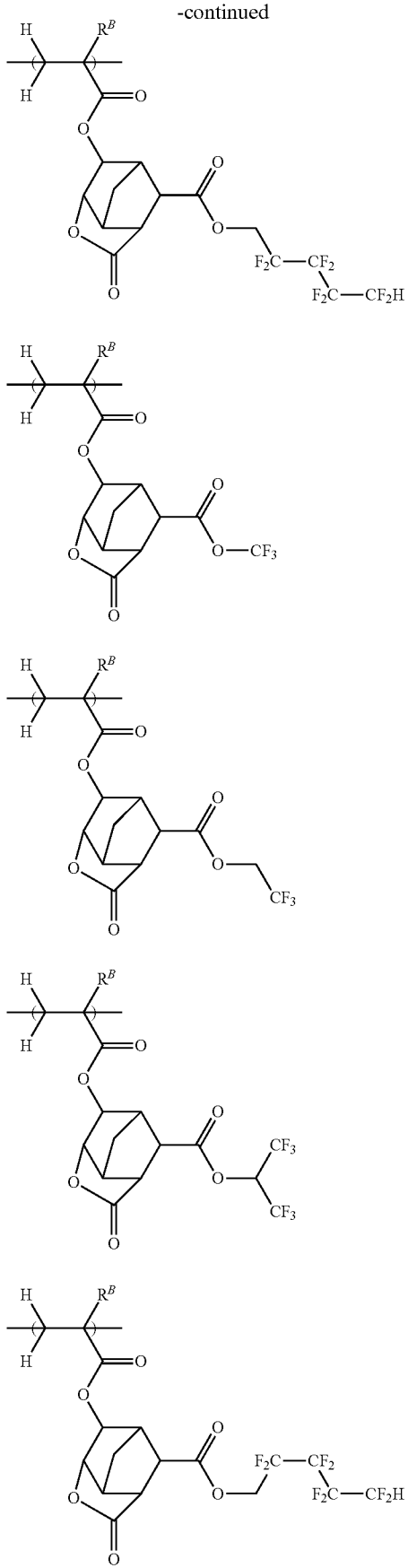
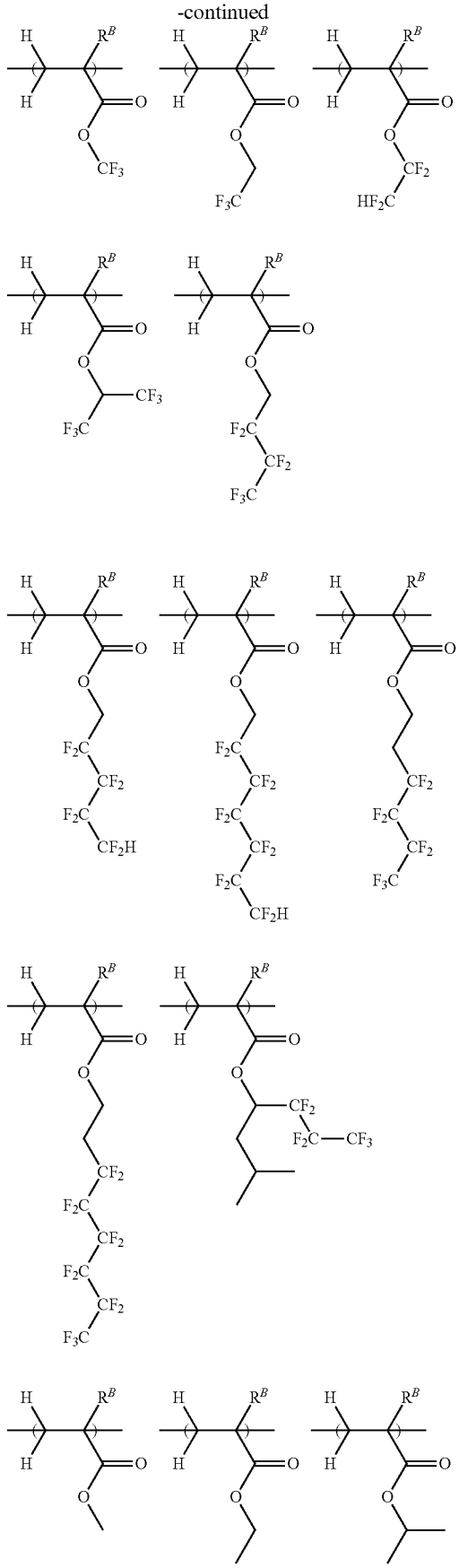

-continued

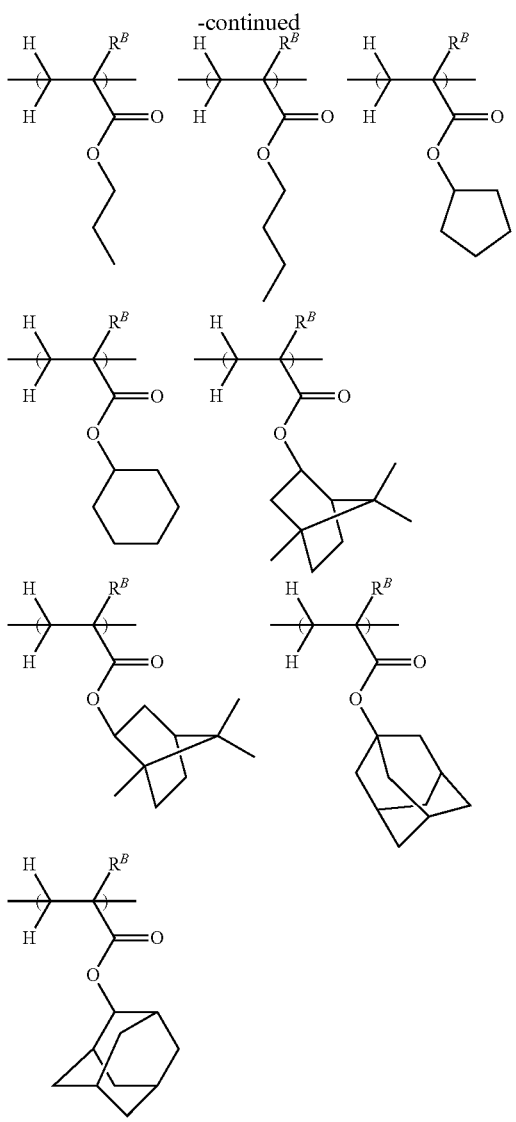

The polymeric surfactant may further contain recurring units other than the recurring units having formulae (7A) to (7E). Typical other recurring units are those derived from methacrylic acid and α-trifluoromethylacrylic acid derivatives. In the polymeric surfactant, the content of the recurring units having formulae (7A) to (7E) is preferably at least 20 mol %, more preferably at least 60 mol %, most preferably 100 mol % of the overall recurring units.

The polymeric surfactant preferably has a Mw of 1,000 to 500,000, more preferably 3,000 to 100,000 and a Mw/Mn of 1.0 to 2.0, more preferably 1.0 to 1.6.

The polymeric surfactant may be synthesized by any desired method, for example, by dissolving an unsaturated bond-containing monomer or monomers providing recurring units having formula (7A) to (7E) and optionally other recurring units in an organic solvent, adding a radical initiator, and heating for polymerization. Suitable organic solvents used herein include toluene, benzene, THF, diethyl ether, and dioxane. Examples of the polymerization initiator used herein include azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the reaction temperature is 50 to 100° C. and the reaction time is 4 to 24 hours. The acid labile group that has been incorporated in the monomer may be kept as such, or the polymer may be protected or partially protected therewith at the end of polymerization.

During the synthesis of polymeric surfactant, any known chain transfer agent such as dodecyl mercaptan or 2-mercaptoethanol may be added for molecular weight control purpose. The amount of chain transfer agent added is preferably 0.01 to 10 mol % based on the total moles of monomers to be polymerized.

With respect to the surfactant which is insoluble or substantially insoluble in water and soluble in alkaline developer, reference should also be made to JP-A 2007-297590, JP-A 2008-088343, JP-A 2008-111103, JP-A 2008-122932, JP-A 2009-098638, JP-A 2009-191151, JP-A 2009-192784, JP-A 2009-276363, JP-A 2010-134012, JP-A 2010-107695, JP-A 2010-250105, and JP-A 2011-042789.

When the resist composition contains a surfactant (F), the amount thereof is preferably 0.001 to 20 parts by weight, and more preferably 0.01 to 10 parts by weight per 80 parts by weight of the base polymer (B). The surfactant (F) may be used alone or in admixture.

(G) Other Components

The resist composition may further comprise (G) another component, for example, a compound which is decomposed with an acid to generate another acid (i.e., acid amplifier compound), an organic acid derivative, a fluorinated alcohol, a crosslinker, a compound having a Mw of up to 3,000 which changes its solubility in developer under the action of an acid (i.e., dissolution inhibitor), or acetylene alcohol. Specifically, the acid amplifier compound is described in JP-A 2009-269953 and JP-A 2010-215608 and preferably used in an amount of 0 to 5 parts, more preferably 0 to 3 parts by weight per 80 parts by weight of the base polymer (B). An extra amount of the acid amplifier compound can make the acid diffusion control difficult and cause degradations to resolution and pattern profile. With respect to the remaining additives, reference should be made to U.S. Pat. Nos. 7,771,914, 8,114,571, and 8,283,104 (JP-A 2008-122932, paragraphs [0155]-[0182], 2009-269953, and 2010-215608).

Process

A further embodiment of the invention is a pattern forming process using the resist composition defined above. A pattern may be formed from the resist composition using any well-known lithography process. The preferred process includes the steps of applying the resist composition to form a resist film on a substrate, exposing a selected region of the resist film to KrF excimer laser, ArF excimer laser, EB or EUV, and developing the exposed resist film in a developer. Any desired steps may be added to the process if necessary.

The substrate used herein may be a substrate for integrated circuitry fabrication, e.g., Si, $SiO_2$, SiN, SiON, TiN, WSi, BPSG, SOG, organic antireflective film, etc. or a substrate for mask circuitry fabrication, e.g., Cr, CrO, CrON, $MoSi_2$, $SiO_2$, etc.

The resist composition is applied onto a substrate by a suitable coating technique such as spin coating. The coating is prebaked on a hotplate preferably at a temperature of 60 to 180° C. for 10 to 600 seconds, more preferably at 70 to 150° C. for 15 to 300 seconds. The resulting resist film preferably has a thickness of 10 to 2,000 nm, more preferably 20 to 500 nm.

Then the resist film is exposed patternwise to excimer laser, EUV or EB. On use of KrF excimer laser, ArF excimer laser or EUV of wavelength 13.5 nm, the resist film is exposed through a mask having a desired pattern, preferably in a dose of 1 to 200 mJ/cm$^2$, more preferably 10 to 100 mJ/cm$^2$. On use of EB, a pattern may be written directly or through a mask having the desired pattern, preferably in a dose of 1 to 300 μC/cm$^2$, more preferably 10 to 200 μC/cm$^2$.

The exposure may be performed by conventional lithography whereas the immersion lithography of holding a liquid between the mask and the resist film may be employed if desired. In the immersion lithography, preferably a liquid having a refractive index of at least 1.0 is held between the resist film and the projection lens. The liquid is typically water, and in this case, a protective film which is insoluble in water may be formed on the resist film.

While the water-insoluble protective film which is used in the immersion lithography serves to prevent any components from being leached out of the resist film and to improve water sliding on the film surface, it is generally divided into two types. The first type is an organic solvent-strippable protective film which must be stripped, prior to alkaline development, with an organic solvent in which the resist film is not dissolvable. The second type is an alkali-soluble protective film which is soluble in an alkaline developer so that it can be removed simultaneously with the removal of solubilized regions of the resist film. The protective film of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

After the exposure, the resist film may be baked (PEB), for example, on a hotplate at 60 to 150° C. for 1 to 5 minutes, preferably at 80 to 140° C. for 1 to 3 minutes.

The resist film is then developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle and spray techniques. In this way, a desired resist pattern is formed on the substrate.

The process of forming a positive tone pattern using an alkaline aqueous solution as the developer is detailed in U.S. Pat. No. 8,647,808 (JP-A 2011-231312, paragraphs [0138]-[0146]). The process of forming a negative tone pattern using an organic solvent as the developer is detailed in U.S. Pat. No. 9,256,127 (JP-A 2015-214634, paragraphs [0173]-[0183]). Any desired step may be added to the pattern forming process. For example, after the resist film is formed, a step of rinsing with pure water (post-soaking) may be introduced to extract the acid generator or the like from the film surface or wash away particles. After exposure, a step of rinsing (post-soaking) may be introduced to remove any water remaining on the film after exposure.

Also, a double patterning process may be used for pattern formation. The double patterning process includes a trench process of processing an underlay to a 1:3 trench pattern by a first step of exposure and etching, shifting the position, and forming a 1:3 trench pattern by a second step of exposure, for forming a 1:1 pattern; and a line process of processing a first underlay to a 1:3 isolated left pattern by a first step of exposure and etching, shifting the position, processing a second underlay formed below the first underlay by a second step of exposure through the 1:3 isolated left pattern, for forming a half-pitch 1:1 pattern.

Where a hole pattern is formed by negative tone development using organic solvent developer, exposure by double dipole illuminations of X- and Y-direction line patterns provides the highest contrast light. The contrast may be further increased by combining two dipole illuminations of X- and Y-direction line patterns with s-polarized illumination. These pattern forming processes are described in JP-A 2011-221513.

With respect to the developer used in the pattern forming process of the invention, the aqueous base solution may be the above-mentioned aqueous solution of TMAH or another aqueous base solution as described in JP-A 2015-180748, paragraphs [0148]-[0149]. A 2 to 3 wt % aqueous solution of TMAH is preferred.

In the organic solvent development, the organic solvent used as the developer is preferably selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, isopentyl acetate, butenyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate. These organic solvents may be used alone or in admixture of two or more.

A hole or trench pattern after development may be shrunk by the thermal flow, resolution enhancement lithography assisted by chemical shrink (RELACS) or directed self-assembly (DSA) process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is at a temperature of 70 to 180° C., preferably 80 to 170° C., for a time of 10 to 300 seconds. The extra shrink agent is stripped and the hole pattern is shrunk.

By the pattern forming process using the inventive resist composition, a fine size pattern which is improved in lithography performance factors including DOF, CDU, and LWR can be readily formed.

EXAMPLES

Examples and Comparative Examples are given below by way of illustration and not by way of limitation. All parts are by weight (pbw). For all polymers, Mw and Mn are determined by GPC versus polystyrene standards using tetrahydrofuran (THF) solvent. Analysis is made by time-of-flight mass spectrometry (TOF-MS), $^1$H- and $^{19}$F-NMR spectroscopy.

[1] Synthesis of PAGs

Synthesis Example 1-1

Synthesis of PAG-1

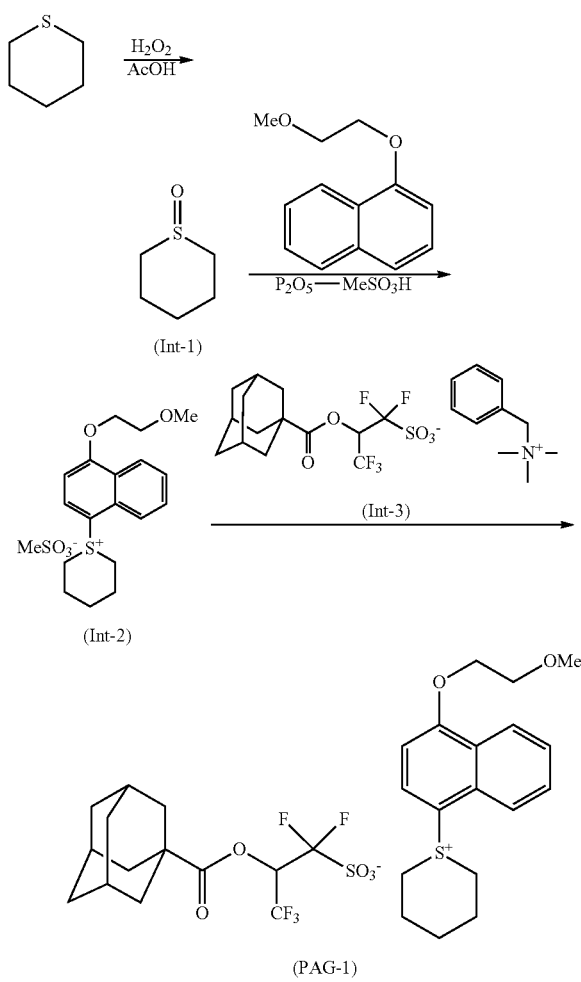

(1) Synthesis of Sulfoxide (Int-1)

While cooling so as to keep an internal temperature of 30° C., 98 g of 35 wt % aqueous hydrogen peroxide was added dropwise to a mixed solution of 100 g of to tetrahydro-2H-thiopyran (Tokyo Chemical Industry Co., Ltd.) and 700 g of acetic acid. Stirring was continued overnight. After the consumption or disappearance of the reactants was confirmed by gas chromatography, 12.2 g of sodium thiosulfate pentahydrate and 50 g of deionized water were added to the solution, followed by stirring for 1 hour. After the disappearance of hydrogen peroxide was confirmed, the reaction solution was filtered to remove the precipitated solids. The filtrate was concentrated at 60° C. under reduced pressure to remove acetic acid. After the concentrate was filtered, 300 g of methylene chloride and 300 g of deionized water were added thereto. The mixture was stirred, after which the organic layer was taken out. The water layer was extracted twice with 300 g of methylene chloride. All the organic layers were combined together and washed with 100 g of deionized water. The organic layer was concentrated at 60° C. under reduced pressure, obtaining 131.5 g of an acetic acid solution of thian-1-oxide (Int-1) (purity 69.9%, yield 81%).

(2) Synthesis of 1-[4-(2-methoxyethoxy)naphthyl]thian-1-ium Methanesulfonate (Int-2)

Under ice cooling, 44.1 g of the acetic acid solution of Int-1 synthesized in (1) was added dropwise to a mixed solution of 51.2 g of 1-(2-methoxyethoxy)naphthalene (see JP-A 2012-041320) and 153.5 g of Eaton's Reagent (Tokyo Chemical Industry Co., Ltd.). Stirring was continued overnight at room temperature. Under ice cooling, 250 g of deionized water and 92.1 g of 29 wt % ammonia water were added to the reaction solution for quenching. Further 300 g of diisopropyl ether was added to the reaction solution and stirred. The water layer was taken out and washed twice with 300 g of diisopropyl ether, obtaining 610.4 g of an aqueous solution of 1-[4-(2-methoxyethoxy)naphthyl]thian-1-ium methanesulfonate (Int-2) in crude form. The aqueous solution of crude product was used in the subsequent step without further purification.

(3) Synthesis of 1-[4-(2-methoxyethoxy)naphthyl]thian-1-ium 2-(adamantane-1-carbonyloxy)-1,1,3,3,3-pentafluoropropanesulfonate (PAG-1)

A mixture of 54 g of benzyltrimethylammonium 2-(adamantane-1-carbonyloxy)-1,1,3,3,3-pentafluoropropanesulfonate (Int-3), 342 g of the aqueous solution of Int-2, 452 g of methyl isobutyl ketone, and 150 g of deionized water was stirred for 30 minutes, after which the organic layer was taken out. The organic layer was washed 5 times with an aqueous dilution of 25 g Int-2 aqueous solution diluted with 100 g deionized water, once with 100 g of deionized water, once with 100 g of 1 wt % hydrochloric acid, and 8 times with 100 g of deionized water. The organic layer was concentrated under reduced pressure, after which 556 g of diisopropyl ether was added to the concentrate and stirred. After the solid precipitate was filtered off, the filtrate was washed once with diisopropyl ether and dried at 50° C. under reduced pressure, obtaining 67 g (yield 96%) of the target compound, 1-[4-(2-methoxyethoxy)naphthyl]thian-1-ium 2-(adamantane-1-carbonyloxy)-1,1,3,3,3-pentafluoropropanesulfonate (PAG-1). It was analyzed by $^1$H-NMR, $^{19}$F-NMR and MALDI TOF-MS, with the results shown below.

$^1$H-NMR (500 MHz, DMSO-$d_6$):
δ=1.60-1.78 (7H, m), 1.79-1.89 (7H, m), 1.93-2.06 (5H, m), 2.28-2.38 (2H, m),
3.38 (3H, s), 3.78-3.86 (6H, m), 4.46 (2H, m), 5.93 (1H, m), 7.36 (1H, d),
7.74 (1H, m), 7.85 (1H, m), 8.34 (1H, d), 8.37 (1H, d), 8.50 (1H, d) ppm $^{19}$F-NMR (500 MHz, DMSO-$d_6$):
δ=−119.6 (1F, m), −113.7 (1F, m), −72.6 (3F, m) ppm MALDI TOF-MS
Positive $M^+$ 303 (corresponding to $C_{18}H_{23}O_2S^+$)
Negative $M^-$ 391 (corresponding to $C_{14}H_{16}F_5O_5S^-$)

Synthesis Example 1-2

Synthesis of PAG-2

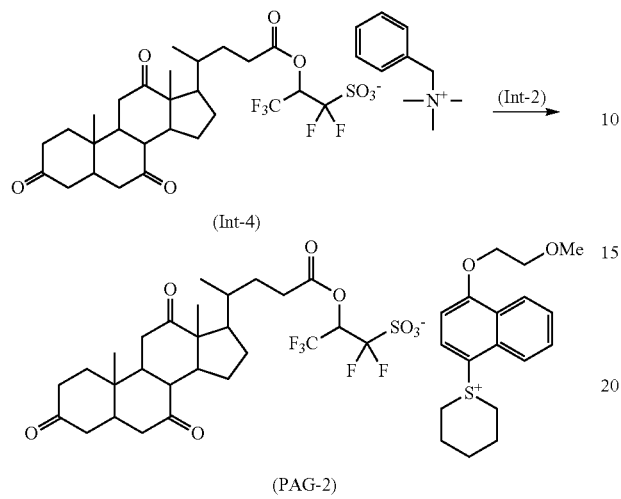

(Int-4)

(PAG-2)

A mixture of 4.1 g of benzyltrimethylammonium 1,1,3,3-pentafluoro-2-(3,7,12-trioxocholanoyloxy)-1-propanesulfonate (Int-4), 13.2 g of the aqueous solution of Int-2, 30 g of methyl isobutyl ketone, and 20 g of deionized water was stirred for 30 minutes, after which the organic layer was taken out. The organic layer was washed 5 times with an aqueous dilution of 3 g Int-2 aqueous solution diluted with 20 g deionized water, 3 times with 25 g of 20 wt % methanol aqueous solution, and twice with 20 g of deionized water. The organic layer was concentrated under reduced pressure. The concentrate was dissolved in 10 g of methylene chloride, and 12 g of diisopropyl ether was added thereto, followed by decantation. The resulting oil was dissolved in 10 g of methylene chloride, after which 70 g of diisopropyl ether was added thereto for crystallization. After stirring for 20 minutes, the precipitated solids were filtered and washed twice with diisopropyl ether. The wet crystals were vacuum dried at 50° C., obtaining 3.6 g (yield 69%) of the target compound, 1-[4-(2-methoxyethoxy)naphthyl]thian-1-ium 1,1,3,3,3-pentafluoro-2-(3,7,12-trioxo-cholanoyloxy)-1-propanesulfonate (PAG-2). It was analyzed by $^1$H-NMR, $^{19}$F-NMR and MALDI TOF-MS, with the results shown below.

$^1$H-NMR (500 MHz, DMSO-$d_6$):

δ=0.75 (3H, m), 0.99 (3H, s), 1.18-1.30 (4H, m), 1.32 (3H, s), 1.48 (1H, dt), 1.63-2.05 (13H, m), 2.07-2.52 (9H, m), 2.82 (1H, t), 2.97 (1H, dd), 3.04 (1H, dt), 3.38 (3H, s), 3.76-3.87 (6H, m), 4.46 (2H, m), 5.93 (1H, m), 7.36 (1H, d), 7.74 (1H, m), 7.85 (1H, m), 8.34 (1H, d), 8.37 (1H, d), 8.50 (1H, d) ppm $^{19}$F-NMR (500 MHz, DMSO-$d_6$):

δ=−119.8 (1F, m), −113.8 (1F, m), −72.3 (3F, m) ppm

MALDI TOF-MS

Positive M$^+$ 303 (corresponding to $C_{18}H_{23}O_2S^+$)

Negative M$^-$ 613 (corresponding to $C_{27}H_{34}F_5O_8S^-$)

Synthesis Example 1-3

Synthesis of PAG-3

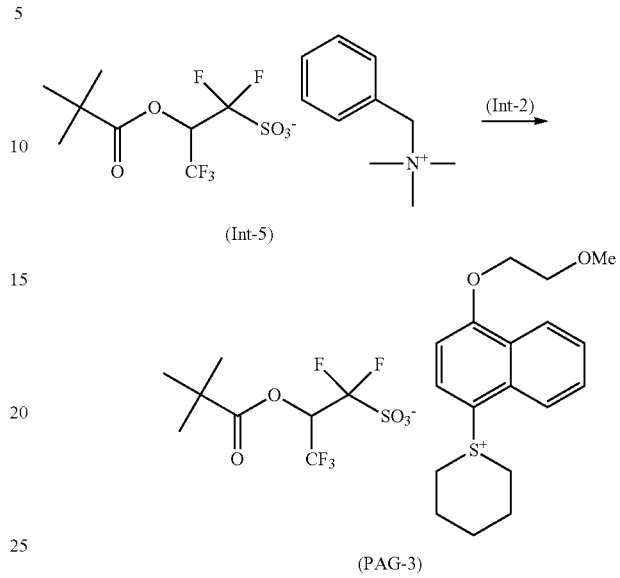

(Int-5)

(PAG-3)

A mixture of 35.9 g of an aqueous solution (concentration 0.42 mmol/g) of benzyltrimethylammonium 1,1,3,3,3-pentafluoro-2-pivaloyloxy-1-propanesulfonate (Int-5), 40.0 g of the aqueous solution of Int-2, and 50 g of methylene chloride was stirred for 30 minutes, after which the organic layer was taken out. The organic layer was washed 5 times with 40 g of deionized water. 20 g of methyl isobutyl ketone was added to the organic layer, which was concentrated at 50° C. under reduced pressure to remove the methylene chloride. 55.6 g of diisopropyl ether was added to the concentrate for crystallization. The precipitated solids were filtered and washed once with diisopropyl ether. The solids were vacuum dried at 50° C., obtaining 7.2 g (yield 79%) of the target compound, 1-[4-(2-methoxyethoxy)naphthyl]thian-1-ium 1,1,3,3,3-pentafluoro-2-pivaloyloxy-1-propanesulfonate (PAG-3). It was analyzed by $^1$H-NMR, $^{19}$F-NMR, IR and MALDI TOF-MS, with the results shown below.

$^1$H-NMR (500 MHz, DMSO-$d_6$):

δ=1.16 (9H, s), 1.71 (1H, m), 1.85 (1H, m), 1.99 (2H, m), 2.33 (2H, m), 3.38 (3H, s), 3.77-3.87 (6H, m), 4.46 (2H, m), 5.94 (1H, m), 7.36 (1H, d), 7.74 (1H, m), 7.85 (1H, m), 8.34 (1H, d), 8.37 (1H, d), 8.50 (1H, d) ppm $^{19}$F-NMR (500 MHz, DMSO-$d_6$):

δ=−119.4 (1F, m), −113.2 (1F, m), −72.2 (3F, m) ppm

IR (D-ATR):

ν=2985, 2940, 2824, 1770, 1590, 1574, 1510, 1451, 1431, 1392, 1378, 1325, 1263, 1244, 1214, 1186, 1168, 1127, 1093, 1071, 1026, 992, 969, 917, 852, 837, 777, 769, 642, 592 cm$^{-1}$

MALDI TOF-MS

Positive M$^+$ 303 (corresponding to $C_{18}H_{23}O_2S^+$)

Negative M$^-$ 313 (corresponding to $C_8H_{10}F_5O_5S^-$)

With reference to the foregoing Synthesis Examples, the following compounds PAG-4 to PAG-9 were synthesized.

(PAG-4)
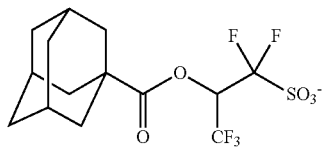
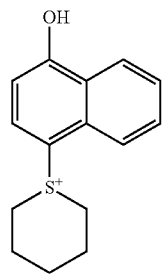

(PAG-5)
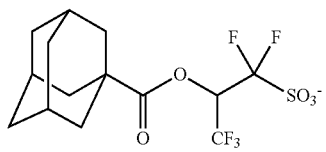

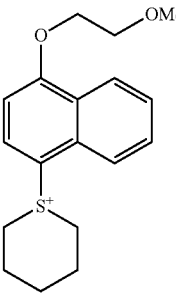

(PAG-8)
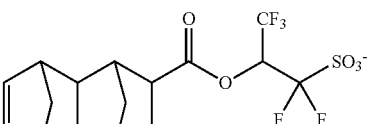

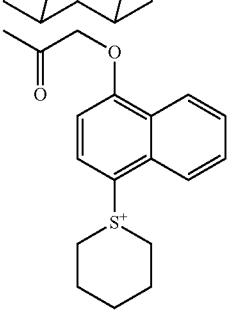

(PAG-6)
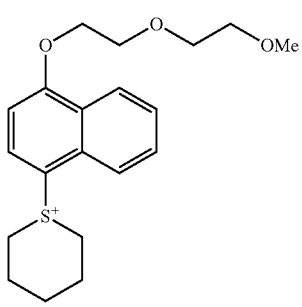

(PAG-9)
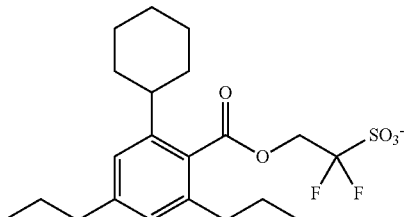

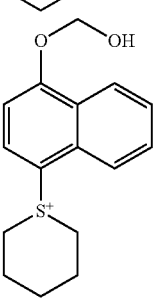

(PAG-7)
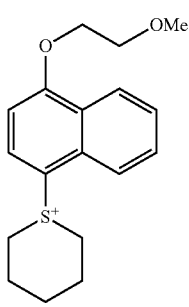

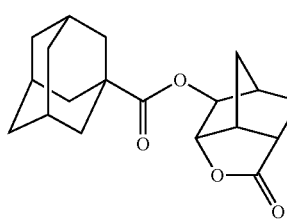

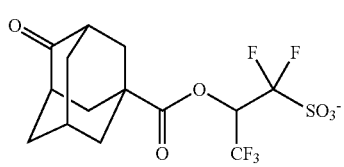

[2] Synthesis of Polymers

Synthesis Example 2-1

Synthesis of Polymer P-1

In a flask under nitrogen atmosphere, 22 g of 1-tert-butylcyclopentyl methacrylate, 17 g of 2-oxotetrahydrofuran-3-yl methacrylate, 0.48 g of dimethyl 2,2'-azobis(2-methylpropionate) (V-601 by Wako Pure Chemical Industries, Ltd.), 0.41 g of 2-mercaptoethanol, and 50 g of methyl ethyl ketone were combined to form a monomer/initiator solution. Another flask in nitrogen atmosphere was charged with 23 g of methyl ethyl ketone, which was heated at 80° C. with stirring. With stirring, the monomer/initiator solution was added dropwise to the flask over 4 hours. After the completion of dropwise addition, the polymerization solution was continuously stirred for 2 hours while maintaining the temperature of 80° C. The polymerization solution was cooled to room temperature, whereupon it was added dropwise to 640 g of methanol with vigorous stirring. The precipitate was collected by filtration, washed twice with 240 g of methanol, and vacuum dried at 50° C. for 20 hours, obtaining 36 g of Polymer P-1 in white powder form (yield 90%). On GPC analysis, Polymer P-1 had a Mw of 8,200 and a dispersity Mw/Mn of 1.63.

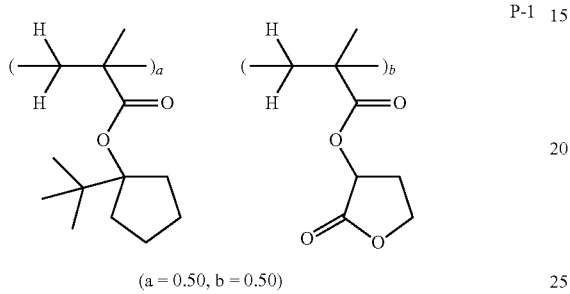

P-1

(a = 0.50, b = 0.50)

Synthesis Examples 2-2 to 2-5

Synthesis of Polymers P-2 to P-5

Polymers P-2 to P-5 were synthesized by the same procedure as in Synthesis Example 2-1 aside from changing the type and amount of monomers.

The composition of Polymers P-1 to P-5 is shown in Table 1. Table 1 shows the molar ratio of units incorporated in the polymers, and Tables 2 and 3 show the structure of recurring units.

TABLE 1

| Polymer | Unit 1 (ratio) | Unit 2 (ratio) | Unit 3 (ratio) | Unit 4 (ratio) | Unit 5 (ratio) | Mw | Mw/Mn |
|---|---|---|---|---|---|---|---|
| P-1 | A-1 (0.50) | B-1 (0.50) | — | — | — | 8,200 | 1.63 |
| P-2 | A-1 (0.30) | A-3 (0.20) | B-2 (0.40) | B-4 (0.10) | — | 7,900 | 1.65 |
| P-3 | A-1 (0.35) | A-4 (0.10) | B-2 (0.25) | B-3 (0.20) | B-5 (0.10) | 8,800 | 1.72 |
| P-4 | A-2 (0.40) | A-4 (0.10) | B-1 (0.10) | B-3 (0.30) | B-5 (0.10) | 8,200 | 1.65 |
| P-5 | A-2 (0.35) | A-3 (0.25) | B-1 (0.20) | B-2 (0.15) | B-5 (0.05) | 9,100 | 1.74 |

TABLE 2

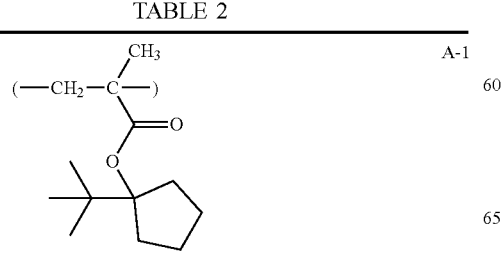

A-1

TABLE 2-continued

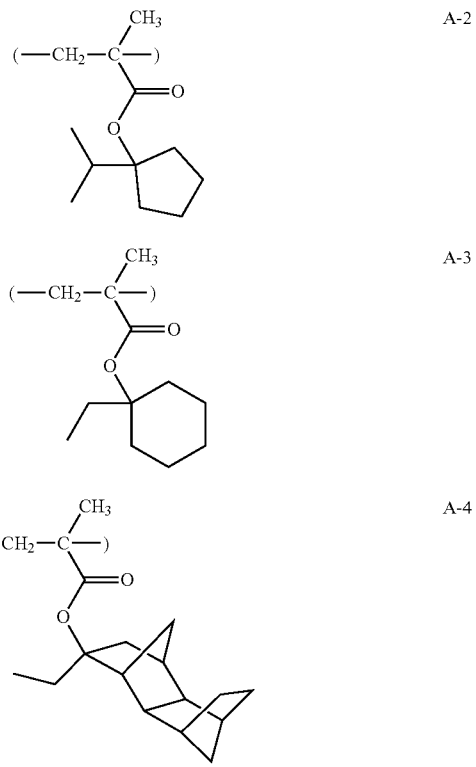

TABLE 3

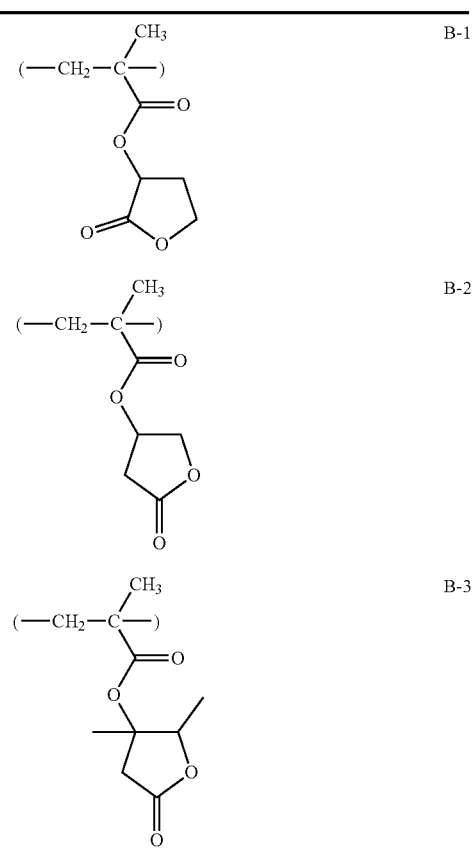

TABLE 3-continued

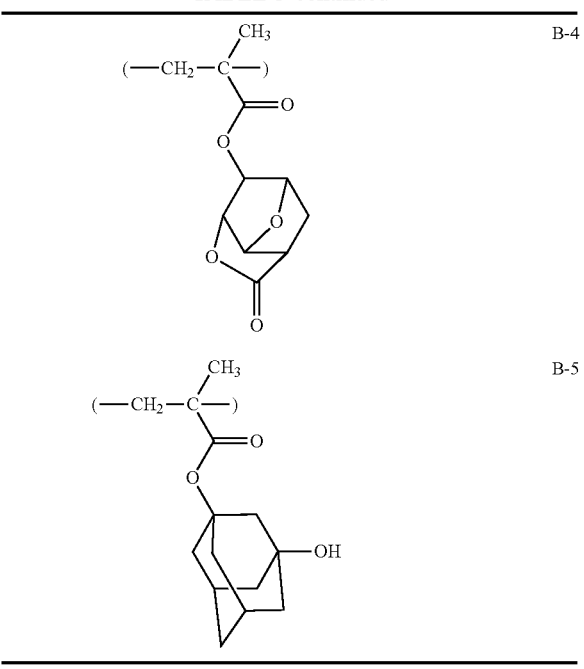

B-4

B-5

[3] Preparation of Resist Composition

Examples 1-1 to 1-15 and Comparative Examples 1-1 to 1-13

Resist compositions in solution form were prepared by dissolving photoacid generator (PAG-1 to PAG-3), polymer (P-1 to P-5), quencher (Q-1 to Q-3), other photoacid generator (PAG-X to PAG-Z), and alkali-soluble surfactant (SF-1) in a solvent containing 0.01 wt % of surfactant A in accordance with the formulation shown in Tables 4 and 5, and filtering through a Teflon® filter with a pore size of 0.2 µm. Comparative resist compositions were similarly prepared using photoacid generators (PAG-A to PAG-F).

The quenchers Q-1 to Q-3, solvents, photoacid generators PAG-X to PAG-Z, comparative photoacid generators PAG-A to PAG-F, and alkali-soluble surfactant SF-1, and surfactant A in Tables 4 and 5 are identified below.

Quenchers Q-1 to Q-3:

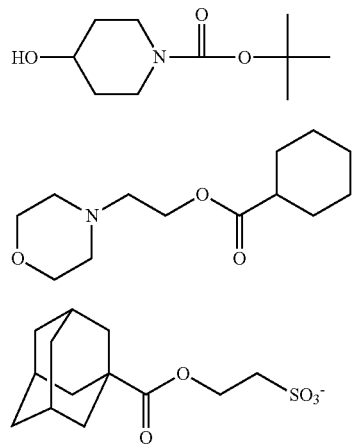

(Q-1)

(Q-2)

(Q-3)

-continued

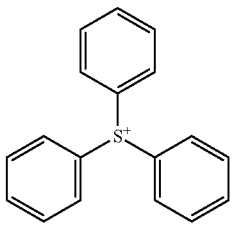

Solvent:
  PGMEA=propylene glycol monomethyl ether acetate
  GBL=γ-butyrolactone
  CyHO=cyclohexanone Photoacid Generators PAG-X to PAG-Z:

(PAG-X)

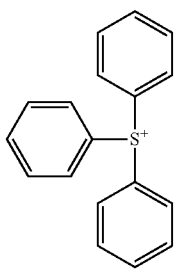 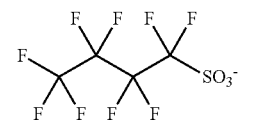

(PAG-Y)

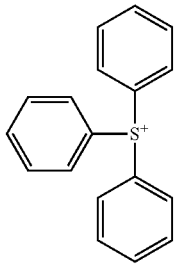 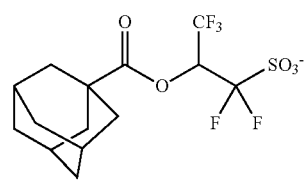

(PAG-Z)

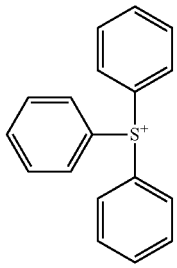

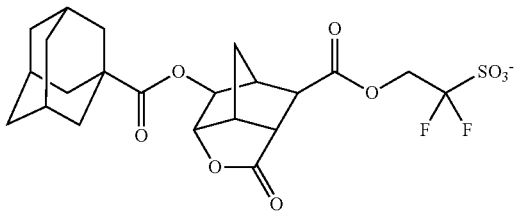

Comparative Photoacid Generators PAG-A to PAG-F:

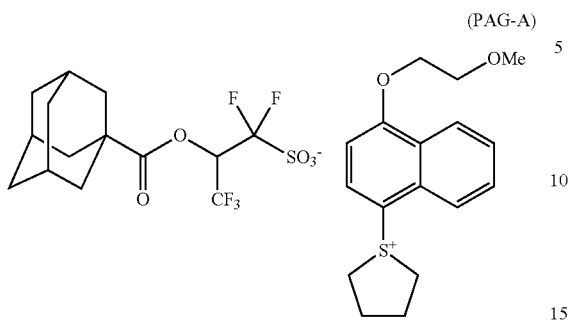
(PAG-A)

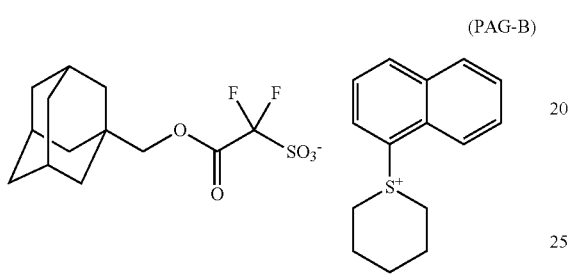
(PAG-B)

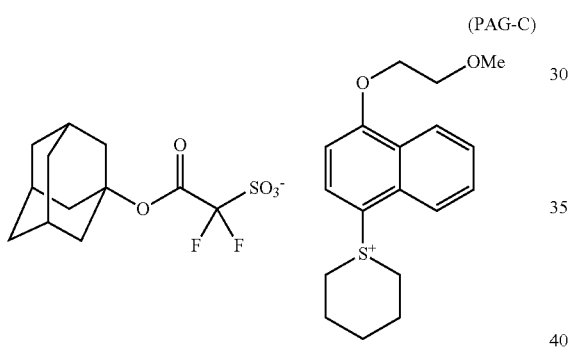
(PAG-C)

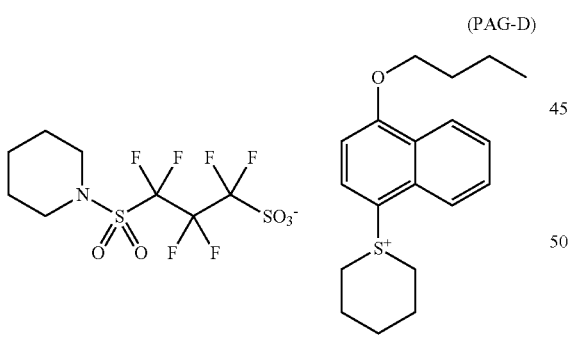
(PAG-D)

(PAG-E)

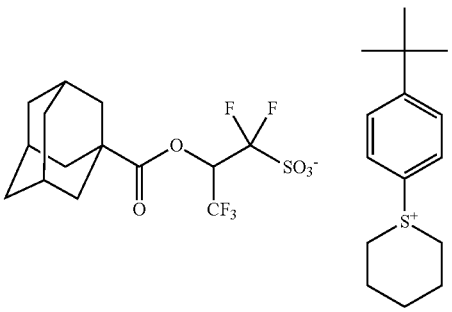
(PAG-F)

Alkali-soluble surfactant SF-1:
poly(2,2,3,3,4,4,4-heptafluoro-1-isobutyl-1-butyl methacrylate/9-(2,2,2-trifluoro-1-trifluoromethylethyloxycarbonyl)-4-oxatricyclo[4.2.1.0$^{3,7}$]nonan-5-on-2-yl methacrylate)
Mw=7,700
Mw/Mn=1.82

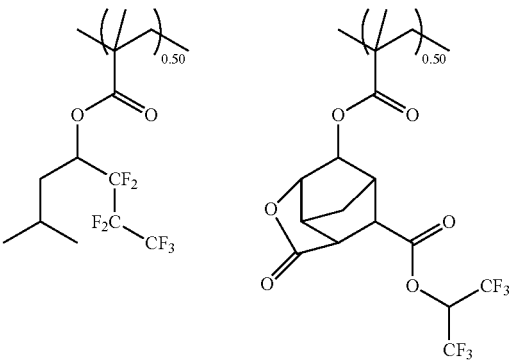
SF-1

Surfactant A:
3-methyl-3-(2,2,2-trifluoroethoxymethyl)oxetane/tetrahydrofuran/2,2-dimethyl-1,3-propane diol copolymer (Omnova Solutions, Inc.)

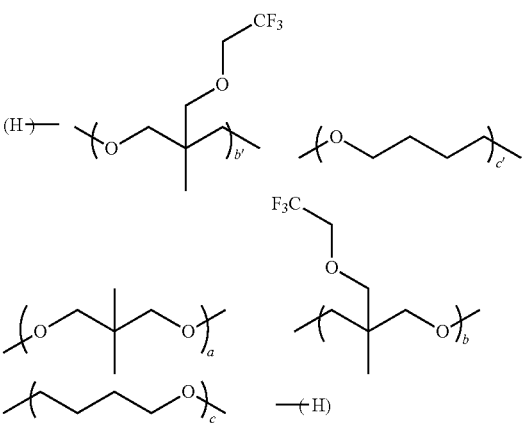

a:(b+b'):(c+c')=1:4-7:0.01-1 (molar ratio)
Mw=1,500

TABLE 4

| Resist composition | | Polymer (pbw) | Acid generator (pbw) | Quencher (pbw) | Surfactant (pbw) | Solvent (pbw) |
|---|---|---|---|---|---|---|
| Example | 1-1 | R-1 | P-1 (80) | PAG-1 (10.0) | Q-1 (1.5) | SF-1 (3.0) | PGMEA/GBL (1,536/384) |
| | 1-2 | R-2 | P-1 (80) | PAG-2 (8.0) PAG-X (2.0) | Q-2 (1.0) | SF-1 (3.0) | PGMEA/GBL/CyHO (1,536/192/192) |
| | 1-3 | R-3 | P-2 (80) | PAG-3 (6.0) PAG-Z (4.0) | Q-3 (2.0) | SF-1 (3.0) | PGMEA/CyHO (1,344/576) |
| | 1-4 | R-4 | P-3 (80) | PAG-4 (5.0) PAG-Y (2.5) | — | SF-1 (3.0) | PGMEA/CyHO (1,344/576) |
| | 1-5 | R-5 | P-3 (80) | PAG-5 (10.0) | Q-2 (1.5) | SF-1 (3.0) | PGMEA/GBL (1,536/384) |
| | 1-6 | R-6 | P-4 (80) | PAG-6 (5.0) PAG-Z (5.0) | Q-1 (2.0) | SF-1 (3.0) | PGMEA/GBL/CyHO (1,536/96/288) |
| | 1-7 | R-7 | P-1 (80) | PAG-7 (10.0) | Q-1 (1.5) | SF-1 (3.0) | PGMEA/GBL (1,536/384) |
| | 1-8 | R-8 | P-5 (80) | PAG-8 (9.0) PAG-X (1.0) | Q-2 (1.0) | SF-1 (3.0) | PGMEA/GBL/CyHO (1,536/96/288) |
| | 1-9 | R-9 | P-5 (80) | PAG-9 (2.5) PAG-X (5.5) | Q-1 (1.5) | SF-1 (3.0) | PGMEA/CyHO (1,344/576) |
| | 1-10 | R-10 | P-3 (80) | PAG-1 (10.0) | Q-2 (1.5) | SF-1 (3.0) | PGMEA/GBL (1,536/384) |
| | 1-11 | R-11 | P-4 (80) | PAG-1 (1.5) PAG-X (8.0) | Q-2 (1.5) | SF-1 (3.0) | PGMEA/CyHO (1,344/576) |
| | 1-12 | R-12 | P-3 (80) | PAG-2 (10.0) | Q-2 (1.5) | SF-1 (3.0) | PGMEA/GBL (1,536/384) |
| | 1-13 | R-13 | P-3 (80) | PAG-4 (10.0) | Q-2 (1.5) | SF-1 (3.0) | PGMEA/GBL (1,536/384) |
| | 1-14 | R-14 | P-1 (80) | PAG-5 (10.0) | Q-1 (1.5) | SF-1 (3.0) | PGMEA/GBL (1,536/384) |
| | 1-15 | R-15 | P-3 (80) | PAG-6 (10.0) | Q-2 (1.5) | SF-1 (3.0) | PGMEA/GBL (1,536/384) |
| Comparative Example | 1-1 | R-16 | P-3 (80) | PAG-A (10.0) | Q-2 (1.5) | SF-1 (3.0) | PGMEA/GBL (1.536/384) |
| | 1-2 | R-17 | P-3 (80) | PAG-B (10.0) | Q-2 (1.5) | SF-1 (3.0) | PGMEA/GBL (1,536/384) |
| | 1-3 | R-18 | P-3 (80) | PAG-C (10.0) | Q-2 (1.5) | SF-1 (3.0) | PGMEA/GBL (1.536/384) |
| | 1-4 | R-19 | P-3 (80) | PAG-D (10.0) | Q-2 (1.5) | SF-1 (3.0) | PGMEA/GBL (1,536/384) |
| | 1-5 | R-20 | P-3 (80) | PAG-E (10.0) | Q-2 (1.5) | SF-1 (3.0) | PGMEA/GBL (1.536/384) |
| | 1-6 | R-21 | P-3 (80) | PAG-F (10.0) | Q-2 (1.5) | SF-1 (3.0) | PGMEA/GBL (1,536/384) |
| | 1-7 | R-22 | P-1 (80) | PAG-A (10.0) | Q-1 (1.5) | SF-1 (3.0) | PGMEA/GBL (1,536/384) |
| | 1-8 | R-23 | P-1 (80) | PAG-C (10.0) | Q-1 (1.5) | SF-1 (3.0) | PGMEA/GBL (1,536/384) |
| | 1-9 | R-24 | P-1 (80) | PAG-E (10.0) | Q-1 (1.5) | SF-1 (3.0) | PGMEA/GBL (1,536/384) |
| | 1-10 | R-25 | P-1 (80) | PAG-F (10.0) | Q-1 (1.5) | SF-1 (3.0) | PGMEA/GBL (1.536/384) |
| | 1-11 | R-26 | P-1 (80) | PAG-C (8.0) PAG-X (2.0) | Q-2 (1.0) | SF-1 (3.0) | PGMEA/GBL/CyHO (1.536/192/192) |
| | 1-12 | R-27 | P-2 (80) | PAG-B (6.0) PAG-Z (4.0) | Q-3 (2.0) | SF-1 (3.0) | PGMEA/CyHO (1,344/576) |
| | 1-13 | R-28 | P-3 (80) | PAG-F (5.0) PAG-Y (2.5) | — | SF-1 (3.0) | PGMEA/CyHO (1,344/576) |

[4] ArF Lithography Test #1:
Evaluation of hole pattern printed by negative tone development Examples 2-1 to 2-15 and Comparative Examples 2-1 to 2-13

On a substrate, a spin-on carbon film ODL-101 (Shin-Etsu Chemical Co., Ltd.) was deposited to a thickness of 200 nm and a silicon-containing spin-on hard mask SHB-A940 (Shin-Etsu Chemical Co., Ltd.) having a silicon content of 43 wt % was deposited thereon to a thickness of 35 nm. On this substrate for trilayer process, each of the resist compositions (R-1 to R-15) and comparative resist compositions (R-16 to R-28) was spin coated, then to baked on a hotplate at 100° C. for 60 seconds to form a resist film of 100 nm thick.

Using an ArF excimer laser immersion lithography stepper (NSR-610C by Nikon Corp., NA 1.30, σ 0.98/0.78, dipole opening 20 deg., azimuthally polarized illumination, dipole illumination, 6% halftone phase shift mask), the resist film was exposed through a first mask having X-axis direction lines with a pitch of 80 nm and a line width of 40 nm (on-wafer size) and then through a second mask having Y-axis direction lines with a pitch of 80 nm and a line width of 40 nm (on-wafer size). Water was used as the immersion liquid. After exposure, the resist film was baked (PEB) at the temperature shown in Table 6 for 60 seconds and developed to form a hole pattern. Specifically, butyl acetate was injected from a development nozzle for 3 seconds while the wafer was spun at 30 rpm, which was followed by stationary puddle development for 27 seconds. The hole pattern thus formed was observed under CD-SEM (CG-5000 by Hitachi High-Technologies Corp.) and evaluated for sensitivity, mask error factor (MEF), critical dimension uniformity (CDU) and depth of focus (DOF) by the following methods. The results are shown in Table 6.

Evaluation of Sensitivity

The optimum dose (Eop) is a dose (mJ/cm$^2$) which provides a hole pattern having a diameter of 40 nm at a pitch of 80 nm and reported as sensitivity. A smaller value indicates a higher sensitivity.

Evaluation of MEF

A pattern was formed by exposure in Eop (determined in the sensitivity evaluation) through a mask with the pitch fixed and the line width varied. MEF was calculated from variations of the mask line width and the pattern space width according to the following equation:

MEF=(pattern space width)/(mask line width)−b wherein b is a constant.

Evaluation of CDU

For the hole pattern printed at Eop, the diameter of 125 holes was measured. A three-fold value (3σ) of a standard variation (σ) was computed therefrom as a variation of hole size and reported as CDU. A smaller value of 3σ indicates a less size variation of holes.

Evaluation of DOF

Hole patterns were formed by exposure in Eop while changing the focus stepwise. The span of focus within which the hole size was in the range of 40 nm±5% (from 38 nm to 42 nm) was determined as DOF margin. A larger value indicates a smaller change of pattern size per DOF change and hence, better DOF margin.

TABLE 6

| | | Resist composition | PEB temp. (° C.) | Eop (mJ/cm$^2$) | MEF | CDU (nm) | DOF (nm) |
|---|---|---|---|---|---|---|---|
| Example | 2-1 | R-1 | 95 | 45 | 2.8 | 3.3 | 140 |
| | 2-2 | R-2 | 95 | 40 | 2.6 | 3.3 | 170 |
| | 2-3 | R-3 | 100 | 37 | 2.8 | 3.1 | 150 |
| | 2-4 | R-4 | 105 | 39 | 2.9 | 3.3 | 140 |
| | 2-5 | R-5 | 110 | 44 | 2.7 | 3.0 | 150 |
| | 2-6 | R-6 | 110 | 39 | 2.5 | 2.9 | 180 |
| | 2-7 | R-7 | 95 | 41 | 2.9 | 3.1 | 160 |
| | 2-8 | R-8 | 110 | 40 | 2.6 | 2.8 | 180 |
| | 2-9 | R-9 | 105 | 39 | 2.6 | 2.9 | 190 |
| | 2-10 | R-10 | 110 | 42 | 2.8 | 3.3 | 160 |
| | 2-11 | R-11 | 110 | 40 | 2.6 | 2.9 | 180 |
| | 2-12 | R-12 | 110 | 41 | 2.7 | 2.9 | 160 |
| | 2-13 | R-13 | 110 | 45 | 2.7 | 3.0 | 150 |
| | 2-14 | R-14 | 95 | 40 | 2.9 | 3.2 | 130 |
| | 2-15 | R-15 | 110 | 43 | 2.6 | 2.9 | 175 |
| Comparative Example | 2-1 | R-16 | 110 | 35 | 3.2 | 3.5 | 120 |
| | 2-2 | R-17 | 110 | 41 | 3.2 | 3.4 | 110 |
| | 2-3 | R-18 | 110 | 42 | 3.1 | 3.4 | 100 |
| | 2-4 | R-19 | 110 | 45 | 3.3 | 3.6 | 120 |
| | 2-5 | R-20 | 110 | 40 | 3.1 | 3.7 | 110 |
| | 2-6 | R-21 | 110 | 42 | 3.2 | 3.5 | 130 |
| | 2-7 | R-22 | 95 | 36 | 3.2 | 3.7 | 100 |
| | 2-8 | R-23 | 95 | 39 | 3.3 | 3.6 | 100 |
| | 2-9 | R-24 | 95 | 41 | 3.4 | 3.6 | 110 |
| | 2-10 | R-25 | 95 | 43 | 3.4 | 3.6 | 100 |
| | 2-11 | R-26 | 95 | 40 | 3.1 | 3.5 | 120 |
| | 2-12 | R-27 | 100 | 38 | 3.4 | 3.7 | 110 |
| | 2-13 | R-28 | 105 | 39 | 3.4 | 3.6 | 100 |

It is evident from Table 6 that the inventive resist composition is improved in MEF, CDU and DOF upon hole pattern formation via organic solvent development.

[5] ArF Lithography Patterning Test #2:

Evaluation of line-and-space pattern printed by negative tone development

Examples 3-1 to 3-15 and Comparative Examples 3-1 to 3-13

On a substrate, a spin-on carbon film ODL-101 (Shin-Etsu Chemical Co., Ltd.) was deposited to a thickness of 200 nm and a silicon-containing spin-on hard mask SHB-A940 (Shin-Etsu Chemical Co., Ltd.) having a silicon content of 43 wt % was deposited thereon to a thickness of 35 nm. On this substrate for trilayer process, each of the inventive resist compositions (R-1 to R-15) and comparative resist compositions (R-16 to R-28) was spin coated and baked on a hotplate at 100° C. for 60 seconds to form a resist film of 100 nm thick.

Using an ArF excimer laser immersion lithography scanner NSR-610C (Nikon Corp., NA 1.30, σ 0.98/0.78, 4/5 annular illumination), pattern exposure was performed through a 6% halftone phase shift mask bearing a pattern with a pitch of 100 nm and a line width of 50 nm (on-wafer size). Water was used as the immersion liquid. After exposure, the wafer was baked (PEB) at the temperature shown in Table 7 for 60 seconds and developed. Specifically, butyl acetate was injected from a development nozzle for 3 seconds while the wafer was spun at 30 rpm, which was followed by stationary puddle development for 27 seconds. As a result of image reversal where the unexposed regions of the resist film which had been shielded by the mask were dissolved in the developer, a line-and-space (L/S) pattern with a space width of 50 nm and a pitch of 100 nm was printed. The L/S pattern was observed under CD-SEM (CG-5000 by Hitachi High-Technologies Corp.) and evaluated for sensitivity, MEF, LWR and DOF by the following methods. The results are shown in Table 7.

Evaluation of Sensitivity

The optimum dose (Eop) is a dose (mJ/cm$^2$) which provides a L/S pattern with a space width of 50 nm and a pitch of 100 nm and reported as sensitivity. A smaller value indicates a higher sensitivity.

Evaluation of MEF

A pattern was formed by exposure in the optimum dose Eop (determined in the sensitivity evaluation) through a mask with the pitch fixed and the line width varied. MEF was calculated from variations of the mask line width and the pattern space width according to the following equation:

MEF=(pattern space width)/(mask line width)−b wherein b is a constant. A value closer to unity (1) indicates better performance.

Evaluation of LWR

On the L/S pattern formed by exposure in the optimum dose Eop, the space width was measured at longitudinally spaced apart 10 points, from which a 3-fold value (3a) of standard deviation (σ) was determined and reported as LWR. A smaller value of 3a indicates a pattern having a lower roughness and more uniform space width.

Evaluation of DOF

L/S patterns were formed by exposure in Eop while changing the focus stepwise. The span of focus within which the line width of L/S pattern was in the range of 50 nm±5% (from 47.5 nm to 52.5 nm) was determined as DOF margin. A larger value indicates a smaller change of pattern size per DOF change and hence, better DOF margin.

TABLE 7

| | | Resist composition | PEB temp. (° C.) | Eop (mJ/cm²) | MEF | LWR (nm) | DOF (nm) |
|---|---|---|---|---|---|---|---|
| Example | 3-1 | R-1 | 95 | 44 | 2.9 | 2.9 | 160 |
| | 3-2 | R-2 | 95 | 41 | 2.7 | 2.8 | 190 |
| | 3-3 | R-3 | 100 | 37 | 2.9 | 2.8 | 170 |
| | 3-4 | R-4 | 105 | 39 | 2.9 | 2.9 | 160 |
| | 3-5 | R-5 | 110 | 45 | 2.8 | 2.6 | 160 |
| | 3-6 | R-6 | 110 | 38 | 2.5 | 2.5 | 190 |
| | 3-7 | R-7 | 95 | 41 | 2.9 | 2.7 | 180 |
| | 3-8 | R-8 | 110 | 42 | 2.7 | 2.3 | 190 |
| | 3-9 | R-9 | 105 | 38 | 2.6 | 2.5 | 180 |
| | 3-10 | R-10 | 110 | 42 | 2.9 | 2.8 | 160 |
| | 3-11 | R-11 | 110 | 42 | 2.7 | 2.5 | 170 |
| | 3-12 | R-12 | 110 | 41 | 2.6 | 2.4 | 180 |
| | 3-13 | R-13 | 110 | 45 | 2.7 | 2.6 | 170 |
| | 3-14 | R-14 | 95 | 39 | 2.8 | 2.8 | 150 |
| | 3-15 | R-15 | 110 | 44 | 2.6 | 2.4 | 180 |
| Comparative Example | 3-1 | R-16 | 110 | 35 | 3.3 | 3.1 | 140 |
| | 3-2 | R-17 | 110 | 41 | 3.3 | 3.0 | 120 |
| | 3-3 | R-18 | 110 | 43 | 3.2 | 3.0 | 120 |
| | 3-4 | R-19 | 110 | 44 | 3.3 | 3.1 | 130 |
| | 3-5 | R-20 | 110 | 40 | 3.2 | 3.3 | 130 |
| | 3-6 | R-21 | 110 | 42 | 3.2 | 3.2 | 120 |
| | 3-7 | R-22 | 95 | 36 | 3.3 | 3.3 | 120 |
| | 3-8 | R-23 | 95 | 40 | 3.4 | 3.2 | 120 |
| | 3-9 | R-24 | 95 | 43 | 3.4 | 3.3 | 100 |
| | 3-10 | R-25 | 95 | 42 | 3.5 | 3.2 | 130 |
| | 3-11 | R-26 | 95 | 40 | 3.2 | 3.1 | 110 |
| | 3-12 | R-27 | 100 | 38 | 3.5 | 3.3 | 120 |
| | 3-13 | R-28 | 105 | 40 | 3.3 | 3.2 | 120 |

It is evident from Table 7 that the inventive resist composition is improved in MEF, LWR and DOF upon L/S pattern formation via organic solvent development. This suggests that the inventive resist composition is suited for the organic solvent development process.

[6] ArF Lithography Patterning Test #3:
Evaluation of line-and-space pattern printed by positive tone development

Examples 4-1 to 4-15 and Comparative Examples 4-1 to 4-13

On a substrate, a spin-on carbon film ODL-101 (Shin-Etsu Chemical Co., Ltd.) was deposited to a thickness of 200 nm and a silicon-containing spin-on hard mask SHB-A940 (Shin-Etsu Chemical Co., Ltd.) having a silicon content of 43 wt % was deposited thereon to a thickness of 35 nm. On this substrate for trilayer process, each of the inventive resist compositions (R-1 to R-15) and comparative resist compositions (R-16 to R-28) was spin coated and baked on a hotplate at 100° C. for 60 seconds to form a resist film of 100 nm thick.

Using an ArF excimer laser immersion lithography scanner NSR-610C (Nikon Corp., NA 1.30, σ 0.98/0.78, 4/5 annular illumination), pattern exposure was performed through a 6% halftone phase shift mask bearing a pattern with a pitch of 100 nm and a space width of 50 nm (on-wafer size). Water was used as the immersion liquid. After exposure, the wafer was baked (PEB) at the temperature shown in Table 8 for 60 seconds and developed. Specifically, 2.38 wt % TMAH aqueous solution was injected from a development nozzle for 3 seconds while the wafer was spun at 30 rpm, which was followed by stationary puddle development for 27 seconds. As a result, the exposed regions of the resist film were dissolved in the developer to form a line-and-space (L/S) pattern with a space width of 50 nm and a pitch of 100 nm. The L/S pattern was observed under CD-SEM (CG-5000 by Hitachi High-Technologies Corp.) and evaluated for sensitivity, MEF, LWR and DOF by the following methods. The results are shown in Table 8.

Evaluation of Sensitivity

The optimum dose (Eop) is a dose (mJ/cm²) which provides a L/S pattern with a space width of 50 nm and a pitch of 100 nm and reported as sensitivity. A smaller value indicates a higher sensitivity.

Evaluation of MEF

A pattern was formed by exposure in the optimum dose Eop (determined in the sensitivity evaluation) through a mask with the pitch fixed and the space width varied. MEF was calculated from variations of the mask space width and the pattern space width according to the following equation:

MEF=(pattern space width)/(mask space width)–b wherein b is a constant. A value closer to unity (1) indicates better performance.

Evaluation of LWR

On the L/S pattern formed by exposure in the optimum dose Eop, the space width was measured at longitudinally spaced apart 10 points, from which a 3-fold value (3σ) of standard deviation (σ) was determined and reported as LWR. A smaller value of 3σ indicates a pattern having a lower roughness and more uniform space width.

Evaluation of DOF Margin

L/S patterns were formed by exposure in Eop while changing the focus stepwise. The span of focus within which the line width of L/S pattern was in the range of 50 nm±5% (from 47.5 nm to 52.5 nm) was determined as DOF margin. A larger value indicates a smaller change of pattern size per DOF change and hence, better DOF margin.

TABLE 8

| | | Resist composition | PEB temp. (° C.) | Eop (mJ/cm²) | MEF | LWR (nm) | DOF (nm) |
|---|---|---|---|---|---|---|---|
| Example | 4-1 | R-1 | 95 | 44 | 2.8 | 2.7 | 170 |
| | 4-2 | R-2 | 95 | 41 | 2.7 | 2.8 | 180 |
| | 4-3 | R-3 | 100 | 37 | 2.8 | 2.6 | 170 |
| | 4-4 | R-4 | 105 | 38 | 2.9 | 2.9 | 150 |
| | 4-5 | R-5 | 110 | 44 | 2.9 | 2.5 | 160 |
| | 4-6 | R-6 | 110 | 38 | 2.5 | 2.5 | 180 |
| | 4-7 | R-7 | 95 | 42 | 2.8 | 2.6 | 160 |
| | 4-8 | R-8 | 110 | 42 | 2.8 | 2.3 | 160 |
| | 4-9 | R-9 | 105 | 38 | 2.6 | 2.6 | 180 |
| | 4-10 | R-10 | 110 | 42 | 2.7 | 2.7 | 160 |
| | 4-11 | R-11 | 110 | 41 | 2.8 | 2.7 | 180 |
| | 4-12 | R-12 | 110 | 41 | 2.6 | 2.4 | 180 |
| | 4-13 | R-13 | 110 | 44 | 2.7 | 2.6 | 180 |
| | 4-14 | R-14 | 95 | 39 | 2.7 | 2.7 | 160 |
| | 4-15 | R-15 | 110 | 43 | 2.8 | 2.4 | 190 |
| Comparative Example | 4-1 | R-16 | 110 | 35 | 3.3 | 3.1 | 130 |
| | 4-2 | R-17 | 110 | 41 | 3.2 | 3.1 | 130 |
| | 4-3 | R-18 | 110 | 42 | 3.3 | 3.0 | 120 |
| | 4-4 | R-19 | 110 | 43 | 3.2 | 3.0 | 140 |
| | 4-5 | R-20 | 110 | 40 | 3.1 | 3.3 | 110 |
| | 4-6 | R-21 | 110 | 41 | 3.3 | 3.1 | 130 |
| | 4-7 | R-22 | 95 | 37 | 3.2 | 3.3 | 120 |
| | 4-8 | R-23 | 95 | 40 | 3.5 | 3.3 | 110 |
| | 4-9 | R-24 | 95 | 43 | 3.3 | 3.2 | 100 |
| | 4-10 | R-25 | 95 | 42 | 3.6 | 3.2 | 120 |
| | 4-11 | R-26 | 95 | 40 | 3.2 | 3.2 | 110 |
| | 4-12 | R-27 | 100 | 38 | 3.4 | 3.3 | 120 |
| | 4-13 | R-28 | 105 | 40 | 3.4 | 3.1 | 110 |

It is evident from Table 8 that the inventive resist composition is improved in MEF, LWR and DOF upon positive pattern formation via alkaline solution development. This suggests that the inventive resist composition is suited for the alkaline solution development process.

Japanese Patent Application No. 2019-018638 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A resist composition consisting of:
(A) a photoacid generator in the form of a sulfonium salt having the formula (1):

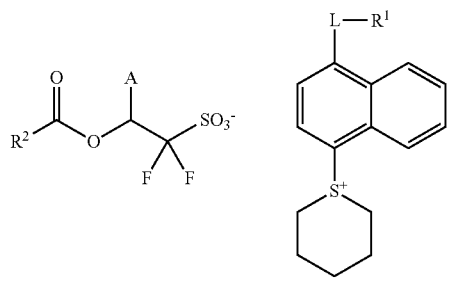

wherein $R^1$ is hydrogen or a $C_1$-$C_{10}$ monovalent hydrocarbon group which may contain a heteroatom, $R^2$ is a $C_1$-$C_{10}$ monovalent hydrocarbon group which may contain a heteroatom selected from the group consisting of oxygen, sulfur and nitrogen, L is a single bond, ether bond or thioether bond, and A is hydrogen or trifluormethyl, (B) a base polymer adapted to change its solubility in a developer under the action of an acid, and (C) an organic solvent, and optionally (D) a photoacid generator having the formula (2) or (3):

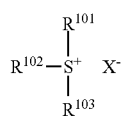

wherein the sulfonium cation in formula (2) is selected from the group consisting of the following formulae;

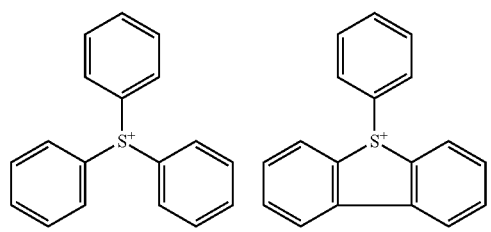

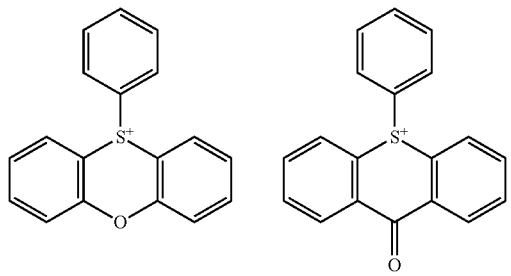

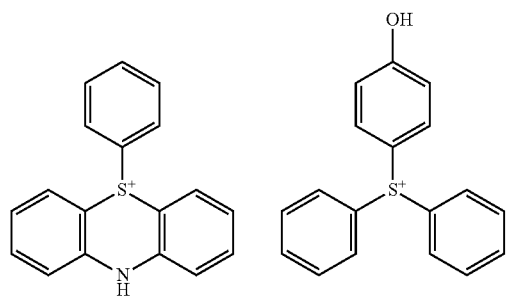

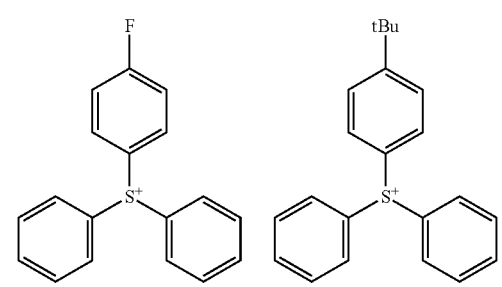

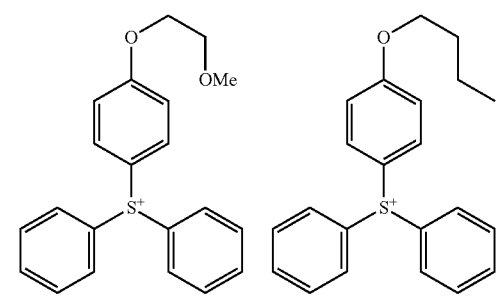

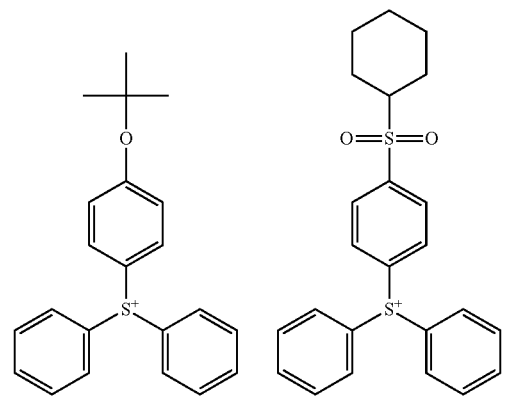

-continued

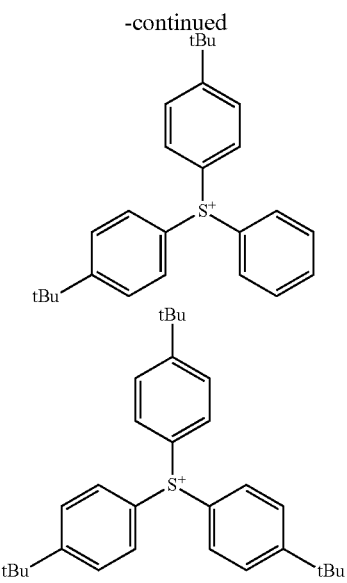

and X⁻ is an anion having the formula (2A) or (2B):

(2A)

(2B)

wherein $R^{fa}$ is fluorine, a $C_1$-$C_4$ perfluoroalkyl group, or a $C_1$-$C_{40}$ monovalent hydrocarbon group which may contain a heteroatom, and $R^{fb}$ is a $C_1$-$C_{40}$ monovalent hydrocarbon group which may contain a heteroatom,

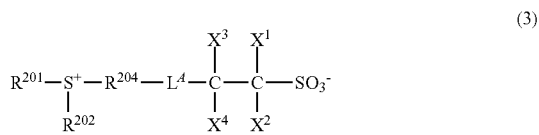
(3)

wherein $R^{201}$ and $R^{202}$ are each independently a $C_1$-$C_{30}$ monovalent hydrocarbon group which may contain a heteroatom, $R^{203}$ is a $C_1$-$C_{30}$ divalent hydrocarbon group which may contain a heteroatom, any two of $R^{201}$, $R^{202}$ and $R^{203}$ may bond together to form a ring with the sulfur atom to which they are attached, $L^A$ is a single bond, ether bond or a $C_1$-$C_{20}$ divalent hydrocarbon group which may contain a heteroatom, $X^1$, $X^2$, $X^3$ and $X^4$ are each independently hydrogen, fluorine or trifluoromethyl, at least one of $X^1$, $X^2$, $X^3$ and $X^4$ being fluorine or trifluoromethyl, (E) a quencher,
(F) a surfactant which is insoluble in water and soluble in alkaline developer, and/or
(G) other components selected from the group consisting of an acid amplifier compound, an organic acid derivative, a fluorinated alcohol, a crosslinker, a dissolution inhibitor and acetylene alcohol.

2. The resist composition of claim 1 wherein L is an ether bond and $R^1$ is 2-methoxyethyl.

3. The resist composition of claim 1 wherein A is trifluoromethyl.

4. The resist composition of claim 1 wherein the base polymer (B) comprises recurring units having the formula (a) and recurring units having the formula (b):

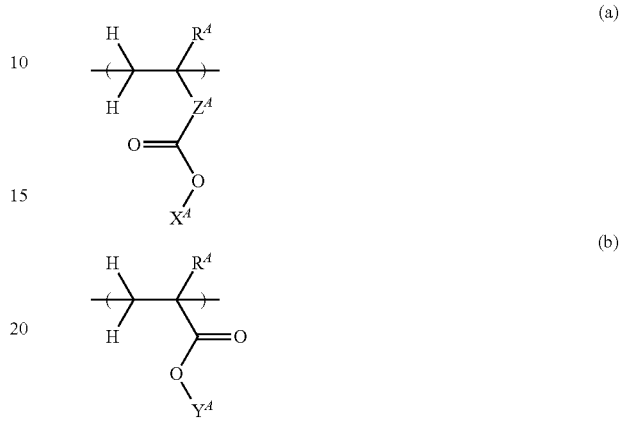

wherein $R^A$ is hydrogen or methyl, $Z^A$ is a single bond, phenylene group, naphthylene group or (backbone)-C(=O)—O—$Z^{A1}$—, $Z^{A1}$ is a $C_1$-$C_{10}$ alkanediyl group which may contain a hydroxyl moiety, ether bond, ester bond or lactone ring, or phenylene group or naphthylene group, $X^A$ is an acid labile group, and $Y^A$ is hydrogen or a polar group having at least one structure selected from the class consisting of hydroxyl, cyano, carbonyl, carboxyl, ether bond, ester bond, sulfonic acid ester bond, carbonate bond, lactone ring, sultone ring and carboxylic anhydride (—C(=O)—O—C(=O)—).

5. The resist composition of claim 4 wherein $Z^A$ is a single bond, and $X^A$ is a group having the formula (xa) or (xb):

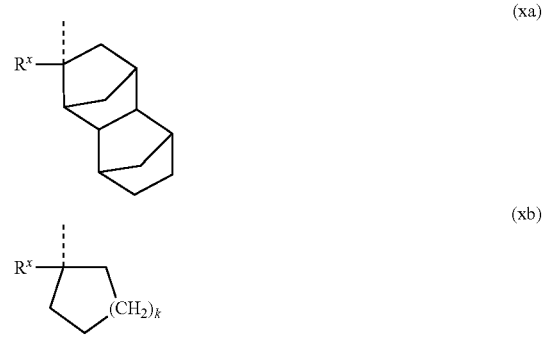

wherein RX is a $C_1$-$C_5$ straight or branched monovalent hydrocarbon group, k is 1 or 2, and the broken line designates a valence bond.

6. The resist composition of claim 4 wherein $Y^A$ is a monocyclic lactone ring.

7. The resist composition of claim 4 wherein the base polymer (B) comprises recurring units of at least two types having the formula (a).

8. The resist composition of claim 4 wherein the base polymer (B) comprises recurring units of at least two types having the formula (b).

9. A pattern forming process comprising the steps of applying the resist composition of claim 1 to form a resist film, exposing a selected region of the resist film to KrF excimer laser, ArF excimer laser, EB or EUV, and developing the exposed resist film in a developer.

10. The pattern forming process of claim 9 wherein the developing step uses an alkaline aqueous solution as the developer, thereby forming a positive pattern in which an exposed region of the resist film is dissolved away and an unexposed region of the resist film is not dissolved.

11. The pattern forming process of claim 9 wherein the developing step uses an organic solvent as the developer, thereby forming a negative pattern in which an unexposed region of the resist film is dissolved away and an exposed region of the resist film is not dissolved.

12. The pattern forming process of claim 11 wherein the organic solvent is at least one solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

13. The process of claim 9 wherein the exposure step is carried out by immersion lithography while a liquid having a refractive index of at least 1.0 is held between the resist film and a projection lens.

14. The process of claim 13, further comprising the step of coating a protective film on the resist film prior to the exposure step, wherein immersion lithography is carried out while the liquid is held between the protective film and the projection lens.

* * * * *